United States Patent
Garry et al.

(10) Patent No.: US 11,725,217 B2
(45) Date of Patent: Aug. 15, 2023

(54) METHODS TO ENHANCE MYOCARDIAL REGENERATION AND/OR REPAIR

(71) Applicant: Regents of the University of Minnesota, Minneapolis, MN (US)

(72) Inventors: Daniel J. Garry, Eagan, MN (US); Mary G. Garry, Eagan, MN (US); Bhairab Singh, Falcon Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 398 days.

(21) Appl. No.: 16/519,889

(22) Filed: Jul. 23, 2019

(65) Prior Publication Data
US 2020/0224218 A1    Jul. 16, 2020

Related U.S. Application Data

(60) Provisional application No. 62/702,743, filed on Jul. 24, 2018.

(51) Int. Cl.
| | |
|---|---|
| *A61K 48/00* | (2006.01) |
| *C12N 15/11* | (2006.01) |
| *C12N 15/12* | (2006.01) |
| *C12N 15/86* | (2006.01) |
| *A61P 9/00* | (2006.01) |
| *C12N 7/00* | (2006.01) |
| *A61K 31/5377* | (2006.01) |
| *A61K 35/76* | (2015.01) |

(52) U.S. Cl.
CPC .......... *C12N 15/86* (2013.01); *A61K 31/5377* (2013.01); *A61K 35/76* (2013.01); *A61P 9/00* (2018.01); *C12N 7/00* (2013.01); *A61K 48/00* (2013.01); *C12N 2740/15042* (2013.01); *C12N 2740/15043* (2013.01)

(58) Field of Classification Search
None
See application file for complete search history.

(56) References Cited

FOREIGN PATENT DOCUMENTS

WO    WO 2013110358    *   9/2013

OTHER PUBLICATIONS

Mathison et al, In vivo Cardiac Cellular Reprogramming Efficay is Enhanced wtih Angiogenic Preconditioning of the Infarcted Myocardim with Vacular Endothelial Growth Factor, JAHA, 2012, pp. 1-14.*
Shanks et al, Are animal models predictive for humans?, Philosophy, Ethics, and Humanities in Medicine 2009, pp. 1-20.*
Wolfram et al, Gene Therapy to Treat Cardiovascular Disease, JAHA, 2013, pp. 1-12.*
Kusano et al, Sonic hedgehog myocardial gene therapy: tissue repair through transient reconstitution of embryonic signaling, Nature Med, 2005, pp. 1197-1204.*
Zangi et al, Gene Therapy for Heart Disease: Modified mRNA Perspectives, Intech Open, 2021, pp. 1-18.*
Xiao et al, Impaired sonic hedgehog pathway contributes to cardiac dysfunction in type 1 diabetic mice with myocardial infarction, 2012, Cardiovascular Research, pp. 507-516.*
Harmelink et al, Myocardial Mycn is essential for mouse ventricular wall morphogenesis, Dev Biol. Jan. 1, 2013; 373(1): 53-63.*
Dunaeva et al, Hh signaling in regeneration of the ischemic heart, Cell. Mol. Life Sci. (2017) 74:3481-3490.*
Chechneva et al, A Smoothened receptor agonist is neuroprotective and promotes regeneration after ischemic brain injury, Cell Death & Disease Oct. 2014, pp. 1-12.*
Gianakopoulos and Skerjanc, Hedgehog Signaling Induces Cardiomyogenesis in P19 Cells*, JBC, 2005, 21022-21028.*

* cited by examiner

*Primary Examiner* — Maria Marvich
(74) *Attorney, Agent, or Firm* — Schwegman Lundberg & Woessner, P.A.

(57) ABSTRACT

A method is provided to enhance repair or regeneration of a mammalian cardiovascular system to include heart and/or vasculature comprising: administering to a mammal in need thereof a composition comprising an effective amount of an agent that elevates levels of Smo, Ptc1, Shh, Ihh, Dhh, Gli1, Gli2, or Mycn.

15 Claims, 28 Drawing Sheets

Specification includes a Sequence Listing.

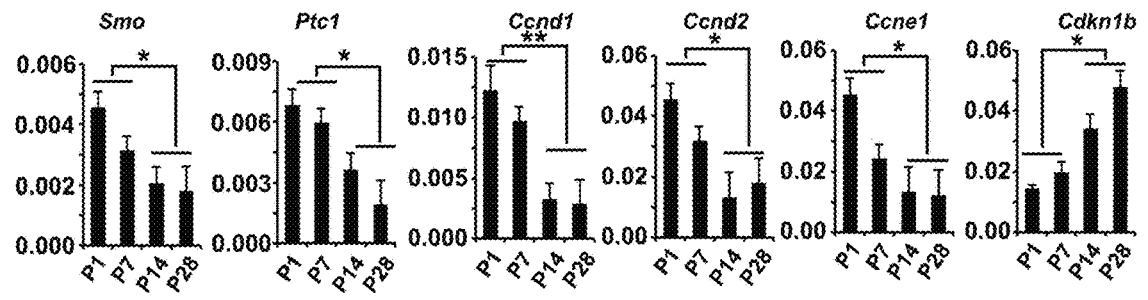
*Fig. 2A*
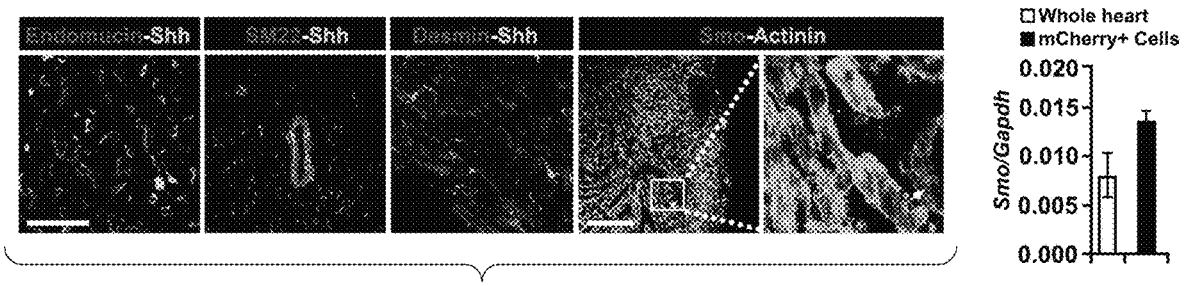
*Fig. 2B*  *Fig. 2C*
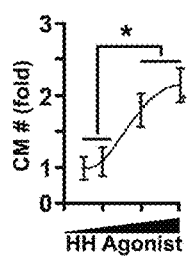 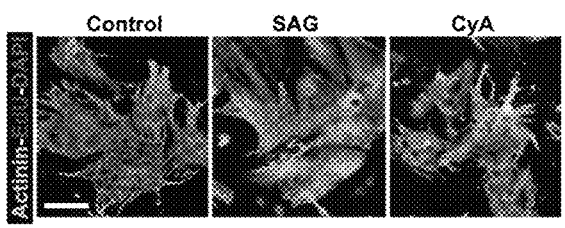 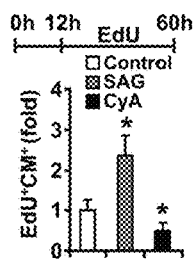
*Fig. 2D*  *Fig. 2E*  *Fig. 2F*
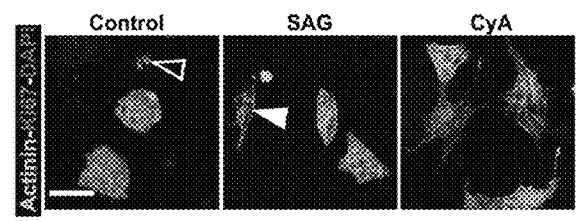
*Fig. 2G*

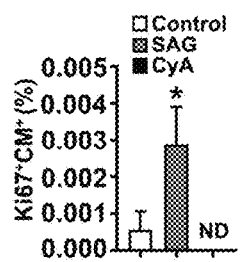  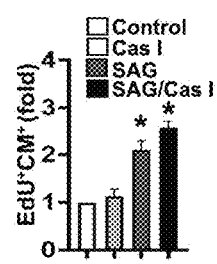
Fig. 2H    Fig. 2I    Fig. 2J
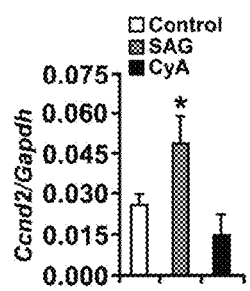 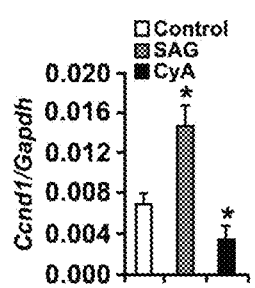 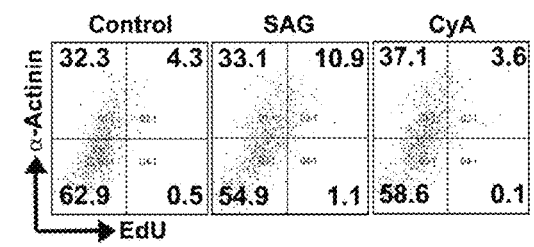
Fig. 2K    Fig. 2L    Fig. 2M
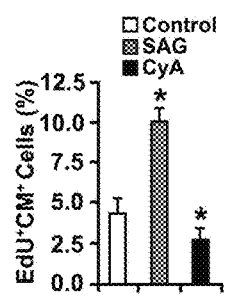
Fig. 2N

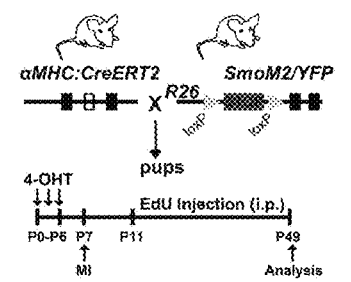
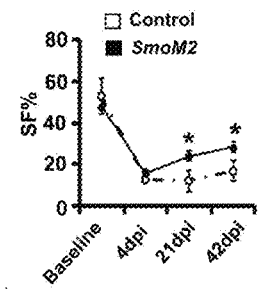
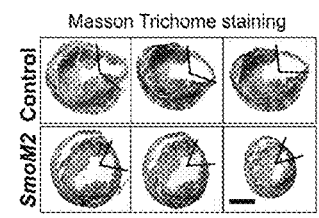
*Fig.6A*  *Fig.6B*  *Fig.6C*
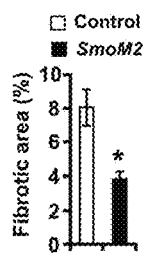
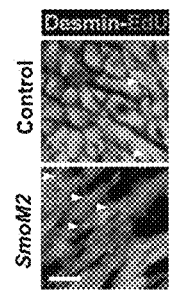
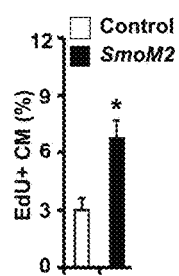
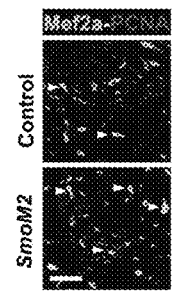
*Fig.6D*  *Fig.6E*  *Fig.6F*  *Fig.6G*
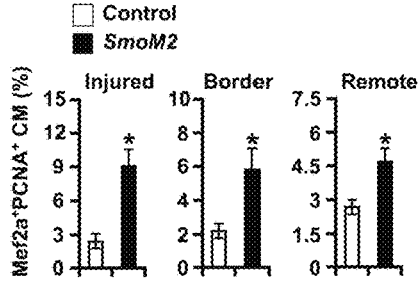
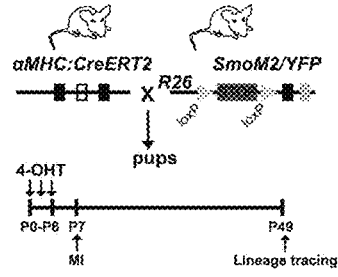
*Fig.6H*  *Fig.6I*
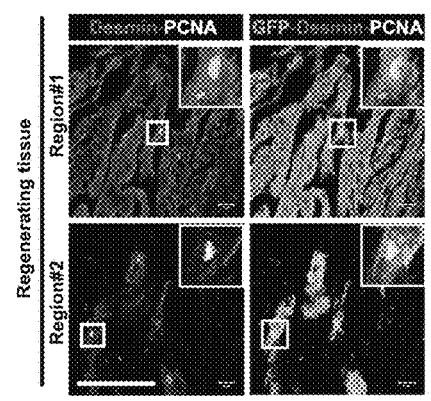
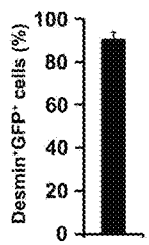
*Fig.6J*  *Fig.6K*

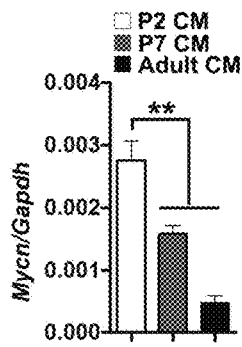
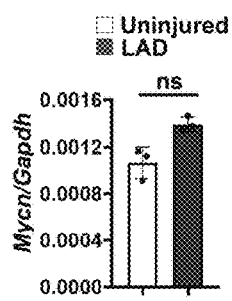
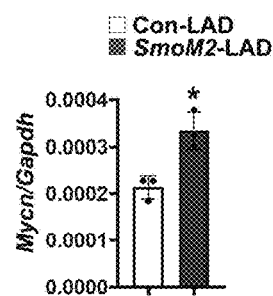
*Fig. 9A*  *Fig. 9B*  *Fig. 9C*
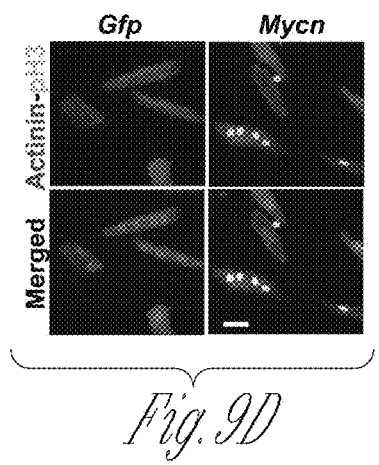
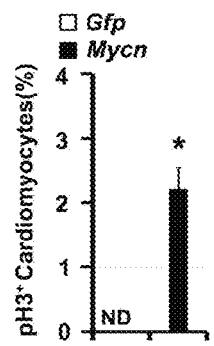
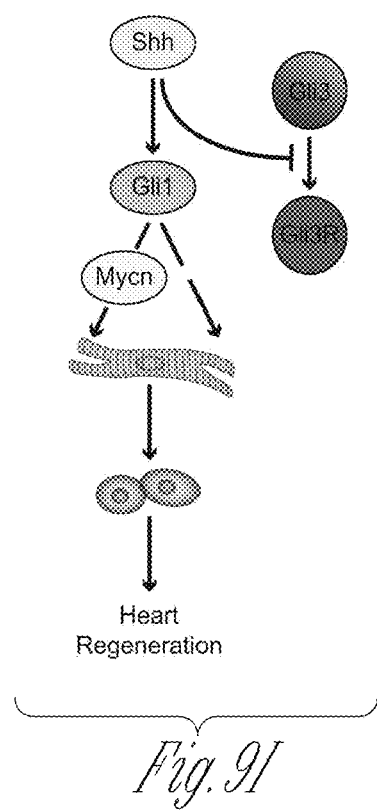
*Fig. 9D*  *Fig. 9E*  *Fig. 9I*
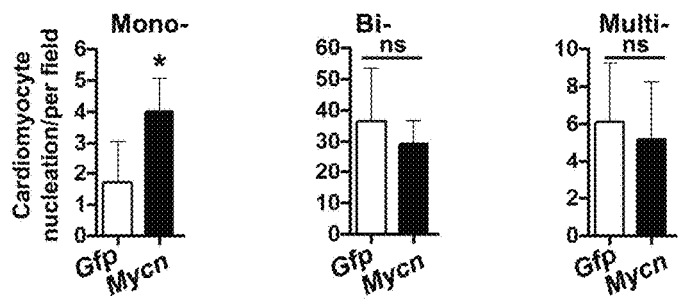
*Fig. 9F*  *Fig. 9G*  *Fig. 9H*

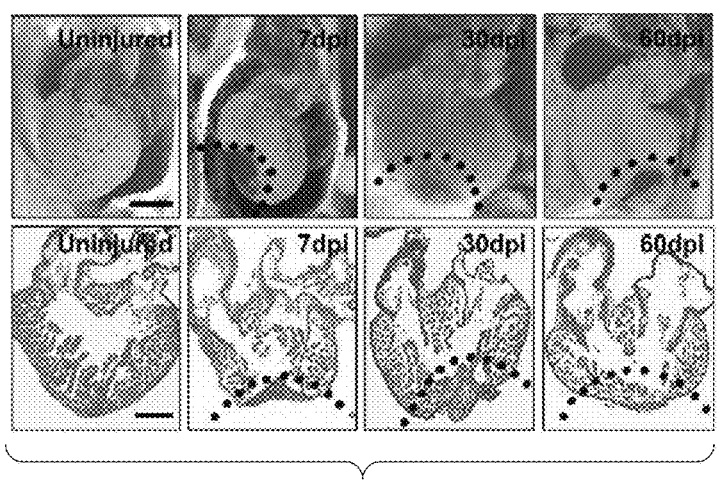
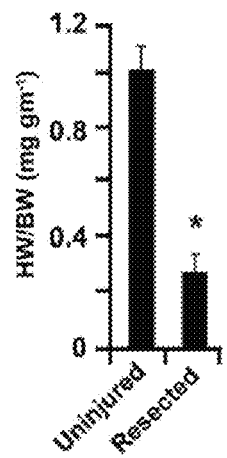
Fig. 10A
Fig. 10B
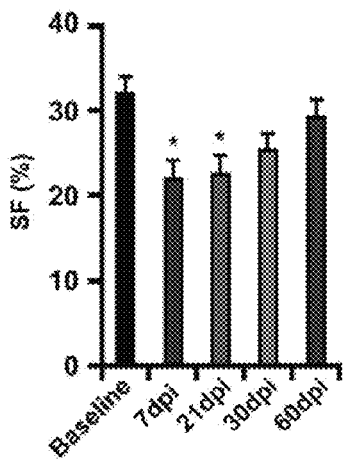
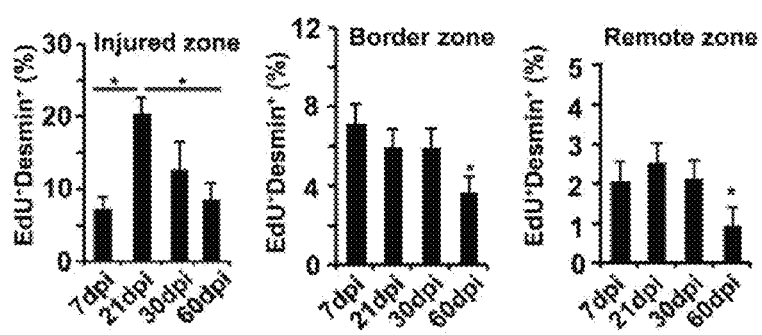
Fig. 10C
Fig. 10D
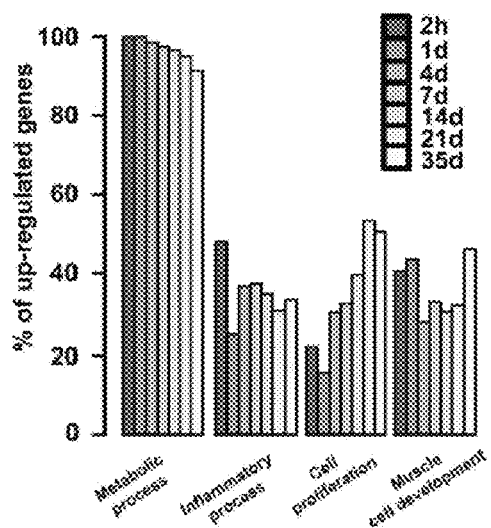
Fig. 10E

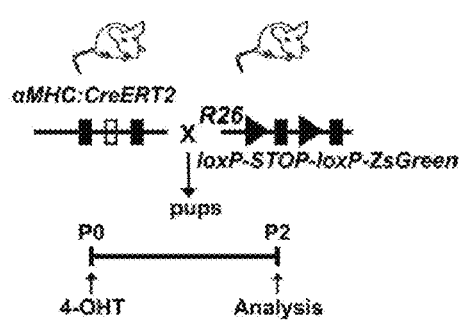
*Fig. 13A*
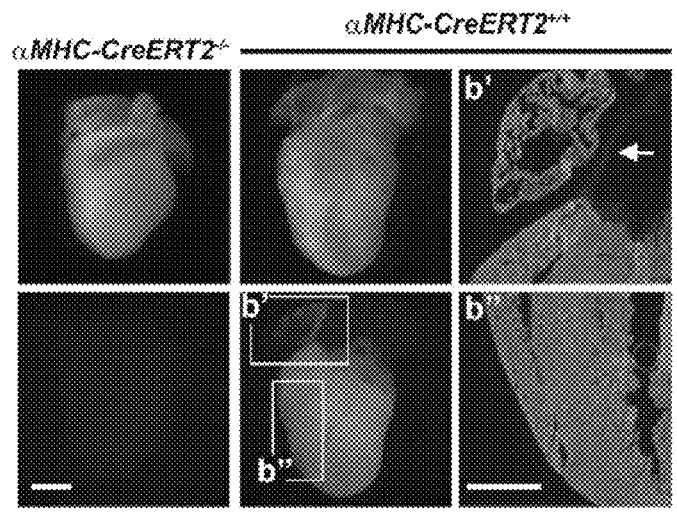
*Fig. 13B*
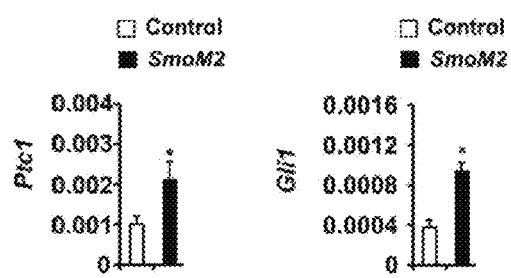
*Fig. 13C*   *Fig. 13D*   *Fig. 13E*   *Fig. 13F*
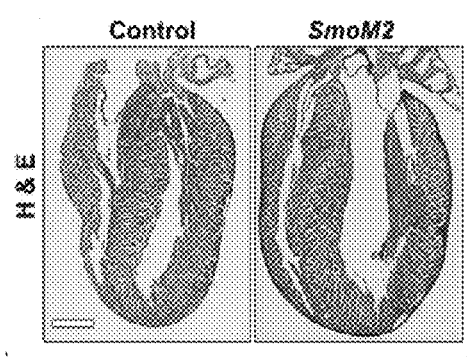
*Fig. 13G*
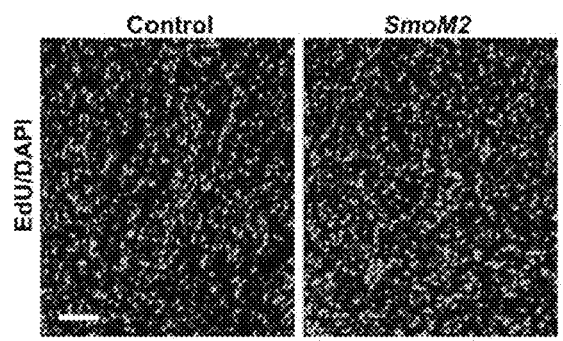
*Fig. 13H*
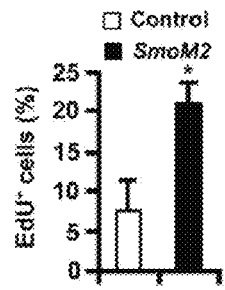
*Fig. 13I*

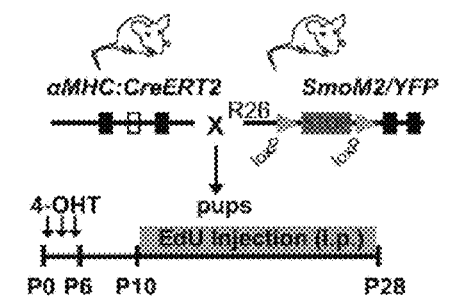
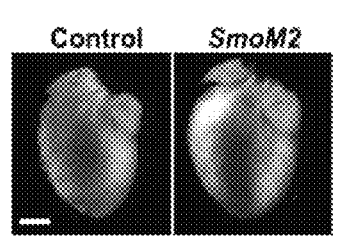
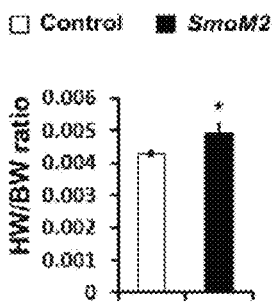
*Fig. 14A*  *Fig. 14B*  *Fig. 14C*
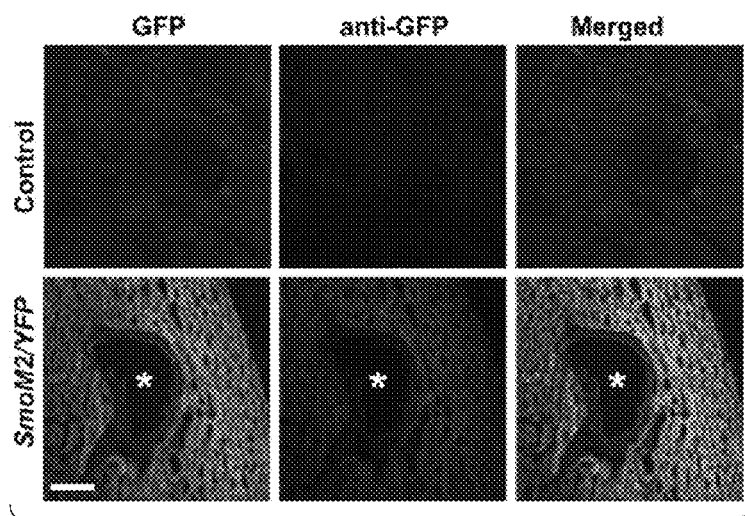
*Fig. 14D*
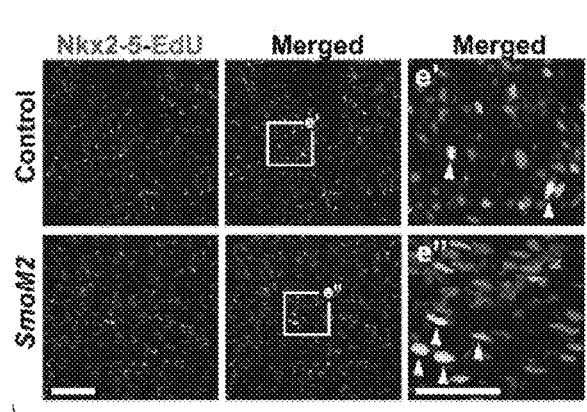
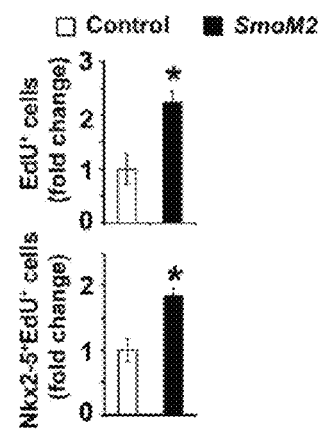
*Fig. 14E*  *Fig. 14F*

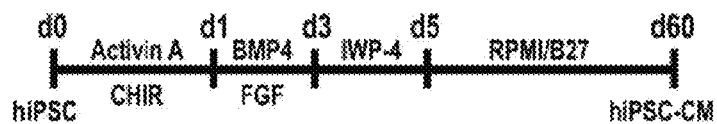
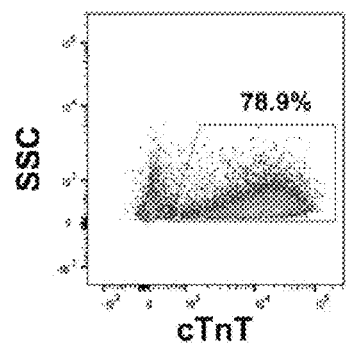
Fig.16A  Fig.16B
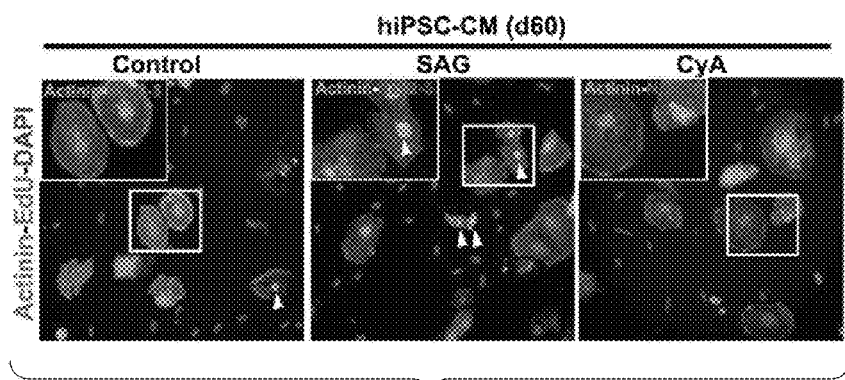
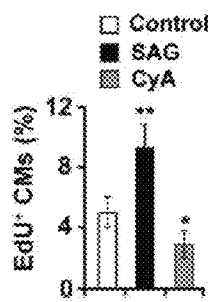
Fig.16C  Fig.16D
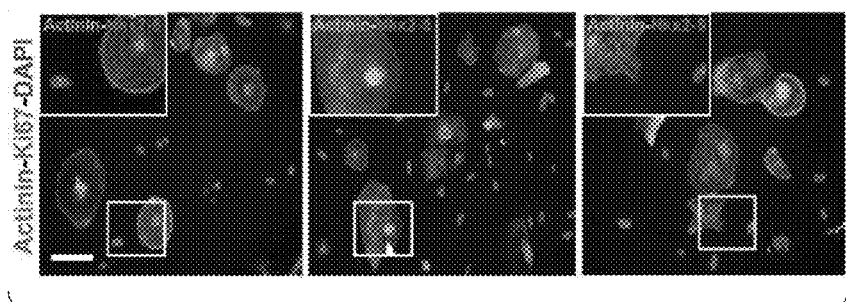
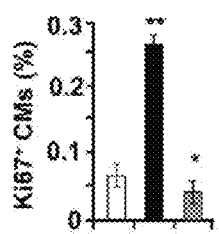
Fig.16E  Fig.16F Gli1 ChIPseq data analysis based on binding motif proximity, heart expression and their functions.

| refseq genome | entrezgene | is.cell.cycle | proli | dist score | Ht exp | HH target | Total Score |
|---|---|---|---|---|---|---|---|
| NM_080554 | Mycn | TRUE | 1 | 0.356 | 1 | 1 | 3.356 |
| NM_001042653 | Id3 | TRUE | 1 | 0.350 | 1 | 1 | 3.350 |
| NM_007836 | Hexim1 | TRUE | 1 | 0.328 | 1 | 1 | 3.328 |
| NM_023873 | Rara | TRUE | 1 | 0.272 | 1 | 1 | 3.272 |
| NM_008957 | Gipc1 | TRUE | 1 | 0.132 | 1 | 1 | 3.132 |
| NM_008957 | Htra2 | TRUE | 1 | 0.076 | 1 | 1 | 3.076 |
| NM_178884 | Dicer1 | TRUE | 1 | 0.02 | 1 | 1 | 3.02 |
| NM_009832 | Psmd11 | TRUE | 1 | 1 | 0 | 1 | 3 |
| NM_008321 | Ensa | TRUE | 1 | 0.972 | 0 | 1 | 2.972 |
| NM_010817 | Dhcr24 | TRUE | 1 | 0.468 | 0.5 | 1 | 2.968 |
| NM_008709 | Ccnk | TRUE | 1 | 0.944 | 0.5 | 0.5 | 2.944 |
| NM_138753 | Wdr6 | TRUE | 1 | 0.916 | 0 | 1 | 2.916 |
| NM_009024 | Hjurp | TRUE | 1 | 0.888 | 0 | 1 | 2.888 |
| NM_018771 | Hjurp | TRUE | 1 | 0.86 | 0 | 1 | 2.86 |
| NM_019752 | Tpd52l1 | TRUE | 1 | 0.832 | 0 | 1 | 2.832 |
| NM_148948 | Oip5 | TRUE | 1 | 0.804 | 0 | 1 | 2.804 |
| NM_178616 | Oip5 | TRUE | 1 | 0.776 | 0 | 1 | 2.776 |
| NM_001026212 | Oip5 | TRUE | 1 | 0.748 | 0 | 1 | 2.748 |
| NM_053272 | Dynll1 | TRUE | 1 | 0.72 | 0 | 1 | 2.72 |
| NM_008957 | Psmd7 | TRUE | 1 | 0.216 | 0.5 | 1 | 2.716 |
| NM_031392 | Smpd3 | TRUE | 1 | 0.692 | 0 | 1 | 2.692 |
| NM_008957 | Pds5b | TRUE | 1 | 0.188 | 0.5 | 1 | 2.688 |
| NM_172505 | Ptch1 | TRUE | 1 | 0.664 | 1 | 0 | 2.664 |
| NM_172505 | Psmd5 | TRUE | 1 | 0.636 | 0 | 1 | 2.636 |
| NM_009413 | Gadd45a | TRUE | 1 | 0.608 | 0 | 1 | 2.608 |
| NM_001042653 | Ptch1 | TRUE | 1 | 0.58 | 1 | 0 | 2.58 |
| NM_001042653 | Cep70 | TRUE | 1 | 0.524 | 0 | 1 | 2.524 |
| NM_019682 | Ptch1 | TRUE | 1 | 0.496 | 1 | 0 | 2.496 |
| NM_021491 | Ptch1 | TRUE | 1 | 0.44 | 1 | 0 | 2.44 |
| NM_175310 | Ptch1 | TRUE | 1 | 0.412 | 1 | 0 | 2.412 |
| NM_008957 | Ptch1 | TRUE | 1 | 0.384 | 1 | 0 | 2.384 |
| NM_008957 | Ptch1 | TRUE | 1 | 0.3 | 1 | 0 | 2.3 |
| NM_008957 | Ptch1 | TRUE | 1 | 0.244 | 1 | 0 | 2.244 |
| NM_008957 | Ptch1 | TRUE | 1 | 0.16 | 1 | 0 | 2.16 |
| NM_008957 | Dusp3 | TRUE | 1 | 0.104 | 0 | 1 | 2.104 |
| NM_028207 | Obsl1 | TRUE | 1 | 0.048 | 0 | 1 | 2.048 |

Fig. 19

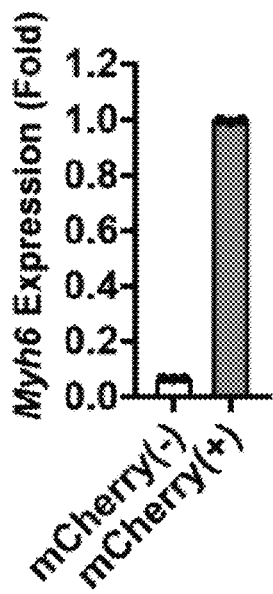
*Fig.22A*
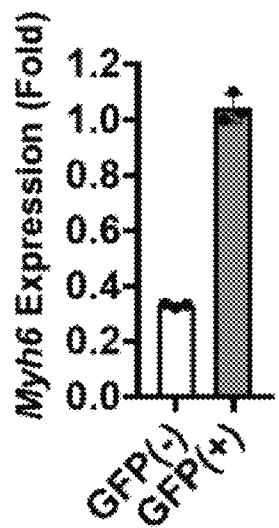
*Fig.22B*
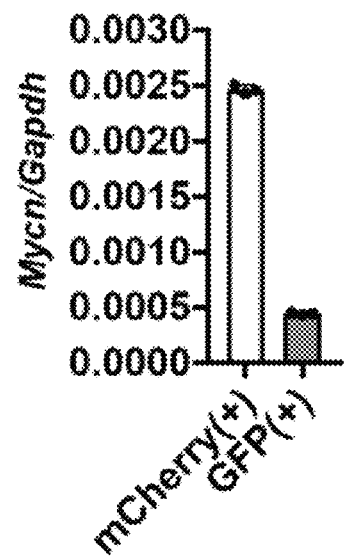
*Fig.22C*
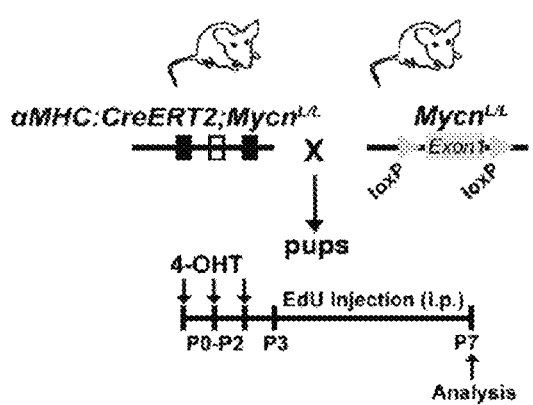
*Fig.23A*
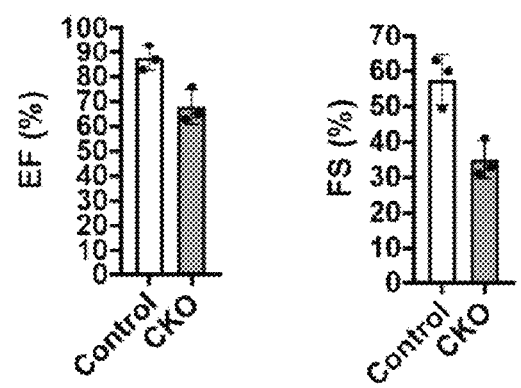
*Fig.23B*     *Fig.23C*

METHODS TO ENHANCE MYOCARDIAL REGENERATION AND/OR REPAIR

CROSS-REFERENCE TO RELATED APPLICATIONS

This application claims the benefit of the filing date of U.S. application No. 62/702,743, filed on Jul. 24, 2018, the disclosure of which is incorporated by reference herein.

BACKGROUND

In contrast to mammals, lower vertebrates such as the adult newt and zebrafish can achieve complete heart regeneration following injury by activating developmental regulatory networks (Singh et al., 2010; Poss et al., 2002; Witman et al., 2011: Singh et al., 2015; Singh et al., 2012). In these organisms, adult cardiomyocytes undergo dedifferentiation to re-enter the cell cycle and, ultimately, differentiation to facilitate tissue regeneration (Kikuchi et al., 2010; Jopling et al., 2010). Using these model organisms, studies have defined the activation of signaling pathways including: FGF, Notch, and BMP signals. However, little is known whether these same factors promote cardiomyocyte proliferation in mammals (Kawakami et al., 2006; Lee et al., 2005). Recently, Aguirre et al. (2014) have shown that activation of a conserved microRNA pathway in the injured zebrafish heart can promote mammalian heart regeneration. While these findings support the existence of conserved regenerative programs, additional studies are needed to define and activate the dormant pathways in mammals.

The neonatal mammalian heart harbors a tremendous potential to promote cardiomyocyte proliferation to facilitate repair and/or regeneration. In the neonatal mouse, the cardiomyocyte proliferative capacity diminishes rapidly within a one-week period following birth (Porrello et al., 2011; Xin et al., 2013; van Amerongen et al., 2009). In contrast, only limited cardiomyocyte turnover occurs in the adult mammalian heart, a capacity that is insufficient to repair or regenerate the injured heart (Bergmann et al. 2009; Senyo et al., 2013). Therefore, efforts have focused on the role of pathways and factors that promote cardiomyocyte proliferation and tissue regeneration in the adult mammalian heart that can prevent the progression of heart failure and premature death following cardiac injury.

Transcriptional networks and signaling pathways that govern embryonic heart development have received intense interest (Xin et al., 2013; Rasmussen et al., 2011; Ferdus et al., 2009; Singh et al., 2015; Koyano-Nakagawa et al., 2012; Gong et al., 2017; Singh et al., 2017). These networks and pathways likely serve as a platform for cardiac regeneration following injury. Studies focused on hedgehog (HH) signaling support the role of this pathway during cardiovascular development in mammals (Zhang et al., 2001). Deletion of either Smo ($Smo^{-/-}$) or Ptc1 ($Ptc1^{-/-}$), or double knockouts of Shh;Ihh ($Shh^{-/-};Ihh^{-/-}$) results in embryonic lethality due to cardiovascular defects (Zhang et al., 2001). In addition, the hedgehog downstream effectors, Gli1, Gli2, and Gli3, function in a redundant and reciprocal fashion to modulate hedgehog activity in a context-dependent fashion during development. While the role of HH signaling is described in cardiac development, its role as a regulator of cardiomyocyte proliferation during heart regeneration remains unknown.

SUMMARY

As described herein below, newt, mouse, and human heart models were used to identify regulators of cardiomyocyte proliferation and regeneration. An evolutionary conserved role for HH signaling in the postnatal heart following injury was identified. Using pharmacological inhibitors, bioinformatics, genetic gain- and loss-of-function strategies, a reciprocal, functional, modulatory effect on the proliferative program in cardiomyocytes was demonstrated. Mechanistically, a HH-Gli1-Mycn gene regulatory network regulates cardiomyocyte proliferation and promotes heart regeneration.

The disclosure provides a method to enhance repair or regeneration of a mammalian heart. The method includes administering to a mammal in need thereof a composition comprising an effective amount of an agent(s) that elevates levels of Smo, Ptc1, Shh, Ihh, Dhh, Gli1, Gli2, or Mycn. In one embodiment, the mammal is a human. In one embodiment, the agent comprises nucleic acid that encodes one or more of Smo, Ptc1, Shh, Ihh, Dhh, Gli1, Gli2, or Mycn, e.g., the nucleic acid is in a viral vector or mammalian cells such as genetically modified mammalian cells. In one embodiment, the nucleic acid encodes a polypeptide having at least 80%, 82%, 85%, 88%, 90%, 92%, 94%, 95%, 96%, 97%, 98% or 99% amino acid sequence identity to a polypeptide comprising one of SEQ ID Nos. 1-5 or 12-15. In one embodiment, the nucleic acid comprises a sequence having at least 80%, 82%, 85%, 88%, 90%, 92%, 94%, 95%, 96%, 97%, 98% or 99% nucleic acid sequence identity to a one of SEQ ID Nos. 6-11. In one embodiment, the genome of the genetically altered cells is augmented with exogenously introduced nucleic acid. In one embodiment, the genome of the genetically altered cells is modified with exogenously introduced nucleic acid. In one embodiment, the agent comprises human cells such as human cardiomyocytes. In one embodiment, the agent comprises human stem cells. In one embodiment the cells are human endothelial cells or vascular cells. In one embodiment, the cells are autologous cells. In one embodiment, the cells are allogeneic cells. In one embodiment, the cells are xenogeneic cells, e.g., pig cells. In one embodiment, the agent is not administered subepicardially. In one embodiment, the agent is not a plasmid. In one embodiment, the agent is not injected into the vasculature of the heart, e.g., a plasmid is not injected subepicardially. In one embodiment, the agent comprises a small molecule, e.g., an organic molecule having a molecular weight of less than about 900 Daltons. In one embodiment, the agent comprises one or more of Smo, Ptc1, Shh, Ihh, Dhh, Gli1, Gli2, or Mycn. In one embodiment, the agent comprises a SHG agonist, e.g., SAG or an analog thereof. In one embodiment, the agent comprises purmorphamin or an analog thereof, e.g., disclosed in Lee et al. (*Mol. Cells,* 26:380 (2008) or in Kim et al. (*Gene & Genomics.* 3:261 (2009), the disclosure of which are incorporated by reference herein), Smoothened agonist, 20(S) hydroxycholesterol, or GSA10. In one embodiment, a recombinant adenovirus, adeno-associated virus, lentivirus, retrovirus, sendaivirus or herpesvirus comprises the nucleic acid. In one embodiment, the amount enhances cardiomyocyte regeneration. In one embodiment, the amount enhances neovascularization. In one embodiment, the amount enhances ejection fraction. In one embodiment, the mammal has cardiovascular disease including heart failure. In one embodiment, the amount reduces fibrosis. In one embodiment, the amount enhances cardiomyocyte proliferation. In one embodiment, the amount alters the left ventricular chamber dimension, e.g., as measured by cardiac MRI and/or echocardiography. In one embodiment, the mammal has a cardiac injury. In one embodiment, the amount is administered after a myocardial infarction. In one embodiment, the agent is administered to the heart. In one embodiment the agent is administered via the coronary arteries. In one embodiment, the agent is systemically administered.

An agent(s) that elevates levels of Smo, Ptc1, Shh, Ihh, Dhh, Gli1, Gli2, or Mycn may also be employed to expand cells in vitro, e.g., induced pluripotent stem cell derived cardiomyocytes, which in turn are useful for drug studies, toxicology studies and as a source for cell therapy including but not limited to repopulation of scaffolds including a decellularized heart or direct deliver to patients.

BRIEF DESCRIPTION OF FIGURES

FIGS. 2A-2N. HH signaling regulates proliferation in mouse neonatal cardiomyocytes. (A) qPCR analysis of Smo, Ptc1, Ccnd1, Ccnd2, Ccne1 and Cdkn1b (p27) transcripts using RNA isolated from P1-P28 mouse heart tissue (n=3 for each time point). (B) Immunostaining of Shh and Smo proteins with Endomucin (endothelial), SM22 (smooth muscle), Desmin (cardiomyocytes) and α-Actinin (cardiomyocytes) in P1 mouse heart sections. The boxed region is magnified in the right panel. The white arrow indicates the staining of Smo in the vascular structures. Note the punctate staining of Smo in the cardiomyocytes. (C) qPCR analysis for Smoothened transcripts from using RNA isolated from whole heart and FACS-sorted αMHC-mCherry$^+$ cells (a transgenic cardiomyocyte specific promoter driving mCherry expression) from P1-P2 pooled hearts. (d) Quantitative analysis of cultured neonatal cardiomyocytes following treatment with various concentration of SAG. (E,F) Immunohistochemical images (E) and quantification (F) of α-Actinin$^+$-EdU$^+$ isolated neonatal cardiomyocytes following exposure to control (white bar), SAG (grey bar) or CyA (black bar) and pulsed with EdU. Quantitative analysis represents the counting of four different fields at 10× from four replicates (n=2000 cardiomyocytes for each condition). (G,H) Immunohistochemical images (G) and quantification (H) of α-Actinin$^+$-Ki67$^+$ isolated neonatal cardiomyocytes following exposure to control (white bar), SAG (grey bar) or CyA (black bar). Quantitative analysis represents the counting of three different fields at 10× from three replicates (n=2000 cardiomyocytes for each condition). Open arrowhead indicate non-cardiomyocytes and closed arrowhead cardiomyocyte positive for Ki67 protein. (I) Live/Dead assay using the isolated neonatal cardiomyocytes following exposure to control (white bar) and SAG (grey bar). Quantitative analysis represents the counting of three different fields at 10× from three replicates. (J) Quantification of α-Actinin$^+$-EdU$^+$ isolated neonatal cardiomyocytes following exposure to DMSO (Control), pan-caspase inhibitor (Cas I), SAG and (SAG+Cas I) for 48 h period. Quantitative analysis represents the counting of eight different fields at 10× from three replicates. (K,L) qPCR analysis for Ccnd2 and Ccnd1 transcripts from isolated neonatal cardiomyocytes exposed to DMSO, SAG or CyA (n=3). (M,N) FACS analysis (M) and quantification (N) for α-Actinin$^+$-EdU$^+$ cardiomyocytes in control (white bar), SAG (grey bars) and CyA (black bars) treated conditions. Quantification involved the analysis of cardiomyocytes (n=30,000) from three replicates. Data are presented as mean±SEM (*p<0.05; **p<0.01) (see also FIG. 12) and scale bars=100 μm.

FIGS. 6A-6K. Activated Smoothened (SmoM2) augments heart regeneration by promoting proliferation of pre-existing cardiomyocytes during the non-regenerative period. (A) Schematic outlining the experimental design for Smo activation (SmoM2) and cardiac regeneration analysis following myocardial injury. (B) Time series echocardiographic measurement of shortening fraction (SF %) of control and SmoM2 mice following MI (n=4 per group). (C,D) Masson trichrome staining (C) and fibrotic area quantification (D) of representative heart sections at 42 days post injury from control and SmoM2 hearts (n=4 for each group). (E,F) Immunostaining (E) and quantification (F) of Desmin$^+$-EdU$^+$ cardiomyocytes in control and SmoM2 hearts. Arrowheads indicate EdU$^+$ labeled cardiomyocytes. (G,H) Immunostaining (G) and quantification (H) of Mef2a$^+$-PCNA$^+$ cardiomyocytes in injured, border and remote areas from control and SmoM2 hearts (n=3 for each group). Arrowheads indicate PCNA$^+$-cardiomyocytes. Quantitative analysis represents counting three random fields at 20× magnification from three biological replicates. (I) Schematic outlining the lineage tracing experiment to examine the impact of the activation of HH signaling on the pre-existing cardiomyocytes following myocardial injury. (J,K) Immunostaining (J) and quantification (K) of Desmin$^+$-PCNA$^+$-GFP$^+$ cardiomyocytes in control and SmoM2 hearts at 42 days post-MI. The boxed region is further magnified and shown in the right corner of the images. Data are presented as mean±SEM (*p<0.05) (see also FIG. 15) and scale bars=100 μm (Panel C) and 200 μm (Panels E,G,J).

FIGS. 9A-9I. Mycn network recapitulates HH signaling mediated adult cardiomyocyte proliferation. (A) qPCR analysis of Mycn transcripts using RNA obtained from isolated cardiomyocytes at P2, P7 and P60 mouse hearts (n=3). (B) qPCR analysis of Mycn transcripts using RNA obtained from adult uninjured and injured heart tissue at 7 days post-MI. (C) qPCR analysis of Mycn transcripts using RNA obtained from control and SmoM2-expressing heart tissue following 7 days post-MI. (D,E) Immunohistochemical images (D) and quantification (E) of α-Actinin$^+$-pH3$^+$ isolated adult cardiomyocytes following transfection with Gfp and Mycn mRNAs at 48 h. Quantitative analysis represents the counting of ten different fields at 10× from three replicates (n=450 cardiomyocytes for each condition). (F-H) Quantitative analysis of the number of mono-, bi-, and multi-nucleated cardio myocytes from Gfp and Mycn mRNAs transfected adult cardiomyocytes. Quantitative analysis represents counting from multiple fields at 10× magnification from three replicates. (I) Schematic model depicting the Shh-Gli1-Mycn regulatory network and cardiomyocyte proliferation. Gli1 transcription factor is induced as a downstream effector of HH signaling upon binding of the Shh morphogen to its membrane receptor. Gli1 and Gli3 function in an antagonistic fashion as Gli1 promotes proliferation whereas Gli3 acts to repress the proliferative program and induces maturation. Activated Gli1 transactivates its downstream target, Mycn, to regulate the proliferative response in cardiomyocytes. Data are presented as mean±SEM (*p<0.05; **p<0.01). Scale bars=200 µm.

FIGS. 10A-10H. Resection injury results in a robust proliferative response and increased expression of HH signals in the regenerating heart. (A) Representative whole mount image analysis (top panels) and histological examination (bottom panels) of the regenerating newt heart (injured region designated with a dotted line) at each time period following injury. (B) HW/BW quantification of the uninjured and the resected portion of the heart (n=10). Note, approximately 25% of the heart was resected. (C) Echocardiographic measurement (SF) of the regenerating newt heart at 7 dpi, 21 dpi, 30 dpi and 60 dpi (n=5 for each time period). (D) Quantitative analysis of Desmin$^+$-EdU$^+$ cardiomyocytes in the injured region of the regenerating newt heart. Quantitative analysis represents counts from four randomly selected fields at 20× magnification from four replicates. (E) Bar graph showing the dysregulated biological processes including metabolic processes, cell migration, cardiac muscle development and cellular proliferation in the regenerating newt heart. (F-H) Schematic outlining the newt heart anatomy (F) and qPCR analysis for shh (G) and ptc-1 (H) transcripts from the bulbous arteriosus [BA (i)], atrium [AT (ii)] and ventricle [ven (iii)] from the regenerating newt heart. Data represent mean±SEM (*p<0.05) and scale bars=500 µm (Panel A, top) and 100 µm (Panel A, bottom).

FIGS. 13A-13I. Cardiac-specific modulation of HH signaling regulates cardiomyocyte proliferation in vivo. (A) Schematic outlining the experimental protocol to examine the specificity of inducible Cre expression within cardiomyocytes in the postnatal heart. (B) Representative whole mount and histological analysis of ZsGreen reporter from control and 4-hydroxy tamoxifen (80 µg/gm) injected mice obtained by crossing αMHC:CreERT2 with Rosa26-ZsGreen mice at P2. The boxed region is magnified in panel B' and B". Note the presence of green fluorescence protein in myocardium (cardiomyocytes) and absence of GFP fluorescence in the noncardiomyocytes (arrow) (i.e. great vessels such as the aorta). (C-E) qPCR analysis of Ptc1, Gli1, and Gli2 transcripts using RNA isolated from control and SmoM2 heart tissue at P7 (n=3 from each group). (F) Quantitative assessment of heart weight and tibia length (HW/TL) ratio of the hearts obtained from control and SmoM2 pups (n=5 for each group). (G) Representative H&E staining of the hearts obtained from control and SmoM2 pups (n=5 for each group). (H,I) EdU staining (H) and quantification (I) of the EdU$^+$ cells from control and SmoM2 hearts. Quantitative analysis represents counting of three randomly selected fields from three biological replicates. Data from panels C, D, E, F and I represent mean±SEM (*p<0.05) and scale bars=200 µm (Panels B', B", B") and 100 µm (Panels G,H).

FIGS. 14A-14F. Induction of HH signaling promotes in vivo cardiomyocyte proliferation in the late juvenile stage of the mouse. (A) Schematic for the experimental protocol to study the activation of HH signaling and EdU labeling in the postnatal heart. EdU (shaded area) was injected intraperitoneally (i.p.) every three days. (B) Representative whole mount heart images obtained from control and SmoM2 pups at P28. (C) Quantitative assessment (HW/BW ratio) of the hearts obtained from control and SmoM2 mice at P28 (n=4 in each group). (D) Representative immunostained images showing the expression of the fluorescent reporter at P28. The asterisk designates the lumen of a muscular artery within the ventricular tissue. Note the absence of GFP expression and staining in the vascular wall. (E,F) Immunostaining (E) and quantification (F) of EdU$^+$ cells (top) as well as Nkx2-5$^+$-EdU$^+$ cardiomyocytes (bottom) in control and SmoM2 hearts. The boxed region is magnified in panel E' and E". The white arrowheads indicate the cardiomyocytes that had undergone a proliferative event within the myocardium. Data from panels C and F represent mean±SEM (*p<0.05) and scale bars=500 μm (Panel B) and 100 μm (Panels D,E).

FIGS. 16A-16F. Induction of HH signals promotes proliferation of d60 hiPSC-CMs. (A) Schematic of hiPSC-derived cardiomyocyte differentiation protocol as described in Dubois et al. (2011). (B) Representative FACS analysis for intracellular cTnT using hiPSC-CMs. (C-F) Immunohistochemical (C,E) and quantification (D,F) of α-Actinin$^+$-EdU$^+$ and α-Actinin$^+$-Ki67$^+$ d60 hiPSC-CMs from control, SAG and CyA treated conditions. The boxed region is further magnified and shown in the left corner of the images. Quantitative analysis represents the counting of four randomly chosen fields from three replicates (n=1935 cardiomyocytes for each condition). Data in panels D and F represent mean±SEM (*p<0.05; **p<0.01) and scale bars=200 μm.

FIG. 19. Gli1ChIPseq data analysis based on binding motif proximity, heart expression and their functions.

FIGS. 22A-22C. qPCR analysis of conditional deletion of Mycn transcripts in the FACS-sorted cardiomyocytes. A) qPCR analysis of Myh6 using FACS-sorted Myh6-mCherry$^-$ (non-cardiomyocytes) and Myh6-mCherry$^+$ (cardiomyocytes) cells. B) qPCR analysis of Myh6 using FACS-sorted zsGreen$^-$ (GFP$^-$) and zsGreen$^+$ (GFP$^+$) cells obtained by crossing αMHC-CreER2;Mycn$^{L/L}$ with Rosa26-zsGreen; Mycn$^{L/L}$ mice at postnatal day 3. C) qPCR analysis of Mycn using FACS-sorted mCherry$^+$ and zsGreen$^+$ (GFP$^+$) cardiomyocytes. Note that the levels of Mycn were robustly reduced in the zsGreen$^+$ cells as compared to mCherry$^+$ cells.

FIGS. 23A-23C. Conditional deletion of Mycn results in functional impairment in the postnatal heart. A) Schematic of cardiomyocyte-specific conditional deletion of the floxed-Mycn allele. B,C) Ejection fraction (EF) and fractional shortening (FS) measurements of the control and CKO revealed impaired cardiac function following cardiomyocyte-specific deletion of Mycn allele (n=3 per group). Control mice were not injected with 4-hydroxytamoxifen.

DETAILED DESCRIPTION

Figure 1A:
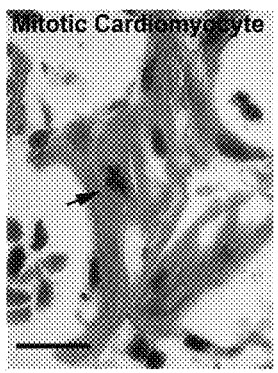
FIGS. 1A-1J, HH signaling is essential for heart regeneration. (A) Histological examination of the regenerating newt heart showing mitotic cardiomyocyte in the injured tissue. (B.C) Immunohistochemical (B) and quantitative analysis of the total EdU$^+$ cells (C) in the regenerating newt heart. The white arrowheads indicate the proliferating cardiomyocytes within the myocardium at specified time periods following injury. The boxed regions are magnified in the lower panels. Quantitative analysis represents counts from four randomly selected fields at 20× magnification from four replicates at each time period. (D) Gene set enrichment analysis using Bootstrap tools from regenerating newt heart tissue at the designated time periods post-injury. (E,F) qPCR analysis for shh and ptc-1 transcripts during cardiac regeneration in the newt (n=4). (G) Schematic (top) of experimental protocol and whole mount images of the regenerating heart obtained from control and CyA-treated newts at 7 dpi and 30 dpi (n=6 for each group). The dotted line represents the injured region of the heart. (H) Masson Trichrome staining of the regenerating hearts from control and CyA-treated newts at 7 dpi and 30 dpi (n=6 for each group). The dotted line represents the injured region of the heart. (I,J) Immunohistochemical staining (I) and quantification (J) of Desmin$^+$-EdU$^+$ cardiomyocytes in the regenerating heart from control and CyA-treated newts at the designated time periods following injury (n=6). The dotted line in panel i represents the injured region of the heart and the tissue in the boxed region is magnified in I' and iI' panels. White arrowheads indicate the EdU$^+$-cardiomyocytes. Data are presented as mean±SEM (*p<0.05; **p<0.01) (see also FIG. 10 and FIG. 11) and scale bars=200 μm (Panels A, B, H, I) and 500 μm (Panel G).

The mammalian heart has a limited regenerative capacity and typically progresses to heart failure following injury. Here, a hedgehog (HH)-Gli1-Mycn regulatory cascade was shown to be involved in cardiomyocyte proliferation and heart regeneration from amphibians to mammals. Using a genome-wide screen, HH signaling was shown to be essential for heart regeneration in the injured newt. Next, pharmacological and genetic loss- and gain-of-function of HH signaling in cardiomyocyte-specific fashion demonstrated the requirement for HH signaling in the neonatal, adolescent, and adult mouse heart regeneration, and in the proliferation of terminally differentiated hiPSC-derived cardiomyocytes. Pan-caspase inhibition studies showed a pro-proliferative impact of HH signaling with no cyto-protective effect on the cultured cardiomyocytes. Fate-mapping and molecular biological studies revealed that HH signaling, via a novel HH-Gli1-Mycn regulatory network, contributed to heart regeneration by inducing proliferation of pre-existing cardiomyocytes and not by de novo cardiomyogenesis. Further, Mycn mRNA transfection experiments recapitulated the effects of HH signaling activation phenotype during adult cardiomyocyte proliferation. These studies define an evolutionarily conserved previously undescribed function of HH signaling that may serve as a platform for human regenerative therapies.

Thus, the agents described herein, e.g., small molecules including proteins or gene therapy vectors, may be employed to prevent, inhibit or treat any disorder or disease of the heart, e.g., myocardial infarction, ischemic injury, chronic obstructive heart disease, heart failure, myocarditis, cardiomyopathy, congenital heart defect or any disease that results in cardiac dysfunction.

Vectors for Delivery

Exemplary delivery vectors include, for example, viral vectors, microparticles, nanoparticles, nanocrystals, liposomes and other lipid-containing complexes, and other macromolecular complexes capable of mediating delivery of a gene or protein or non-protein small molecule to a host cell, e.g., to provide for recombinant expression of a polypeptide encoded by the gene. Vectors can also comprise other components or functionalities that further modulate gene delivery and/or gene expression, or that otherwise provide beneficial properties. Such other components include, for example, components that influence binding or targeting to cells (including components that mediate cell-type or tissue-specific binding); components that influence uptake of the vector by the cell; components that influence localization of the transferred gene within the cell after uptake (such as agents mediating nuclear localization); and components that influence expression of the gene. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities. Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., WO 92/08796; and WO 94/28143). Such marker genes can provide an added measure of control that can be advantageous in gene therapy contexts. A large variety of such vectors are known in the art and are generally available.

Vectors within the scope of the disclosure include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, sendaivirus, papilloma virus, or adeno-associated virus, including viral and non-viral vectors, or proteins, which are present in liposomes, e.g., neutral or cationic liposomes, such as DOSPA/DOPE, DOGS/DOPE or DMRIE/DOPE liposomes, and/or associated with other molecules such as DNA-anti-DNA antibody-cationic lipid (DOTMA/DOPE) complexes. Exemplary gene viral vectors are described below. Vectors may be administered via any route including, but not limited to, intramuscular, buccal, rectal, intravenous or intracoronary administration, e.g., using an intracoronary catheter or catheter based endocardial system, and transfer to cells may be enhanced using electroporation and/or iontophoresis. In one embodiment, vectors are locally administered.

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that include human immunodeficiency virus and feline immunodeficiency virus. However, unlike retroviruses that only infect dividing cells, lentiviruses can infect both dividing and nondividing cells. Although lentiviruses have specific tropisms, pseudotyping the viral envelope with vesicular stomatitis virus yields virus with a broader range.

Adenoviral Vectors

Adenoviral vectors may be rendered replication-incompetent by deleting the early (E1A and E1B) genes responsible for viral gene expression from the genome and are stably maintained into the host cells in an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing tissue specific promoters. In addition, adenoviral vectors can be produced at very high titers, allowing efficient gene transfer with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adeno-virus, adeno-associated virus vectors also have the capability to infect replicating and nonreplicating cells and are believed to be nonpathogenic to humans. Moreover, they appear promising for sustained cardiac gene transfer.

Herpesvirus/Amplicon

Herpes simplex virus 1 (HSV-1) has a number of important characteristics that make it a gene delivery vector in vivo. There are two types of HSV-1-based vectors: 1) those produced by inserting the exogenous genes into a backbone virus genome, and 2) HSV amplicon virions that are produced by inserting the exogenous gene into an amplicon plasmid that is subsequently replicated and then packaged into virion particles. HSV-1 can infect a wide variety of cells, both dividing and nondividing, but has obviously strong tropism towards nerve cells. It has a very large genome size and can accommodate very large transgenes (>35 kb). Herpesvirus vectors are particularly useful for delivery of large genes.

Polymer Delivery Vehicles

In one embodiment, the delivery vehicle is a naturally occurring polymer, e.g., formed of materials including but not limited to albumin, collagen, fibrin, alginate, extracellular matrix (ECM), e.g., xenogeneic ECM, hyaluronan (hyaluronic acid), chitosan, gelatin, keratin, potato starch hydrolyzed for use in electrophoresis, or agar-agar (agarose). In one embodiment, the delivery vehicle comprises a hydrogel. In one embodiment, the composition comprises a naturally occurring polymer. Table 1 provides exemplary materials for delivery vehicles that are formed of naturally occurring polymers and materials for particles.

TABLE 1

| Particle class | Materials |
| --- | --- |
| Natural materials or derivatives | Chitosan |
| | Dextran |
| | Gelatine |
| | Albumin |
| | Alginates |
| | Liposomes |
| | Starch |

TABLE 1-continued

| Particle class | Materials |
| --- | --- |
| Polymer carriers | Polylactic acid<br>Poly(cyano)acrylates<br>Polyethyleneimine<br>Block copolymers<br>Polycaprolactone |

An exemplary polycaprolactone is methoxy poly(ethylene glycol)/poly(epsilon caprolactone). An exemplary poly lactic acid is poly(D,L-lactic-co-glycolic) acid (PLGA).

Some examples of materials for particle formation include but are not limited to agar acrylic polymers, polyacrylic acid, poly acryl methacrylate, gelatin, poly(lactic acid), pectin (poly glycolic acid), cellulose derivatives, cellulose acetate phthalate, nitrate, ethyl cellulose, hydroxyl ethyl cellulose, hydroxypropylcellulose, hydroxyl propyl methyl cellulose, hydroxypropylmethylcellulose phthalate, methyl cellulose, sodium carboxymethylcellulose, poly(ortho esters), polyurethanes, poly(ethylene glycol), poly(ethylene vinyl acetate), polydimethylsiloxane, poly(vinyl acetate phthalate), polyvinyl alcohol, polyvinyl pyrrollidone, and shellac. Soluble starch and its derivatives for particle preparation include amylodextrin, amylopectin and carboxy methyl starch.

In one embodiment, the polymers in the nanoparticles or microparticles are biodegradable. Examples of biodegradable polymers useful in particles preparation include synthetic polymers, e.g., polyesters, poly(ortho esters), polyanhydrides, or polyphosphazenes; natural polymers including proteins (e.g., collagen, gelatin, and albumin), or polysaccharides (e.g., starch, dextran, hyaluronic acid, and chitosan). For instance, a biocompatible polymer includes poly (lactic) acid (PLA), poly (glycolic acid) (PLGA). Natural polymers that may be employed in particles (or as the delivery vehicle) include but are not limited to albumin, chitin, starch, collagen, chitosan, dextrin, gelatin, hyaluronic acid, dextran, fibrinogen, alginic acid, casein, fibrin, and polyanhydrides.

In one embodiment, the delivery vehicle is a hydrogel. Hydrogels can be classified as those with chemically cross-linked networks having permanent junctions or those with physical networks having transient junctions arising from polymer chain entanglements or physical interactions, e.g., ionic interactions, hydrogen bonds or hydrophobic interactions. Natural materials useful in hydrogels include natural polymers, which are biocompatible, biodegradable, support cellular activities, and include proteins like fibrin, collagen and gelatin, and polysaccharides like starch, alginate and agarose.

In one embodiment, the delivery vehicle comprises inorganic nanoparticles, e.g., calcium phosphate or silica particles; polymers including but not limited to polylactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or protamine; or poly(β-amino ester), chitosan, PEI-polyethylene glycol, PEI-mannose-dextrose, DOTAP-cholesterol or RNAiMAX.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines. A subset composed of these carbohydrates and four ethyleneamines in the polymer repeat units yielded exceptional delivery efficiency.

In one embodiment, the delivery vehicle comprises polyethyleneimine (PEI), Polyamidoamine (PAMAM), PEI-PEG, PEI-PEG-mannose, dextran-PEI, OVA conjugate, PLGA microparticles, or PLGA microparticles coated with PAMAM.

In one embodiment, the delivery vehicle comprises a cationic lipid, e.g., N-[1-(2,3-dioleoyloxy)propel]-N,N,N-trimethylammonium (DOTMA), 2,3-dioleyloxy-N-[2-spermine carboxamide]ethyl-N,N-dimethyl-1-propanammonium trifluoracetate (DOSPA, Lipofectamine); 1,2-dioleoyl-3-trimethylammonium-propane (DOTAP); N-[1-(2,3-dimyristloxy)propyl]; N,N-dimethyl-N-(2-hydroxyethyl) ammonium bromide (DMRIE), 3-β-[N—(N,N'-dimethylaminoethane) carbamoyl] cholesterol (DC-Chol); dioctadecyl amidoglyceryl spermine (DOGS, Transfectam); or imethyldioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed. In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethyl-ammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, the particles comprise at least one polymeric material. In one embodiment, the polymeric material is biodegradable. In one embodiment, polymeric materials include: silk, elastin, chitin, chitosan, poly(α-hydroxy acids), poly(anhydrides), and poly(orthoesters). In one embodiment, the biodegradable microparticle may comprise polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybiscarboxyphenoxyphenoxy hexone (PCPP) poly[bis (p-carboxypheonoxy) methane] (PCPM), copolymers of SA, CPP and CPM, poly(amino acids), poly(pseudo amino acids), polyphosphazenes, derivatives of poly[(dichloro)phosphazenes] and poly[(organo) phosphazenes], poly-hydroxybutyric acid, or S-caproic acid, polylactide-co-glycolide, polylactic acid, and polyethylene glycol. Polyesters may be employed.

Plasmid DNA Vectors

Plasmid DNA is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of focal transgene expression, has demonstrated significant biologic effects in animal models and appears promising clinically. Furthermore, plasmid DNA is rapidly degraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

In one embodiment, an isolated polynucleotide or vector having that polynucleotide comprises nucleic acid encoding a polypeptide or fusion protein that has substantial identity, e.g., at least 80% or more, e.g., 85%, 87%, 90%, 92%, 95%, 97%, 98%, 99% and up to 100%, amino acid sequence identity to one of SEQ ID NOs. 1-5 or 12-15, or the nucleic acid has substantial identity, e.g., at least 80% or more, e.g., 85%, 87%, 90%, 92%, 95%, 97%, 98%, 99% and up to 100%, nucleic acid sequence identity to one of SEQ ID NOs. 6-11, and may in one embodiment, when administered, promote cardiac growth, regeneration or repair.

An exemplary Smo mRNA sequence is:

```
>NM_176996.4 Mus musculus smoothened, frizzled
class receptor (Smo), mRNA
                                    (SEQ ID NO: 6)
CCAGCTAGAGCAACAAAGGAGCCCGGTAGTCGGCAGGGAGAGCTCAGGGG

GCTGCGGCGCGCTCGCGCGGAGGTGGCTGCTGGGCCGCGGGCTGGCGTGG

GGGCGGAGCCGGGGACCCACTCCCGCACCCCCCCCCCCCCCGGCCGGC

GCCTGGCCTCCATCGAGGGGCTGGGAGTCGGTTTTAATGGTGGGAGAGGG

AATGGGGCTGGAGATCGGGGCCCCGGAGGGGTTCCCAGGGTTGAAGACAGC

TTCGATCTCCAGGCCAGGGAGTCCGGGGTCTGTGCATCCTGGCCCGGGCC

TGCGCTGCTCAACATGGGGCCCGGGTTCCAAAGTTTGCAAAGTTGGGAGT

CGAGGGGCCCGGACGCGCGCGGCGCCTGGCGAAAGCTGGCCCCAGACTTT

CGGGGCGCACCGGTCGCCTAAGTAGCCTCCGCGGCCCCCGGGGTCGTGTG

TGTGGCCAGGGGACTCCGGGGAGCTCCGGGGCGCCTCAGCTTTTGCTGAG

TTGGCTGTTTGGCCATGGCCGCTGGCCGCCCCGTGCGTGGGCCCGAGCTG

GCGCCCCGGAGGCTGCTGCAGTTGCTGCTGCTGGTACTGCTGGGGGGCCC

GGGCCGGGGGGCGGCCTTGAGCGGGAACGTGACCGGGCCTGGGCCTCACA

GCGCCAGCGGGAGCTCGAGGAGGGACGTGCCGGTGACCAGCCCTCCGCCG

CCGCTGCTGAGCCACTGCGGCCGGGCCGCCCACTGCGAGCCTTTGCGCTA

CAACGTGTGCCTGGGCTCGGCGCTGCCCTACGGAGCCACCACCACGCTGC

TGGCTGGGGACTCGGACTCGCAGGAGGAAGCGCACGGCAAGCTCGTGCTC

TGGTCCGGCCTCCGGAATGCCCCCCGCTGCTGGGCAGTGATCCAGCCCCT

GCTGTGTGCTGTCTACATGCCCAAGTGTGAGAATGACCGAGTGGAGTTGC

CCAGCCGTACCCTCTGCCAGGCCACCCGAGGCCCCTGTGCCATTGTGGAG

CGGGAGCGAGGGTGGCCTGACTTTCTGCGTTGCACACCGGACCACTTCCC

TGAAGGCTGCCCAAACGAGGTACAAAACATCAAGTTCAACAGCTCAGGCC

AATGTGAAGCACCCTTGGTGCGAACAGACAACCCCAAGAGCTGGTATGAG

GACGTGGAGGGCTGTGGGATTCAGTGTCAGAACCCGCTGTTCACCGAGGC

CGAGCACCAGGACATGCACAGCTACATCGCAGCCTTCGGGGCGGTCACTG

GTCTCTGCACGCTCTTCACACTGGCCACCTTTGTGGCTGACTGGCGGAAC

TCCAATCGCTACCCTGCGGTTATTCTCTTCTATGTCAATGCGTGTTTCTT

CGTGGGCAGCATTGGCTGGCTGGCCCAGTTCATGGATGGTGCCCGCCGAG

AGATTGTTTGCCGAGCAGATGGCACCATGAGATTTGGGGAGCCCACCTCC

AGTGAGACCCTGTCCTGTGTCATCATCTTTGTCATTGTGTACTATGCCTT

GATGGCTGGAGTAGTCTGGTTCGTGGTCCTCACCTATGCCTGGCACACCT

CCTTCAAAGCCCTGGGCACCACCTACCAGCCTCTCTCGGGCAAGACATCC

TATTTCCACCTGCTCACGTGGTCACTCCCCTTTGTCCTCACGGTGGCAAT

CCTGGCTGTGGCTCAGGTAGATGGAGACTCCGTGAGTGGCATCTGTTTTG

TAGGCTACAAGAACTATCGGTACCGTGCTGGCTTTGTCCTGGCCCCAATT

GGCCTGGTGCTTATTGTGGGAGGCTACTTCCTCATCAGAGGGGTCATGAC

TCTGTTCCCCATCAAGAGCAACCACCCTGGGCTTCTGAGTGAGAAGGCAG

CCAGCAAGATCAACGAGACCATGCTGCGCCTGGGCATTTTTGGCTTCCTG

GCCTTTGGCTTTGTGCTCATCACCTTCAGCTGCCACTTCTATGACTTCTT

CAACCAGGCTGAGTGGGAGCGTAGCTTCCGGGACTATGTGCTATGCCAAG

CCAACGTGACCATCGGGCTGCCTACCAAGAAGCCCATTCCTGACTGTGAG

ATCAAGAATCGGCCCAGCCTCCTGGTGGAGAAGATCAATCTATTTGCCAT

GTTTGGCACTGGCATTGCCATGAGCACCTGGGTCTGGACCAAGGCCACCC

TGCTCATCTGGAGGCGCACCTGGTGCAGGTTGACTGGGCACAGTGATGAT

GAGCCCAAGAGAATCAAGAAGAGCAAGATGATCGCCAAGGCCTTCTCTAA

GCGGCGTGAGCTGCTGCAGAACCCGGGCCAGGAGCTCTCCTTCAGCATGC

ACACTGTCTCCCATGATGGACCTGTTGCGGGTTTGGCTTTTGACCTCAAT

GAACCCTCAGCTGACGTCTCCTCTGCCTGGGCTCAGCATGTCACCAAGAT
```

```
GGTGGCTCGGAGAGGAGCCATATTGCCCCAGGATGTGTCCGTTACCCCTG
TGGCAACTCCAGTGCCACCAGAAGAACAAGCCAACATGTGGCTGGTTGAG
GCAGAGATCTCCCCAGAGTTAGAGAAGCGTTTGGGCCGGAAGAAAAAGCG
GAGGAAGAGGAAGAAGGAGGTGTGCCCCTTGAGGCCAGCCCCTGAGCTTC
ACCACTCTGCCCCTGTTCCTGCCACCAGTGCAGTTCCTCGGCTGCCTCAG
CTGCCTCGGCAGAAGTGCCTGGTAGCTGCAAACGCCTGGGGAACAGGGGA
GTCCTGCCGACAGGGAGCCTGGACTCTAGTCTCCAACCCCTTCTGCCCAG
AGCCTAGTCCCCATCAAGATCCATTTCTCCCTGGTGCCTCAGCCCCCCGG
GTCTGGGCTCAGGGCCGCCTCCAGGGGCTGGATCCATTCATTCCCGCAC
TAACCTAATGGAGGCTGAGATCTTGGATGCAGACTCGGACTTCTGAGCCT
GCAGGGCAGGTCCTAGGATGGGAAAGACAAATGTACACCTTTCTATGGCT
CTTCCTGAGAGCACACCTCTGGGTCTCATCTGACAGAGTCTGTGGGCCAA
GTGTCTGCCTAGAAGAGCTGTGTATGTCTGGCTAGAAGCAGCCAGGCCAT
GGAAACAAGTTGAATACAGCGATTGGTAGGCCTCATGTCAGAATCAGGAC
CCTGCACTTCAGGACCCTTGCTTCTGCCCACCAATCAGAGTCTGACTGGC
AGTGTTAGTCTCCGACAGAGCTTGTACTAGGGCAGGAATGGCAGAGACAG
GGATGATGGTACCCAGAGTGGGCTGTGGTGGTCTGTGAGGTAACCAAGCC
CATGTCTGGCAGATGAGGGCTGTTTGCCCTTTTCTGTGCCAATGAGTGCC
CTTTTCTGGCACTCTCAGACCAAAAGTGTTTATTGTGTCATTTGTCCTTT
GTCTAGGAGAGGACAGGACTCTCTTTTTCCTCTTCCTGGTAGTTGTAATG
ACCACTCCCATAAGGGCTATAACTGTTCTTCACAGGTGGCCCTGCTCAAA
ATACATCCTCTCTTTTCCCGTTCTATCCCTACATTCACATCTCAGTTCCA
CTAGGCAACCTCTTCCTGGTTAGCACCTTAAAACTGCAGTGAGCACACA
CAGACACACACACATACACTCTCACACACACAGACAGGCATGCACACA
CACACACACACACACACACACACACACACCCCTTACTTCTGAGCTCTGTC
TTAAGAGACTACTGGTTCAGCTCCAGGCCTCTGAAAGACATGTTATTTCT
TCCTCACATCCATCCAGTGGGAGGACCCTCTGACTTAAGGGACCACCTT
GGGAAGCTTCTGTAGCTTCAGCCAGGCAAGAAAGCTTCTTCCAACTTCTG
TTTCTGGTGGGAGCGGGGGACTCCCACTTTTTACAATGTCTAGTCATTT
TCATAGTGCCCCACATTCAAGAACCAGACAACAGGATGCCTTAGAAGCTG
GCTGGGTTTTGGGTCAGGGGCTCAGTATGAGAAGAAGAAATATGAACAGC
AAATAAAACATTTTTGTATAAGCTCAT;
``` an exemplary Smo protein sequence is:

(SEQ ID NO: 1)
```
maaarpargp elpllglll1 lllgdpgrga assgnatgpg
prsaggsarr saavtgpppp lshcgraapc eplrynvclg
svlpygatst llagdsdsqe eahgklvlws glrnaprcwa
viqpllcavy mpkcendrve lpsrtlcqat rgpcaivere
rgwpdflrct pdrfpegctn evqnikfnss gqcevplvrt
dnpkswyedv egcgiqcqnp lfteaehqdm hsyiaafgav
tglctlftla tfvadwrnsn rypavilfyv nacffvgsig
wlaqfmdgar reivcradgt mrlgeptsne tlscviifvi
vyyalmagvv wfvvltyawh tsfkalgtty qplsgktsyf
hlltwslpfv ltvailavaq vdgdsvsgic fvgyknyryr
agfvlapiql vlivggyflirgvmtlfsik snhpgllsek
aaskinetml rlgifgflaf gfvlitfsch fydffnqaew
ersfrdyvlc qanvtiglpt kqpipdceik nrpsllveki
nlfamfgtgi amstwvwtka tlliwrrtwc ritqqsddep
krikkskmia kafskrhell qnpqqelsfs mhtvshdqpv
aglafdlnep sadvssawaq hvtkmvarrg ailpqdisvt
pvatpvppee qanlwlveae ispelqkrlg rkkkrrkrkk
evcplapppe lhppapapst iprlpqlprq kclvaaqawg
agdscrqgaw tlvsnpfcpe psppqdpflp sapapvawah
grrqglgpih srtnlmdtelmdadsdf;
``` an exemplary human Smo mRNA sequence is:

(SEQ ID NO: 11)
```
atggccgctg cccgcccagc gcggggggccg gagctcccgc
tcctggggct gctgctgctg ctgctgctgg ggacccggg
ccgggggggcg gcctcgagcg ggaacgcgac cgggcctggg
cctcggagcg cgggcgggag cgcgaggagg agcgcggcgg
tgactggccc tccgccgccg ctgagccact gcggccgggc
tgcccccctgc gagccgctgc gctacaacgt gtgcctgggc
taggtgctgc cctacggggc cacctccaca ctgctggccg
gagactcgga ctcccaggag aagcgcacg gcaagctcgt
gctctggtcg ggcctccgga atgcccccg ctgctgggca
gtgatccagc ccctgctgtg tgccgtatac atggcccagt
gtgagaatga ccgggtggag ctgcccagcc gtaccctctg
ccaggccacc cgaggccct gtgccatcgt ggagagggag
cggggctggc ctgacttcct gcgctgcact cctgaccgct
tccctgaagg ctgcacgaat gaggtgcaga acatcaagtt
caacagttca ggccagtgcg aagtgccctt ggttcggaca
gacaaccca agagctggta cgaggacgtg gagggctgcg
gcatccagtg ccagaacccg ctcttcacag aggctgagca
ccaggacatg cacagctaca cgcggcctt cggggccgtc
acgggcctct gcacgctctt caccctggcc acattcgtgg
ctgactggcg gaactcgaat cgctaccctg ctgttattct
cttctacgtc aatgcgtgct tctttgtggg cagcattggc
tggctggccc agttcatgga tggtgcccgc cgagagatcg
tctgccgtgc agatggcacc atgaggcttg gggagcccac
ctccaatgag actctgtcct gcgtcatcat ctttgtcatc
```

-continued

```
gtgtactacg ccctgatggc tggtgtggtt tggtttgtgg
tcctcaccta tgcctggcac acttccttca aagccctggg
caccacctac cagcctctct cgggcaagac ctcctacttc
cacctgctca cctggtcact ccccttttgtc ctcactgtgg
```

```

caatccttgc tgtggcgcag gtggatgggg actctgtgag
tggcatttgt tttgtgggct acaagaacta ccgataccgt
gcgggcttcg tgctggcccc aatcggcctg gtgctcatcg
tgggaggcta cttcctcatc cgaggagtca tgactctgtt
ctccatcaag agcaaccacc ccgggctgct gagtgagaag
gctgccagca agatcaacga gaccatgctg cgcctgggca
tttttggctt cctggccttt ggctttgtgc tcattacctt
cagctgccac ttctacgact tcttcaacca ggctgagtgg
gagcgcagct tccgggacta tgtgctatgt caggccaatg
tgaccatcgg gctgcccacc aagcagccca tccctgactg
tgagatcaag aatcgcccga gccttctggt ggagaagatc
aacctgtttg ccatgtttgg aactggcatc gccatgagca
cctgggtctg gaccaaggcc acgctgctca tctggaggcg
tacctggtgc aggttgactg ggcagagtga cgatgagcca
aagcggatca agaagagcaa gatgattgcc aaggccttct
ctaagcggca cgagctcctg cagaacccag gccaggagct
gtccttcagc atgcacactg tgtcccacga cgggcccgtg
gcgggcttgg cctttgacct caatgagccc tcagctgatg
tctcctctgc ctgggcccag catgtcacca agatggtggc
tcggagagga gccatactgc cccaggatat ttctgtcacc
cctgtggcaa ctccagtgcc cccagaggaa caagccaacc
tgtggctggt tgaggcagag atctccccag agctgcagaa
gcgcctgggc cggaagaaga agaggaggaa gaggaagaag
gaggtgtgcc cgctggcgcc gccccctgag cttcaccccc
ctgcccctgc ccccagtacc attcctcgac tgcctcagct
gccccggcag aaatgcctgg tggctgcagg tgcctgggga
gctggggact cttgccgaca gggagcgtgg accctggtct
ccaacccatt ctgcccagag cccagtcccc ctcaggatcc
atttctgccc agtgcaccgg ccccccgtggc atgggctcat
ggccgccgac agggcctggg gcctattcac tcccgcacca
acctgatgga cacagaactc atggatgcag actcggactt
ctga;
```
an exemplary human Smo sequence is:

```
(SEQ ID NO: 12)
maaarpargp elpllglll lllgdpgrga assgnatgpg
prsaggsarr saavtgpppp lshcgraapc eplrynvclg
-continued
svlpygatst llagdsdsqe eahgklvlws glrnaprcwa
viqpllcavy mpkcendrve lpsrtlcqat rgpcaivere
rgwpdflrct pdrfpegctn evqnikfnss gqcevplvrt
dnpkswyedv egcgiqcqnp lfteaehqdm hsyiaafgav
tglctlftla tfvadwrnsn rypavilfyv nacffvgsig
wlaqfmdgar reivcradgt mrlgeptsne tlscviifvi
vyyalmagvv wfvvltyawh tsfkalgtty qplsgktsyf
hlltwslpfv ltvailavaq vdgdsvsgic fvgyknyryr
agfvlapigl vlivggyfli rgvmtlfsik snhpgllsek
aaskinetml rlgifgflaf gfvlitfsch fydffnqaew
ersfrdyvlc qanvtiglpt kqpipdceik nrpsllveki
nlfamfgtgi amstwvwtka tlliwrrtwc rltgqsddep
krikkskmia kafskrhell qnpgqelsfs mhtvshdgpv
aglafdlnep sadvssawaq hvtkmvarrg ailpqdisvt
pvatpvppee qanlwlveae ispelqkrlg rkkkrrkrkk
evcplapppe lhppapapst iprlpqlprq kclvaagawg
agdscrqgaw tlvsnpfcpe psppqdpflp sapapvawah
grrqglgpih srtnlmdtel mdadsdf;
```
an exemplary Ptc1 mRNA sequence is:

```
>NM_008957.3 *Mus musculus* patched 1 (Ptch1), transcript variant 1, mRNA
(SEQ ID NO: 7)

GCGGCCGCAAAGACCTCGGGACTCACGCGCAATGTGGCAATGGAAGGCGC

AGGGTCTGAGTCCCCGGCAGCGGCCACGGCCGCAGCACCCGCAGCGCCCG

CCGTGTGAGCGGCAGCAGCGGGTCTGTCACCCGGAGCCGGAGTCCCCGGC

GGCCAGCAGCGTCCTCGCGAGCCGAGCGCCCAGGCGCGCCCGGAGCCCGC

GGCGGCGGCGGCAACATGGCCTCGGCTGGTAACGCCGCCGGGGCCCTGGG

CAGGCAGGCCGGCGGCGGGAGGCGCAGACGGACCGGGGGACCGCACCGCG

CCGCGCCGGACCGGGACTATCTGCACCGGCCCAGCTACTGCGACGCCGCC

TTCGCTCTGGAGCAGATTTCCAAGGGGAAGGCTACTGGCCGGAAAGCGCC

GCTGTGGCTGAGAGCGAAGTTTCAGAGACTCTTATTTAAACTGGGTTGTT

ACATTCAAAAGAACTGCGGCAAGTTTTTGGTTGTGGGTCTCCTCATATTT

GGGGCCTTCGCTGTGGGATTAAAGGCAGCTAATCTCGAGACCAACGTGGA

GGAGCTGTGGGTGGAAGTTGGTGGACGAGTGAGTCGAGAATTAAATTATA

CCCGTCAGAAGATAGGAGAAGAGGCTATGTTTAATCCTCAACTCATGATA

CAGACTCCAAAAGAAGAAGGCGCTAATGTTCTGACCACAGAGGCTCTCCT

GCAACACCTGGACTCAGCACTCCAGGCCAGTCGTGTGCACGTCTACATGT

ATAACAGGCAATGGAAGTTGGAACATTTGTGCTACAAATCAGGGGAACTT

ATCACGGAGACAGGTTACATGGATCAGATAATAGAATACCTTTACCCTTG

CTTAATCATTACACCTTTGGACTGCTTCTGGGAAGGGGCAAAGCTACAGT

CCGGGACAGCATACCTCCTAGGTAAGCCTCCTTTACGGTGGACAAACTTT
```

```
GACCCCTTGGAATTCCTAGAAGAGTTAAAGAAAATAAACTACCAAGTGGA
CAGCTGGGAGGAAATGCTGAATAAAGCCGAAGTTGGCCATGGGTACATGG
ACCGGCCTTGCCTCAACCCAGCCGACCCAGATTGCCCTGCCACAGCCCCT
AACAAAAATTCAACCAAACCTCTTGATGTGGCCCTTGTTTTGAATGGTGG
ATGTCAAGGTTTATCCAGGAAGTATATGCATTGGCAGGAGGAGTTGATTG
TGGGTGGTACCGTCAAGAATGCCACTGGAAAACTTGTCAGCGCTCACGCC
CTGCAAACCATGTTCCAGTTAATGACTCCCAAGCAAATGTATGAACACTT
CAGGGGCTACGACTATGTCTCTCACATCAACTGGATTGAAGACAGGGCAG
CCGCCATCCTGGAGGCCTGGCAGAGGACTTACGTGGAGGTGGTTCATCAA
AGTGTCGCCCCAAACTCCACTCAAAAGGTGCTTCCCTTCACAACCACGAC
CCTGGACGACATCCTAAAATCCTTCTCTGATGTCAGTGTCATCCGAGTGG
CCAGCGGCTACCTACTGATGCTTGCCTATGCCTGTTTAACCATGCTGCGC
TGGGACTGCTCCAAGTCCCAGGGTGCCGTGGGGCTGGCTGGCGTCCTGTT
GGTTGCGCTGTCAGTGGCTGCAGGATTGGGCCTCTGCTCCTTGATTGGCA
TTTCTTTTAATGCTGCGACAACTCAGGTTTTGCCGTTTCTTGCTCTTGGT
GTTGGTGTGGATGATGTCTTCCTCCTGGCCCATGCATTCAGTGAAACAGG
ACAGAATAAGAGGATTCCATTTGAGGACAGGACTGGGGAGTGCCTCAAGC
GCACCGGAGCCAGCGTGGCCCTCACCTCCATCAGCAATGTCACCGCCTTC
TTCATGGCCGCATTGATCCCTATCCCTGCCCTGCGAGCGTTCTCCCTCCA
GGCTGCTGTGGTGGTGGTATTCAATTTTGCTATGGTTCTGCTCATTTTTC
CTGCAATTCTCAGCATGGATTTATACAGACGTGAGGACAGAAGATTGGAT
ATTTTCTGCTGTTTCACAAGCCCCTGTGTCAGCAGGGTGATTCAAGTTGA
GCCACAGGCCTACACAGAGCCTCACAGTAACACCCGGTACAGCCCCCCAC
CCCCATACACCAGCCACAGCTTCGCCCACGAAACCCATATCACTATGCAG
TCCACCGTTCAGCTCCGCACAGAGTATGACCCTCACACGCACGTGTACTA
CACCACCGCCGAGCCACGCTCTGAGATCTCTGTACAGCCTGTTACCGTCA
CCCAGGACAACCTCAGCTGTCAGAGTCCCGAGAGCACCAGCTCTACCAGG
GACCTGCTCTCCCAGTTCTCAGACTCCAGCCTCCACTGCCTCGAGCCCCC
CTGCACCAAGTGGACACTCTCTTCGTTTGCAGAGAAGCACTATGCTCCTT
TCCTCCTGAAACCCAAAGCCAAGGTTGTGGTAATCCTTCTTTTCCTGGGC
TTGCTGGGGGTCAGCCTTTATGGGACCACCCGAGTGAGAGACGGGCTGGA
CCTCACGGACATTGTTCCCCGGGAAACCAGAGAATATGACTTCATAGCTG
CCCAGTTCAAGTACTTCTCTTTCTACAACATGTATATAGTCACCCAGAAA
GCAGACTACCCGAATATCCAGCACCTACTTTACGACCTTCATAAGAGTTT
CAGCAATGTGAAGTATGTCATGCTGGAGGAGAACAAGCAACTTCCCCAAA
TGTGGCTGCACTACTTTAGAGACTGGCTTCAAGGACTTCAGGATGCATTT
GACAGTGACTGGGAAACTGGGAGGATCATGCCAAACAATTATAAAAATGG
ATCAGATGACGGGGTCCTCGCTTACAAACTCCTGGTGCAGACTGGCAGCC
GAGACAAGCCCATCGACATTAGTCAGTTGACTAAACAGCGTCTGGTAGAC
GCAGATGGCATCATTAATCCGAGCGCTTTCTACATCTACCTGACCGCTTG
GGTCAGCAACGACCCTGTAGCTTACGCTGCCTCCCAGGCCAACATCCGGC
CTCACCGGCCGGAGTGGGTCCATGACAAAGCCGACTACATGCCAGAGACC
AGGCTGAGAATCCCAGCAGCAGAGCCCATCGAGTACGCTCAGTTCCCTTT
CTACCTCAACGGCCTACGAGACACCTCAGACTTTGTGGAAGCCATAGAAA
AAGTGAGAGTCATCTGTAACAACTATACGAGCCTGGACTGTCCAGCTAC
CCCAATGGCTACCCCTTCCTGTTCTGGGAGCAATACATCAGCCTGCGCCA
CTGGCTGCTGCTATCCATCAGCGTGGTGCTGGCCTGCACGTTTCTAGTGT
GCGCAGTCTTCCTCCTGAACCCCTGGACGGCCGGGATCATTGTCATGGTC
CTGGCTCTGATGACCGTTGAGCTCTTTGGCATGATGGGCCTCATTGGGAT
CAAGCTGAGTGCTGTGCCTGTGGTCATCCTGATTGCATCTGTTGGCATCG
GAGTGGAGTTCACCGTCCACGTGGCTTTGGCCTTTCTGACAGCCATTGGG
GACAAGAACCACAGGGCTATGCTCGCTCTGGAGCACATGTTTGCTCCCGT
TCTGGACGGTGCTGTGTCCACTCTGCTGGGTGTACTGATGCTTGCAGGGT
CCGAATTTGATTTCATTGTCAGATACTTCTTTGCCGTCCTGGCCATTCTC
ACCGTCTTGGGGGTTCTCAATGGACTGGTTCTGCTGCCTGTCCTCTTATC
CTTCTTTGGACCGTGTCCTGAGGTGTCTCCAGCCAATGGCCTAAACCGAC
TGCCCACTCCTTCGCCTGAGCCGCCTCCAAGTGTCGTCCGGTTTGCCGTG
CCTCCTGGTCACACGAACAATGGGTCTGATTCCTCCGACTCGGAGTACAG
CTCTCAGACCACGGTGTCTGGCATCAGTGAGGAGCTCAGGCAATACGAAG
CACAGCAGGGTGCCGGAGGCCCTGCCCACCAAGTGATTGTGGAAGCCACA
GAAAACCCTGTCTTTGCCCGGTCCACTGTGGTCCATCCGGACTCCAGACA
TCAGCCTCCCTTGACCCCTCGGCAACAGCCCCACCTGGACTCTGGCTCCT
TGTCCCCTGGACGGCAAGGCCAGCAGCCTCGAAGGGATCCCCCTAGAGAA
GGCTTGCGGCCACCCCCCTACAGACCGCGCAGAGACGCTTTTGAAATTTC
TACTGAAGGGCATTCTGGCCCTAGCAATAGGGACCGCTCAGGGCCCCGTG
GGGCCCGTTCTCACAACCCTCGGAACCCAACGTCCACCGCCATGGGCAGC
TCTGTGCCCAGCTACTGCCAGCCCATCACCACTGTGACGGCTTCTGCTTC
GGTGACTGTTGCTGTGCATCCCCCGCCTGGACCTGGGCGCAACCCCCGAG
GGGGGCCCTGTCCAGGCTATGAGAGCTACCCTGAGACTGATCACGGGGTA
TTTGAGGATCCTCATGTGCCTTTTCATGTCAGGTGTGAGAGGAGGGACTC
AAAGGTGGAGGTCATAGAGCTACAGGACGTGGAATGTGAGGAGAGGCCGT
GGGGGAGCAGCTCCAACTGAGGGTAATTAAAATCTGAAGCAAAGAGGCCA
AAGATTGGAAAGCCCCGCCCCCACCTCTTTCCAGAACTGCTTGAAGAGAA
CTGCTTGGAATTATGGGAAGGCAGTTCATTGTTACTGTAACTGATTGTAT
TATTTTGTGAAATATTTCTATAAATATTTAAAGGTGTACACATGTAATA
TACATGAAATGCTGTACAGTCTATTTCCTGGGGCCTCTCCACTCCTGCC
CCAGAGTGGGGAGACCACAGGGGCCCTTTCCCCTGTGTACATTGGTCTCT
GTGCCACAACCAAGCTTAACTTAGTTTTAAAAAAAATCTCCCAGCATATG
TCGCTGCTGCTTAAATATTGTATAATTTACTTGTATAATTCTATGCAAAT
ATTGCTTATGTAATAGGATTATTTGTAAAGGTTTCTGTTTAAAATATTTT
AAATTTGCATATCACAACCCTGTGGTAGGATGAATTGTTACTGTTAACTT
TTGAACACGCTATGCGTGGTAATTGTTTAACGAGCAGACATGAAGAAAAC
```

```
AGGTTAATCCCAGTGGCTTCTCTAGGGGTAGTTGTATATGGTTCGCATGG
GTGGATGTGTGTGCATGTGACTTTCCAATGTACTGTATTGTGGTTTGT
TGTTGTTGTTGCTGTTGTTGTTCATTTTTGTGTTTTTTGTTGCTTTGTAT
GATCTTAGCTCTGGCCTAGGTGGGCTGGGAAGGTCCAGGTCTTTTTCTGT
CGTGATGCTGGTGGAAAGGTGACCCCAATCATCTGTCCTATTCTCTGGGA
CTATTCAAGAGAAGCCAGATTTGCTTCATGCCTGTGTGTGGCAGCTTCTG
AGGTCATGGGTAGCCCTCCAAGCACCTCTGCTTGGGTTTCAAAGAGAAGA
TGTTCTCACAAACATTGTGCTGCCTATTAGGGCCTCTATATAGTCAGCAG
TCAGCACTAGTGGTGAAAGATTGGACAATGTTGCCTGATGGTGAGACTCA
GCCGGGTCATGAGATTACCCTCTAGGGGTGTGTGGTTGTTCCTTTCTGAT
GATCACACATACACACAGCCTCCCACCCCCATACTCCAGATACAGGCCCA
AAAAAACCTATTTCACTGAAGGTCTATATTCGAGCCTTTACAAATGATAG
TCCCTCCCTTGCTATGACTGCCTGGTTGGAGCAGGCTAGGCTAATCGTGG
TTCAGTCAACTGTGTGGGAGAGTTTCTAAGGACTCTTTTCCACACGGTC
TTTTCCTGTGTATACTTTCTTCTCTTCCCCACTGTTAGCATCCATCCAGT
GTGATGTCTGTGAAAGCAGGAAGATGCCACCTCGTAAAAGCATATAGGGT
AAGCTCTTTGAACCAGGTGTTGGGCTTTAGAGTTTGATTGTGTTCTCCTT
CCCCAAGGTTTGGGTTTCTTTGTCTCTGGTCAGCAACTAGTAGATAGGGA
AGGAAATGCCCTTATTCCTTGCAAGTGAACATTGAGGACTTGTCTCAGAG
GAAGGAAGCCTAGTGCTCATGGAAGCTGTTGTGAGGAATGTACTCTGTCT
GCATGCAGCTTCCCTGAATCCTCCTATCCTTCATGGAAAAATTTAAGGA
GATGGGTCCCTAGTAGTACCAATAATCTAGTGCCCTCAGATCCTAAAATT
TATCCCCCAAATTGTAAGGTACTAATTGGAAGCCACCTGTGACTACCGTG
TGTGTGTGTGTCTGTGTCTGTCTGTATATCCGTGTGCGCGTGCGCGCCAG
AAGCCCTGGCCATCCACTGCTACTGTCTTAATGCCTGTCAAGCCACTGTC
TGCCTACCCAACACCAGCTCTGCTCGGATATCTTGCACCCTGAGTTGAGG
AGGGAGATGTAGAGTGCGGAAGCCACCTTGGCTGTGGTTCTTGATTGTGT
CCCTCATGCCTGAGCCTTGTGCATGTGGCAGAAGGAAGTTTGTACAGCCT
CTCGGCTTCTGTGCATCATCATGAGTCCCATCAGCCAAGGCAGGAAGGAC
ACAGAGCTGGCAGGAGACTAAAGTCAGAGAGTGTGTCTCTCTGTCTGTCT
CTCTCATAGTTTTATTTTGTCTGTATTGTTTGTTCATTTGGATGTTTAA
TTTGTAAAGAAAAGATCTTTGCTGATATTTATAATTTTGTATCATAAGA
ATGTCCTCCAGAATTTGTCATGCCAGTTTATAACAAGAAGAAAAAATTGC
AGGGATTTTATTTCTATTGGAAACACTTATTGCAGTTATGTTTTACTTTT
GAACAGAAGTTTTATTTGTATAGAGTGCTTACTAATGTTAAATAGTTCAG
AGTATATAACATTTACATTAAGGACTCATGGTAGGTTTTAGTGTAAGGAG
TTTAAAGGAAATAAATATTCAAACTGGGTCTCGTCTGCCAATTTGGGTGG
AAATGAGTTTGTGTCACTTCAATTACAAAGATGAAAGTATGCCATATAAT
TTATTTATATGAAAATTTATTTTGTAGTGTACATAGTAGTCATCAAGTC
TTTCGACAGAAGTATATTTTAAAGAATTTATATGTGATGAAATCCATAA
TGTCTGGAACTTTGCTGAGACATGGGTGTGAGGACACGTTTCGTTATAAA
TGACAGCAAGGGAGAGAAGAGAGTATGTTTTAACAGTGTTAGGAGAGTAC
ACGTGAGCAGTGATCCATGTGATTGGAAAGTATCGGTGTGAACATGGTGA
CCTAGTGCGGTTCTCAGATGAAAATGTACAAAACTCTCTAAATATTAATG
TTCAAACACTGATAGAAATTCTAACATGAATAAAGATAATATAACTTGTT
GGTTTAAAAAAAAAAAAAAAAAA;
``` an exemplary Ptc1 protein sequence is:

(SEQ ID NO: 2)

```
masagnaaep qdrggggsgc igapgrpagg grrrrtgglr
raaapdrdyl hrpsycdaaf aleqiskgka tgrkaplwlr
akfqrllfkl gcyiqkncgk flvvgllifg afavglkaan
letnveelwv evggrvsrel nytrqkigee amfnpqlmiq
tpkeeganvl tteallghld salqasrvhv ymynrqwkle
hlcyksgeli tetgvmdqii eylypcliit pldcfwegak
lqsgtayllg kpplrwtnfd plefleelkk inyqvdswee
mlnkaevghg ymdrpclnpa dpdcpatapn knstkpldma
lvlnggchgl srkymhwqee livggtvkns tgklvsahal
qtmfqlmtpk qmyehfkgye yvshinwned kaaaileawq
rtyvevvhqs vaqnstgkvl sfttttlddi lksfsdvsvi
rvasgyllml ayacltmlrw dcsksqgavg lagvllvals
vaaglqlcsl igisfnaatt qvlpflalgv qvddvfllah
afsetgqnkr ipfedrtgec lkrtgasval tsisnvtaff
maalipipal rafslqaavv vvfnfamvll ifpailsmdl
yrredrridi fccftspcvs rviqvepqay tdthdntrys
ppppysshsf ahetqitmqs tvglrteydp hthvyyttae
prseisvqpv tvtqdtlscq spestsstrd llsqfsdssl
hcleppcctkw tlssfaekhy apfllkpkak vvviflflgl
lgvslygttr vrdgldltdi vpretreydf iaaqfkvfsf
ynmyivtqka dypniqhlly dlhrsfsnvk yvmleenkql
pkmwlhyfrd wlqglgdafd sdwetgkimp nnykngsddg
vlaykllvqt gsrdkpidis qltkqrlvda dgiinpsafy
iyltawvsnd pvayaasqan irphrpewvh dkadympetr
lripaaepie yaqfpfylng lrdtsdfvea iekvrticsn
ytslglssyp ngypflfweq yiglrhwlll fisvvlactf
lvcavfllnp wtagiivmvl almtvelfgm mgligiklsa
vpvviliasv gigveftvhv alafltaigd knrravlale
hmfapvldga vstllgvlml agsefdfivr vffavlailt
ilgvlnglvl lpvllsffgp ypevspangl nrlptpspep
ppsvvrfamp pghthsgsds sdseyssqtt vsqlseelrh
yeaqqgaggp ahqviveate npvfahstvv hpesrhhpps
nprqqphlds gslppgrqgq qprrdppreg lwpppyrprr
```

-continued dafeistegh sqpsnrarwg prgarshnpr npastamgss vpgycqpitt vtasasvtva vhpppvpgpg rnprgglcpg ypetdhglfe dphvpfhvrc errdskvevi elqdveceer prgsssn;

an exemplary Shh mRNA sequence is:

```
>NM_009170.3 Mus musculus sonic hedgehog (Shh),
mRNA
                                    (SEQ ID NO: 8)
ACAAGCTCTCCAGCCTTGCTACCATTTAAAATCAGGCTCTTTTTGTCTTT

TAATTGCTGTCTCGAGACCCAACTCCGATGTGTTCCGTTACCAGCGACCG

GCAGCCTGCCATCGCAGCCCCAGTCTGGGTGGGGATCGGAGACAAGTCCC

CTGCAGCAGCGGCAGGCAAGGTTATATAGGAAGAGAAAGAGCCAGGCAGC

GCCAGAGGGAACGAACGAGCCGAGCGAGGAAGGGAGAGCCGAGCGCAAGG

AGGAGCGCACACGCACACACCCGCGCGTACCCGCTCGCGCACAGACAGCG

CGGGGACAGCTCACAAGTCCTCAGGTTCCGCGGACGAGATGCTGCTGCTG

CTGGCCAGATGTTTTCTGGTGATCCTTGCTTCCTCGCTGCTGGTGTGCCC

CGGGCTGGCCTGTGGGCCCGGCAGGGGGTTTGGAAAGAGGCGGCACCCCA

AAAAGCTGACCCCTTTAGCCTACAAGCAGTTTATTCCCAACGTAGCCGAG

AAGACCCTAGGGGCCAGCGGCAGATATGAAGGGAAGATCACAAGAAACTC

CGAACGATTTAAGGAACTCACCCCCAATTACAACCCCGACATCATATTTA

AGGATGAGGAAAACACGGGAGCAGACCGGCTGATGACTCAGAGGTGCAAA

GACAAGTTAAATGCCTTGGCCATCTCTGTGATGAACCAGTGGCCTGGAGT

GAAGCTGCGAGTGACCGAGGGCTGGGATGAGGACGGCCATCATTCAGAGG

AGTCTCTACACTATGAGGGTCGAGCAGTGGACATCACCACGTCCGACCGG

GACCGCAGCAAGTACGGCATGCTGGCTCGCCTGGCTGTGGAAGCAGGTTT

CGACTGGGTCTACTATGAATCCAAAGCTCACATCCACTGTTCTGTGAAAG

CAGAGAACTCCGTGGCGGCCAAATCCGGCGGCTGTTTCCCGGGATCCGCC

ACCGTGCACCTGGAGCAGGGCGGCACCAAGCTGGTGAAGGACTTACGTCC

CGGAGACCGCGTGCTGGCGGCTGACGACCAGGGCCGGCTGCTGTACAGCG

ACTTCCTCACCTTCCTGGACCGCGACGAAGGCGCCAAGAAGGTCTTCTAC

GTGATCGAGACGCTGGAGCCGCGCGAGCGCCTGCTGCTCACCGCCGCGCA

CCTGCTCTTCGTGGCGCCGCACAACGACTCGGGGCCCACGCCCGGGCCAA

GCGCGCTCTTTGCCAGCCGCGTGCGCCCCGGGCAGCGCGTGTACGTGGTG

GCTGAACGCGGCGGGACCGCCGGCTGCTGCCCGCCGCGGTGCACAGCGT

GACGCTGCGAGAGGAGGAGGCGGGCGCGTACGCGCCGCTCACGGCGCACG

GCACCATTCTCATCAACCGGGTGCTCGCCTCGTGCTACGCTGTCATCGAG

GAGCACAGCTGGGCACACCGGGCCTTCGCGCCTTTCCGCCTGGCGCACGC

GCTGCTGGCCGCGCTGGCACCCGCCCGACGGACGGCGGGGCGGGGCA

GCATCCCTGCAGCGCAATCTGCAACGGAAGCGAGGGGCGCGGAGCCGACT

GCGGGCATCCACTGGTACTCGCAGCTGCTCTACCACATTGGCACCTGGCT

GTTGGACAGCGAGACCATGCATCCCTTGGGAATGGCGGTCAAGTCCAGCT
```

```
GAAGCCCGACGGGACCGGGCAAGGGGCGGGCGGGGCGGGGAGCGACTGCG

AAATAAGGAACTGATGGGAAAGCGCACGGAAGGAGACTTTTAATTATAAG

AATAATTCATAATAATAATAATAATGATAATAATAATAATAATAAGTAGG

GCAGTCCAAAGTAGACTATAAGGAAGCAAAAACCCCGGGGAGTTCTGTTG

TTATGTTTAGTTTATATATTTTTTTGAAATTTTTCGTTATTGTCTTATAT

GGGTTGTTTTCTCCTCTCCTGGCTATTTATTTGTTTCGTATGAATAGAT

GTTTTAAAAATATGAACGGACCTTCAAGAGCCTTAACTAGTTTGTGTCTT

GGATAATTTATTATTGTGTGAACTGTACTCACAGTGAGGGAAAGATTATT

TTGTGAGGCCAAGCAACCTGCTGAAAGTCTATTTTTCTACATGTCCCTTG

TCCTGCGTTTCAGAAGGCAAACCTCCGCATTCCTCTCCTGCTATGCTCCT

GCTTTCCCGCAAGTGTAAACTAAAACCTGCTCCATGGGGGTCCACAAATT

ATATTTTTATACACAGAATTGTAAATTAGATTTTTGAGAGATCAATACCT

AACTGAATGACATTTCATTTTTTGAAAGTGTAAAATATGAAAATATATTA

TTTTAATTTAACTATTTTCCAATGTAATAGCCGTCTTCTGTACTGCCTTC

TTGGTTTGTATTTGCTTTGTAACCGCCACTTTGTCATGTTCTTGGAAACC

AAGACTGTTAACGCACACATATACACTTTTTTTTTGACAGACTGGAAGA

ACTCTGTTATTTTTAACTTCAAAGAATTTATTAGAAAATAATATTTTTA

AAAGTGCACCTAGCAGCGAGCCCACGAGGATGGAGCCTGTAGTTTGTACA

GAGAAAACAAGGATGTTTTTGCATTAATAAACTGAGAAGTAACTGCTGT

AAATTTACTAAAATGTATTTTTGAATATTTTGTAATAGTTTTATAGAAAT

AAAGCGTGCCACACACAAAAAAAAAAAAAAAAAAAAAAAAAAAAAAAA

AAAAAAAAAAAAAAAAAAAAAAAAA;
``` an exemplary Shh protein sequence is:

```
                                    (SEQ ID NO: 3)
    mlllarclll vlvssllvcs glacgpgrgf gkrrhpkklt playkqfipn vaektlgasg ryegkisrns erfkeltpny npdiifkdee ntgadrlmtq rckdklnala isvmnqwpgv klrvtegwde dghhseeslh yegravditt sdrdrskygm larlaveagf dwvyyeskah ihcsvkaens vaaksggcfp gsatvhleqg gtklvkdlsp gdrvlaaddq grllysdflt fldrddgakk vfyvietrep rerllltaah llfvaphnds atgepeassg sgppsggalg pralfasrvr pgqrvyvvae rdgdrrllpa avhsvtlsee aagayaplta qgtilinrvl ascyavieeh swahrafapf rlahallaal apartdrggd sgggdrgggg grvaltapga adapgagata gihwysqlly qigtwlldse alhplgmavk ss;
``` an exemplary Gli1 mRNA sequence is:

```
>AB025922.1 Mus musculus Gli1 mRNA, complete cds
                                    (SEQ ID NO: 9)
CACGCATCCCGAGCACCGCGCCCCGACGGAGGTCTCTTTGTCCGCGGCTC

TCCCACATACTAGAAATCTCTCCCTTTCTTGAGGTTGGGATGAAGAAGCA
```

```
GTTGGGACGGCCAGCTGGAGGTCTGCGTGGTAGAGGGAACTCCAGGTCCC
CTCATCCTTCCCTGAGACGCCATGTTCAATCCAATGACTCCACCACAAGT
CAATAGCTATAGTGAGCCATGCTGTCTCCGACCCCTCCACAGCCAAGGAG
TCCCCAGCATGGGAACAGAAGGACTTTCTGGTCTGCCCTTTTGCCACCAA
GCCAACTTTATGTCAGGGTCCCAGGGTTATGGAGCAGCCAGAGAGACCAG
CAGCTGCACTGAAGGATCTCTCTTTCCTCCTCCTCCTCCTCCTCGGAGTT
CAGTCAAATTAACAAAGAAGCGGGCTCTCTCCATCTCGCCCCTTTCTGAT
GCCAGCCTCGACCTGCAAACCGTAATCCGGACCTCACCCAGCTCCCTGGT
GGCTTTCATCAACTCTCGCTGTACATCTCCGGGCGGTTCCTACGGCCATC
TCTCCATTGGTACCATGAGCCCTTCTTTAGGATTCCCACCTCAGATGAGT
CATCAAAAGGAACTTCACCTCCCTATGGAGTCCAGCCCTGTGTTCCACA
TGACTCTACTCGGGGTTCAATGATGCTTCACCCCCAGGCCCGGGGACCAC
GTGCAACCTGCGAGCTGAAGTCAGAGCTGGATATGATGGTTGGCAAGTGC
CCGGAGGACCCTTTGGAAGGGGACATGTCTAGCCCCAACTCCACAGGCAT
ACAGGATCACCTGTTGGGGATGCTGGATGGGCGGGAGGACCTGGAGAGAG
AGGAGAAGCCTGAGCCTGAGTCTGTGTATGAGACAGACTGCCGCTGGGAT
GGTTGCAGCCAGGAGTTCGATTCCCAGGAGCAGCTGGTGCACCACATCAA
CAGTGAGCATATCCACGGGGAGCGGAAGGAATTCGTGTGCCATTGGGGAG
GTTGCTCCAGGGAGCTGAGGCCCTTCAAGGCCAATACATGCTGGTGGTG
CACATGCGCAGACACACGGGCGAGAAGCCACACAAGTGCACGTTTGAAGG
CTGTCGGAAGTCCTATTCACGCCTTGAAAACCTCAAGACGCACCTTCGGT
CGCACACGGGTGAGAAGCCTTACATGTGTGAGCAAGAAGGTTGCAGCAAG
GCCTTTAGCAATGCCAGTGACCGCGCCAAGCACCAGAATCGGACCCACTC
CAATGAGAAGCCATACGTGTGCAAGCTCCCCGGCTGCACCAAGCGCTACA
CAGATCCCAGCTCGCTCCGCAAACACGTGAAGACAGTGCATGGTCCGGAT
GCCCACGTGACCAAGCGGCATCGAGGGGATGGCCCCTTGCCACGGGCTCA
GCCCCTCTCCACAGTGGAGCCCAAGCGGGAAAGGGAAGGAGGATCCGGCA
GGGAAGAGAGCAGACTGACTGTGCCCGAGAGTGCCATGCCGCAGCAGAGC
CCCGGAGCGCAGTCCTCTTGCAGCAGCGTCCACTCCCCAGCAGGCAGTGC
GGCCAACACGGACAGCGGCGTGGAGATGGCCGGCAACGCCGGGGCAGCA
CTGAGGACTTGTCCAGCTTGGATGAAGGACCTTGTGTCTCGGCCACCGGA
CTCTCCACGCTTCGCCGCCTGGAGAACCTTAGGCTGGATCAGCTGCATCA
GCTCCGGCCCATAGGGTCTCGGGGTCTCAAATTGCCCAGCTTAACCCACG
CTGGCGCACCTGTGTCTCGCCGTCTGGGCCCCCAGTCTCCCTGGACCGC
CGCAGCAGCAGCTCCAGCAGCATGAGCTCTGCTTACACAGTCAGCCGCAG
GTCCTCCCTGGCATCCCCTTTCCCGCCGGGAACCCCACCAGAGAATGGGG
CATCGTCACTACCTGGCCTCACACCTGCTCAGCACTACATGCTCCGTGCC
AGATATGCTTCAGCCAGGGGGAGTGGCACCCCGCCCACTGCAGCTCACAG
CCTGGATCGGATGGGAGGTCTTTCTGTTCCTCCTTGGAGAAGCCGAACCG
AGTACCCGGGATACAACCCAAATGCAGGGGTCACTCGGAGGGCCAGTGAC
CCAGCCCGGGCTGCTGACCACCCAGCTCCAGCCAGAGTCCAGCGGTTCAA
GAGCCTGGGATGTGTCCACACGCCCCCTAGTGTGGCAACGGGACGGAACT
TCGATCCCCACCACCCTACCTCTGTCTATTCGCCACAGCCCCCCAGCATC
ACCGAAAATGTTGCCATGGATACTAGGGGGCTACAGGAGGAGCCAGAGGT
TGGAACTTCTGTGATGGGCAATGGTCTGAACCCATACATGGATTTTTCCT
CCACTGATACTCTGGGATATGGGGGACCCGAGGGGACGGCAGCTGAGCCT
TATGAAGCTAGGGGTCCAGGTTCCCTGCCTCTTGGGCCTGGTCCACCAAC
CAACTATGGCCCTGGCCACTGTGCCCAGCAGGTCTCCTATCCCGATCCCA
CCCCAGAAAACTGGGGTGAGTTCCCTTCTCATGCTGGGGTGTACCCTAGC
AATAAGGCTCCGGGTGCTGCCTATAGCCAGTGTCCTCGACTTGAGCATTA
TGGACAAGTGCAGGTAAAACCAGAACAAGGGTGCCCAGTGGGGTCTGACT
CCACCGGATTGGCACCCTGCCTCAATGCCCACCCCAGTGAAGGGTCCCCA
GGCCCGCAGCCTCTGTTTTCACATCATCCCCAGCTCCCTCAGCCCCAGTA
TCCCCAGTCGGGTCCCTATCCTCAGCCTCCCCATGGTTATCTCTCAACAG
AACCCAGGCTTGGCCTCATTTTCAACCCCTCCTCCTCTCATTCCACAGGA
CAGCTCAAAGCTCAGCTGGTGTCTAATTACTTTCAGTCGCAGCAGGAATT
GTTGTGGGAGGGAAGAAACCGGGGAGGGCTCCCCAACCAGGAACTCCCAT
ACCAGAGCCCCAAGTTTCTGGGGGGTTCCCAAGTTAGTCAGAGCCCTGCC
AAGACCCCAGCAGCAGCGGCGGCAGCATATGGATCTGGCTTTGCACCTGC
TTCGGCCAATCACAAATCAGGCTCCTATCCTGCCCCTTCACCCTGCCATG
AAACTTTCACCGTGGGAGTAAACAGGCCTTCCCACAGGCCAGCAGCACCA
CCCCGACTTCTGCCCCCGCTGTCCCCTTGCTATGGGCCCCTCAAGGTGGG
GGATACCAACCCCAGCTGTGGCCATCCTGAGGTGGGCAGGTTAGGAGCAG
GCCCTGCCTTGTACCCTCCTCCTGAAGGGCAGGTGTGTAACGCTCTGGAC
TCTCTTGACCTGGACAACACTCAGCTGGACTTTGTGGCTATCCTAGATGA
GGCCCAGGGCCTGAGCCCTCCTCTTTCCCATGAGCAAGGGGACAGCTCTA
AAAAACACCCCATCTCCCTCTGGGCCCCCCAACATGGCAGTGGGTAACATG
AGTGTCTTGCTGGGGTCTCTGCCTGGAGAGACACAATTCCTCAACTCTAG
TGCCTAAAAGGGTAAGGAACCCCAAGCAGATGGTATTTCCTAAATGGCTA
CATGAGGTGCCCAGGGATGGGAGGTTTGGGCTGGGGGCTGTATTTAGTCT
ATGTATGTTCCAGGAAAGAACAAACTTTAATAATGACACAGTTTCCTGAC
AATAAAGGAATACTGAGAACAAAAAAAAAAAAAAAAA
``` an exemplary Gli1 protein sequence is:

```
                                         (SEQ ID NO: 4)
 mfnsmtpppi ssygepcclr plpsqgapsv gteglsgppf chqanlmsgp hsygparetn sctegplfss prsavkltkk ralsisplsd asldlgtvir tspsslvafi nsrctspggs yghlsigtms pslgfpaqmn hqkgpspsfg vqpcgphdsa rggmiphpqs rgpfptcqlk seldmlvgkc reeplegdms spnstgiqdp llgmldgred lereekrepe svyetdcrwd gcsqefdsqe qlvhhinseh ihgerkefvc hwggcsrelr
```

```
pfkaqymlvv hmrrhtgekp hkctfegcrk sysrlenlkt
hlrshtgekp ymcehegcsk afsnasdrak hqnrthsnek
pyvcklpgct krytdpsslr khvktvhgpd ahvtkrhrgd
gplprapsis tvepkrereq gpireesrlt vpegamkpqp
spgaqsscss dhspagsaah tdsgvemtgn aggstedlss
ldegpciagt glstlrrlen lrldqlhqlr pigtrglklp
slshtgttvs rrvgppvsle rrssssssis saytvsrrss
laspfppgsp pengasslpg lmpaqhyllr aryasarggg
tsptaassld rigglpmppw rsraeypgyn pnagvtrras
dpaqaadrpa parvqrfksl gcvhtpptva gggqnfdpyl
ptsvyspqpp sitenaamda rglqeepevg tsmvgsglnp
ymdfpptdtl gyggpegaaa epygargpgs lplgpgpptn
ygpnpcpqqa sypdptqetw gefpshsgly pgpkalggty
sqcprlehyg qvqvkpeqgc pvgsdstgla pclnahpseg
pphpqplfsh ypqpsppqyl qsgpytqppp dylpseprpc
ldfdspthst gqlkaqlvcn yvqsqqellw egggredapa
qepsyqspkf lgdsqvspsr akapvntvgp gfgpnlpnhk
sgsyptpspc henfvvganr ashraaappr llpplptcyg
plkvggtnps cghpevgrlg ggpalyppppe gqvcnpldsl
dldntqldfv aildepqgls pppshdqrgs sghtpppsgp
pnmavgnmsv llrslpgetq flnssa
``` an exemplary human Gli1 sequence is:

```
                                        (SEQ ID NO: 13)
mfnsmtpppi ssygepccls plpsqgapsv gteglsgppf
chqanlmsgp hsygparetn sctegplfss prsavkltkk
ralsisplsd asldlqtvir tspsslvafi nsrctspggs
yghlsigtms pslgfpaqmn hqkgpspsfg vqpcgphdsa
rggmiphpqs rgpfptcqlk seldmlvgkc reeplegdms
spnstgiqdp llgmldgred lereekrepe svyetdcrwd
gcsqefdsqe qlvhhinseh ihgerkefvc hwggcsrelr
pfkaqymlvv hmrrhtgekp hkctfegcrk sysrlenlkt
hlrshtgekp ymcehegcsk afsnasdrak hqnrthsnek
pyvcklpgct krytdpsslr khvktvhgpd ahvtkrhrgd
gplprapsis tvepkrereg gpireesrlt vpegamkpqp
spgagsscss dhspagsaan tdsgvemtgn aggstedlss
ldegpciagt glstlrrlen lrldqlhqlr pigtrglklp
slshtgttvs rrvgppvsle rrssssssis saytvsrrss
laspfppgsp pengasslpg lmpaqhyllr aryasarggg
tsptaassid rigglpmppw rsraeypgyn pnagvtrras
dpaqaadrpa parvqrfksl gcvhtpptva gggqnfdpyl
ptsvyspqpp sitenaamda rglqeepevg tsmvgsglnp
ymdfpptdtl gyggpegaaa epygargpgs lplgpgpptn
ygpnpcpqqa sypdptqetw gefpshsgly pgpkalggty
sqcprlehyg qvqvkpeqgc pvgsdstgla pclnahpseg
pphpqplfsh ypgpsppqyl qsgpytqppp dylpseprpc
ldfdspthst gqikaqlvcn yvqsqqellw eggqredapa
qepsyqspkf lgdsqvspsr akapvntygp gfgpnlpnhk
sgsyptpspc henfvvganr ashraaappr llpplptcyg
plkvggtnps cghpevgrlg ggpalyppppe gqvcnpldsl
dldntqldfv aildepqgls pppshdqrgs sghtpppsgp
pnmavgnmsv llrslpgetq flnssa;
```

An exemplary human Gli2 sequence is:

```
                                        (SEQ ID NO: 14)
metsasatas ekqeaksgil eaagfpdpgk kasplvvaaa
aaaavaaqgv pqhllppfha plpidmrhqe gryhyephsv
hgvhgppals gspvisdisl irlsphpagp gespfnaphp
yvnphmehyl rsvhssptls misaarglsp advaqehlke
rglfglpapg ttpsdyyhqm tlvaghpapy gdllmqsgga
asaphlhdyl npvdvsrfss prvtprlsrk ralsisplsd
asldlqrmir tspnslvayi nnsrsssaas gsyghlsaga
lspaftfphp inpvayqqil sqqrglgsaf ghtpppliqps
ptflaqqpma itsinatptq lssssnclsd tnqnkqsses
avssstvnpva ihkrskvkte peglrpaspl altqgqvsgh
gscgcalpls qeqladaked ldrddckqea evviyetnch
wedctkeydt qeqlvhhinn ehihgekkef vcrwqactre
qkpfkaqyml vvhmrrhtge kphkctfegc skaysrlenl
kthlrshtge kpyvcehegc nkafsnasdr akhqnrthsn
ekpyickipg ctkrytdpss lrkhvktvhg pdahvtkkqr
ndvhlrtpll kengdseagt epggpestea sstsqavedc
lhvraiktes sglcqsspga qsscssepsp lgsapnndsg
vempgtgpgs lgdltalddt ppgadtsala apsagglqlr
khmttmhrfe qlkkeklksl kdscswagpt phtrntklpp
lpgsgsilen fsgsggggpa gllpnprlse lsasevtmls
qlqerrdsst stvssaytvs rrssgispyf ssrrsseasp
lgagrphnas sadsydpist dasrrsseas qcsggsglln
ltpaqqyslr akyaaatggp pptplpgler mslrtrlall
dapertlpag cprplgprrg sdgptyghgh agaapafphe
apgggarras dpvrrpdals lprvqrfhst hnvnpgplpp
cadrrglrlq shpstdggla rgaysprpps isenvameav
aagvdgagpe adlglpeddl vlpddvvqyi kahasgalde
```

-continued gtgqvyptes tgfsdnprlp spglhgqrrm vaadsnvgps apmlggcqlg fgapsslnkn nmpvqwnevs sgtvdalasq vkpppfpqgn iavvqqkpaf gqypgyspqg lqaspggldls tqphlqprsg apsqgiprvn ymqqlrqpva gsqcpgmttt msphacygqv hpqlspstis galnqfpqsc snmpakpghl ghpqqtevap dpttmgnrhr elgvpdsala gvppphpvqs ypqqshhlaa smsqegyhqv psllparqpg fmepqtgpmg vatagfglvq prpplepspt grhrgvravq qqlayaratg hamaampssq etaeavpkga mgnmgsvppq pppqdaggap dhsmlyyygq ihmyeqdggl enlgscqvmr sqppqpqacq dsiqpqplps pgvnqvsstv dsqlleapqi dfdaimddgd hsslfsgals psllhslsqp ssrlttprns ltlpsipagi snmavgdmss mltslaeesk flnmmt an exemplary N-myc mRNA sequence is:

>NM_008709.3 *Mus musculus* v-myc avian myelo-
cytomatosis viral related oncogene, neuroblastoma
derived (Mycn), mRNA (SEQ ID NO: 10)
AGTGACAGTCATCTGTCTGGACGCGCTGGGTGGATGCGGGGGGCTCCTGG

GAACTGGGTTGGAGCCAACGAGCGCTAGCCAGGCGTAAGCGCGCACACA

CTGCAGCCGCCGGAGGACAACCCCCTCCCGCCGCCGCTCCCTCAGCCCAC

CCGGAGACCCCAGCCCCGAGTCGCCTCCGGATCCCCGGCAGTCTGCGGGA

GAGTTGGAGGTTGGCGCGACTCTGCTGCTCTCCACGGGAAGGAAGCACTC

CCCCATATTAAAAAGAGCGGAGATATTAAAAGAGAGGCGAACCCATGCCC

AGCTGCACCGCGTCCACCATGCCGGGGATGATCTGCAAGAACCCAGACCT

CGAGTTTGACTCACTGCAGCCCTGCTTCTACCCGGACGAAGATGACTTCT

ACTTCGGCGGTCCCGACTCGACCCCACCGGGGAGGACATCTGGAAGAAG

TTTGAGCTGCTGCCCACGCCCCCGTTGTCGCCCAGCCGCGCCTTCCCAGA

GCACAGCCCGGAGCCTTCGAATTGGGCTACGGAGATGCTGCTGCCGGAGG

CCGACCTGTGGGGCAACCCGGCCGAGGAGGATGCGTTCGGTCTCGGGGC

CTGGGTGGCCTCACTCCTAATCCGGTCATCCTTCAGGACTGCATGTGGAG

CGGCTTCTCTGCCCGCGAGAAGCTAGAGCGCGCAGTGAACGAAAAACTAC

AGCACGGCCACGGGCCCCCGGGCGTCAGCTCAGCCTGCTCGGCTCCCGGA

GTGGGTGCCAGCAGCCCCGGGGCCGTGCCCTTGGTGGGTCGTCGAGTGC

TAGCCACACCGGGGCCACCCTGCCTACCGACCTCTCCCACCCGGCTGCCG

AATGTGTGGACCCCGCCGTGGTCTTCCCCTTCCCGGTGAACAAGCGAGAG

TCGGCGTCGGTGCCCGCTGCCCCACTAGCGCCCGGCGACCAGCGCTGC

GGTCACTAGTGTGTCTGTTCCAGCTACTGCCCCGGTGGCTGCTCCTGCTC

GTGCAGGCGGCCGTCCTGCCAGCAGTGGGGAGGCCAAGGCCCTCAGCACC

TCCGGAGAGGATACCTTGAGCGACTCAGATGATGAGGATGACGAGGAGGA

AGATGAAGAGGAGGAAATCGATGTGGTCACCGTAGAGAAGAGACGTTCCT

CCTCTAACAACAAGGCGGTAACCACTTTCACGATCACTGTGCGTCCCAAG

ACCTCCGCTCTGGGCCTGGGGCGAGCACAGCCTGGCGAGCTGATCCTCAA

GCGCTGTGTTCCCATCCATCAGCAGCACAACTATGCTGCACCCTCACCCT

ACGTGGAGAGCGAGGACGCGCCCCCGCAGAAAAAGATCAAGAGCGAGGCT

TCTCCACGCCCCCTCAAAAGTGTTGTTCCAGCAAAAGCGAAGAGCCTGAG

CCCCCGAAACTCAGACTCGGAGGACAGCGAGCGCCGCCGCAACCACAACA

TCCTGGAGCGTCAACGCCGGAACGACCTGCGCTCCAGCTTCCTGACGCTC

AGGGACCATGTGCCTGAGCTGGTGAAGAACGAGAAGGCCGCCAAGGTGGT

CATCTTGAAAAAGGCCACCGAGTACGTGCACGCCCTACAGGCCAACGAGC

ACCAGCTCCTGCTGGAAAAGGAGAAACTGCAGGCGAGGCAGCAGCAGTTG

CTAAAGAAGATCGAACACGCTCGGACTTGCTAAACGTTTCCCACACGGAC

AGTCACTGCCACTTTGCACATTTTGATTTTTTTTTTTTTAAACAAACA

TTGTGTTGACATTAAGAATGTTGGTTTACTTTCAAATTGGTCCCCTGTCG

AGTCTGGATCTGGGTAGGGGGCAGGACACGGGGTCTGCCATGACCTTGG

AAAAAAAACTGACTTATGGGATGCTGGGTGGCTTGTTTTCCTCCTCCATA

TCACCTGGTGACAGCCGTGGAAGTTCGGGACACTAAGGAGCTTCAGGAGG

CTGTGAAGTCACCTTGTTCCGGTCCAAGATTCCAAACAGAGTCATTCCTT

CTTTTTACAATGGTGCTTAAGTTCCAGCAAATGCCACAGAAGGGGGGGTT

GCCATTTGATGCCCCTGGGAACACTTGTGTAAATACCATTGATACACCCC

CCTTTTGTATACGTCCTGGGTAATGAGAGGTGGCTCTTGCGGCCAGTATT

AGACTGGAAGTTCACACCTAAGTACTGTAAGAATACCTCAATGTTTGAGG

GGCATGTTTTGTATACAAATATATTGTTAATCTGTTATGTACTGTACTAA

TTCCTACACGGCCTGTATACTTTAGTATGACGCTGATACATAACTAAATT

TGATACTTATATTTTCGTATGAAAATGAGTTGTGGAAGTTTTGAGTAGAT

ATTACTTTATCACTTTTTGAACTAAGAAACTTTTGTAAAGAAATTTTACT

ATATATATATATTCCTTTTTTTCCTAGCCTGTTTCTTCCTTGTTTACTGT

ATTTGTTCATGTTTGGTGCATAGAACTGCGTAAAATGGCAAAGTTCTGTG

TTTAATTTCTTCAAAATGTATATATTTAGTGCTGCACCTTAGAGCACTTT

GAAATACCTCATGTTTATGAAAATAAATAGCAATTAAATGATGCAA an exemplary N-myc protein sequence is:

(SEQ ID NO: 5)
mpscststmp gmicknpdle fdslqpcfyp deddfvfggp dstppgediw kkfellptpp lspsrgfaeh sseppswvte mllenelwgs paeedafglg glggltpnpv ilqdcmwsgf sareklerav seklqhqrgp ptagstaqsp gagaaspagr ghggaagagr aqaalpaela hpaaecvdpa vvfpfpvnkr epapvpaapa sapaagpava sgagiaapag apgvapprpg grqtsggdhk alstsgedtl sdsddeddee edeeeeidvv tvekrrsssn tkavttftit vrpknaalgp graqsselil krclpihqqh nyaapspyve sedappqkki kseasprplk svippkaksl sprnsdseds errrnhnile rqrrndlrss

```
fltlrdhype lvknekaakv vilkkateyv hslqaeehql llekeklqar qqqllkkieh artc
``` an exemplary human N-myc protein sequence is:

```
                                            (SEQ ID NO: 15)
mpscststmp gmicknpdle fdslqpcfyp deddfyfggp dstppgediw kkfellptpp lspsrgfaeh sseppswvte mllenelwgs paeedafglg glggltpnpv ilqdcmwsgf sareklerav seklqhgrgp ptagstaqsp gagaaspagr ghggaagagr agaalpaela hpaaecvdpa vvfpfpvnkr epapvpaapa sapaagpava sgagiaapag apgvapprpg grqtsggdhk alstsgedtl sdsddeddee edeeeeidvv tvekrrsssn tkavttftit vrpknaalgp graqsselil krclpihqqh nyaapspyve sedappqkki kseasprplk svippkaksl sprnsdseds errrnhnile rqrrndlrss fltlrdhvpe lvknekaakv vilkkateyv hslqaeehql llekeklqar qqqllkkieh artc.
```

Peptides, Polypeptides and Fusion Proteins

The peptide or fusion proteins can be synthesized in vitro, e.g., by the solid phase peptide synthetic method or by recombinant DNA approaches (see above). The solid phase peptide synthetic method is an established and widely used method. These polypeptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, chemically modified derivatives of a given peptide or fusion thereof, can be readily prepared. For example, amides of the peptide or fusion thereof of the present disclosure may also be prepared by techniques well known in the art for converting a carboxylic acid group or precursor, to an amide. One method for amide formation at the C-terminal carboxyl group is to cleave the peptide or fusion thereof from a solid support with an appropriate amine, or to cleave in the presence of an alcohol, yielding an ester, followed by aminolysis with the desired amine.

Salts of carboxyl groups of a peptide or fusion thereof may be prepared in the usual manner by contacting the peptide, polypeptide, or fusion thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or fusion thereof may be prepared by utilizing an N-acyl protected amino acid for the final condensation, or by acylating a protected or unprotected peptide, polypeptide, or fusion thereof. O-acyl derivatives may be prepared, for example, by acylation of a free hydroxy polypeptide; or polypeptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide. Other amino-terminal modifications include aminooxypentane modifications.

In one embodiment, a polypeptide or fusion polypeptide has substantial identity, e.g., at least 80% or more, e.g., 85%, 87%, 90%, 92%, 95%, 97%, 98%, 99% and up to 100%, amino acid sequence identity to one of SEQ ID NOs. 1-5 or 12-15, or a portion thereof having cardiac repair or regeneration activity.

Substitutions may include substitutions which utilize the D rather than L form, as well as other well known amino acid analogs, e.g., unnatural amino acids such as α, α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

Conservative amino acid substitutions may be employed—that is, for example, aspartic-glutamic as acidic amino acids; lysine/arginine/histidine as polar basic amino acids; leucine/isoleucine/methionine/valine/alanine/proline/glycine non-polar or hydrophobic amino acids; serine/threonine as polar or hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting peptide, polypeptide or fusion polypeptide. Whether an amino acid change results in a functional peptide, polypeptide or fusion polypeptide can readily be determined by assaying the specific activity of the peptide, polypeptide or fusion polypeptide.

Amino acid substitutions falling within the scope of the disclosure, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The disclosure also envisions a peptide, polypeptide or fusion polypeptide with non-conservative substitutions. Non-conservative substitutions entail exchanging a member of one of the classes described above for another.

Acid addition salts of the peptide, polypeptide or fusion polypeptide or of amino residues of the peptide, polypeptide or fusion polypeptide may be prepared by contacting the polypeptide or amine with one or more equivalents of the desired inorganic or organic acid, such as, for example, hydrochloric acid. Esters of carboxyl groups of the polypeptides may also be prepared by any of the usual methods known in the art.

Routes and Formulations

Administration of compositions according to the disclosure can be via any of suitable route of administration, particularly parenterally, for example, orally, intranasal, intravenously, intra-arterially, intraperitoneally, intrathecally, intraventricularly, intraurethrally, intrasternally, intracranially, intramuscularly, intracardiacly, or subcutaneously. Such administration may be as a single dose or multiple doses, or as a short- or long-duration infusion. Implantable devices (e.g., implantable infusion pumps) may also be employed for the periodic parenteral delivery over time of equivalent or varying dosages of the particular formulation. For such parenteral administration, the therapeutic agent may be formulated as a sterile solution in water or another suitable solvent or mixture of solvents. The solution may contain other substances such as salts, sugars (particularly glucose or mannitol), to make the solution isotonic with blood, buffering agents such as acetic, citric, and/or phosphoric acids and their sodium salts, and preservatives.

The compositions alone or in combination with other active agents can be formulated as pharmaceutical compositions and administered to a vertebrate host, such as a human patient in a variety of forms adapted to the chosen route of administration, e.g., orally or parenterally, by intravenous, intramuscular, topical or subcutaneous routes.

Thus, the compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the vertebrate's diet. For oral therapeutic administration, the composition optionally in combination with another active compound may be combined with one or more excipients and used in the form of ingestible tablets, buccal tablets, troches, capsules, elixirs, suspensions, syrups, wafers, and the like. Such compositions and preparations should contain at least 0.1% of active agent. The percentage of the compositions and preparations may, of course, be varied and may conveniently be between about 2 to about 60% of the weight of a given unit dosage form. The amount of the agent and optionally other active compound in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active agent, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the agent optionally in combination with another active compound may be incorporated into sustained-release preparations and devices.

The composition optionally in combination with another active compound may also be administered intravenously or intraperitoneally by infusion or injection. Solutions of the agent(s) optionally in combination with another active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of particle size in the case of dispersions or by the use of surfactants. The prevention of the action of microorganisms during storage can be brought about by various antibacterial and antifungal agents, for example, parabens, chlorobutanol, phenol, sorbic acid, thimerosal, and the like. In many cases, it may be useful to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating agent(s) in the required amount in the appropriate solvent with various of the other ingredients enumerated above, followed by filter sterilization. In the case of sterile powders for the preparation of sterile injectable solutions, one method of preparation includes vacuum drying and the freeze drying techniques, which yield a powder of the active ingredient plus any additional desired ingredient present in the previously sterile-filtered solutions.

For topical administration, the agent(s) optionally in combination with another active compound may be applied in pure form, e.g., when they are liquids.

Useful solid carriers include finely divided solids such as talc, clay, microcrystalline cellulose, silica, alumina and the like. Useful liquid carriers include water, alcohols or glycols or water-alcohol/glycol blends, in which the present agents can be dissolved or dispersed at effective levels, optionally with the aid of non-toxic surfactants. Adjuvants such as fragrances and antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In addition, in one embodiment, the disclosure provides various dosage formulations of the agent(s) optionally in combination with another active compound for inhalation delivery. For example, formulations may be designed for aerosol use in devices such as metered-dose inhalers, dry powder inhalers and nebulizers.

Useful dosages can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the agent(s) optionally in combination with another active compound in a liquid composition, may be from about 0.1-25 wt-%, e.g., from about 0.5-10 wt-%. The concentration in a semi-solid or solid composition such as a gel or a powder may be be about 0.1-5 wt-%, e.g., about 0.5-2.5 wt-%.

The active ingredient may be administered to achieve peak plasma concentrations of the active agent of, in one embodiment, from about 0.5 to about 75 µM, e.g., about 1 to 50 µM, such as about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the agent(s) optionally in combination with another active compound, or an active salt or derivative thereof, for use in treatment may vary not only with the particular salt selected but also with the route of administration, the nature of the condition being treated and the age and condition of the patient and will be ultimately at the discretion of the attendant physician or clinician. In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for instance in the range of 6 to 90 mg/kg/day, e.g., in the range of 15 to 60 mg/kg/day.

The agent(s) optionally in combination with another active compound may be conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The dose, and perhaps the dose frequency, will also vary according to the age, body weight, condition, and response of the individual vertebrate. In general, the total daily dose range for an active agent for the conditions described herein, may be from about 1 mg to about 100 mg, from about 10 mg to about 50 mg, from about 10 mg to about 40 mg, from about 20 mg to about 40 mg, from about 20 mg to about 50 mg, from about 50 mg to about 5000 mg, in single or divided doses. In one embodiment, a daily dose range should be about 100 mg to about 4000 mg, e.g., about 1000-3000 rug, in single or divided doses, e.g., 750 mg every 6 hr of orally administered agent.

For viral vectors, a dose of the viral vector may be about $1 \times 10^{11}$ to about $1 \times 10^{16}$ genome copies, about $1 \times 10^{12}$ to about $1 \times 10^{15}$ genome copies about $1 \times 10^{11}$ to about $1 \times 10^{13}$ genome copies, or about $1 \times 10^{13}$ to about $1 \times 10^{15}$ genome copies.

The invention will be further described by the following non-limiting examples.

Example I

Methods

All animal handling and experimental procedures were approved by the Institutional Animal Care and Use Committee of the University of Minnesota. All experiments were repeated at least three times and the data represent the mean±SEM. Statistical significance was determined using the Student's t-test and one-way ANOVA (non-parametric) test and a p-value<0.05 was considered a statistically significant change.

Newt Husbandry and Heart Resection Surgery

All experiments were performed according to the University of Minnesota IACUC guidelines. Adult red-spotted newts, *Notophthalmus viridescens*, were housed as described in Singh et al. (2012). For heart resection surgery, adult newts were anesthetized in 0.1% MS-222 solution for 10 min. Each newt was placed in a supine position under a stereomicroscope. The outer skin was wiped using 70% ethanol-chlorhexidine solution and the pericardial sac was opened to expose the heart. The apex of the ventricle was resected (~25-30%) using iricdectomy scissors. Following resection, the blood flow was controlled by the formation of the blood clot. The resected heart was maneuvered carefully into the pericardial sac and sutured using 8.0 ethilon monofilament sutures. Following resection surgery, newts were allowed to recover in an isolated tank containing sulfmerazine antibiotic solution and later placed in their designated aquariums. The resected ventricular mass was measured using a Sartorius weighing balance. Cyclopamine (CyA; LC laboratories) was dissolved in 100% ethanol to a stock concentration of 10 mg/ml. CyA-mediated inhibition of HH signaling was achieved by daily treatment of the resected newts at 2 µg/mL diluted in the aquarium water. At specified time periods, animals were sacrificed and tissues were collected for further processing. For EdU labelling, the resected newts were injected intraperitoneally (i.p.) with 100 µg/gm of EdU for a 7 day period prior to sacrifice and harvested for immunohistochemical analysis.

Echocardiography

Newts were anesthetized using a 0.1% MS-222 solution and echocardiograms were obtained by placing the probe adjacent to the pericardial sac using a Vevo2100 echocardiographic machine. Diastolic and systolic dimensions were measured in a blinded fashion and the average values were used to calculate the fractional shortening at each time point. Echocardiographic analyses were performed using multiple newts for each time period.

Histology and Immunohistochemistry

For histological analysis, animals were euthanized at specified time periods and tissues were fixed in 4% paraformaldehyde. Histological sectioning, hematoxylin-eosin (H & E) staining and Masson Trichome staining were performed as described in Singh et al. (2012). Immunohistochemistry was performed on cryosections (10 μm thick) using standard procedures (Singh et al., 2012; Singh et al. 2007; Adhikari et al., 2011; Singh et al., 2010). Briefly, sections were rehydrated, permeabilized and blocked with 10% normal donkey serum (NDS), 0.1% Triton X-100 in PBS at room temperature and incubated overnight at 4° C. with primary antibodies: α-actinin (Abeam; 1:300), desmin (Novus biologicals; 1:300), Shh (Santa Cruz Biotechnology; 1:200), endomucin (Abeam; 1:100), SM22 (Abeam; 1:400), α-phospho-Histone H3 (Ser10) (Millipore; 1:100), Ki67 (Abcam; 1:200), PCNA (Santa Cruz Biotechnology; 1:100), Mef2a (Santa Cruz Biotechnology; 1:100), Smoothened (Abcam; 1:200), Nkx 2-5 (Santa Cruz Biotechnology; 1:100) and GFP (ThermoFisher Scientific; 1:300) sera. Sections were rinsed and incubated with combinations of secondary antibodies (1:400) including Alexa 488, Alexa 594, Cy3 and Cy5 (Jackson ImmunoResearch Laboratories). EdU staining was performed using the EdU labeling kit (Life Technologies)

Genetic Mouse Models

All experiments were performed according to the University of Minnesota IACUC guidelines. To activate HH signaling in a cardiomyocyte-specific fashion, the αMHC:CreERT2 (MerCreMer) mouse strain was crossed with Rosa26-SmoM2-YFP$^{fl/+}$ mice (Jeong et al., 2004). Injection of 4-hydroxy tamoxifen led to constitutive expression of the Smo/EYFP fusion gene and unrestrained HH signaling in the Cre-expressing tissues. To delete Smoothened (Smo CKO), the αMHC:CreERT2;Smo$^{L/L}$ mouse model was crossed with the Smo-floxed (Smo$^{L/L}$) mouse lines and then neonates were subcutaneously injected 4-hydroxytamoxifen (80 μg/gm) at P0/P1 stage. For the late juvenile stage, 4-hydroxytamoxifen was injected in neonates at P0, P3 and P6. Control and SmoM2-YFP$^{fl/+}$ mice received intraperitoneal (i.p.) injections of EdU (25 μg/g) daily until P7. For the late juvenile stage, EdU injections were delivered every 3 days from P11 to P28. Heart tissues were excised following perfusion using 30 mM KCl solution followed by phosphate-buffer saline perfusion. Excised heart tissues were immersion-fixed in 4% paraformaldehyde overnight at 4° C., and rinsed in cold PBS and processed for cryo sectioning.

Myocardial Infarction and Echocardiography

Myocardial infarctions in neonatal (P2), juvenile (P7) and adult (P66) mice were performed by ligation of the left anterior descending coronary artery (Mahmoud et al., 2013; Collesi et al., 2008). Neonates and P7 mice were anaesthetized by cooling on an ice bed for 1-2 min. Lateral thoracotomy at the fourth intercostal space was achieved by blunt dissection of the intercostal muscles following skin incision. A tapered needle (C-1) attached to a 6-0 prolene suture (Ethicon) was passed through the midventricle below the origin of the left anterior descending coronary artery (LAD) and ligated to induce myocardial infarction (MI). Following ligation, thoracic wall incisions were sutured with 6.0 nonabsorbable silk sutures, and the skin wound was closed. Pups were then warmed under a heat lamp for several minutes until recovery and injected with buprenorphine-SR (i.m.). Adult LAD ligation experiments were performed (D'Uva et al., 2015). Briefly, hair was removed from the surgical site and disinfected with 70% isopropyl alcohol and povidone iodine solution. Adult mice were anesthetized with inhaled 2-5% isofluorane and intubated to the level of the carina and an adequate level of anesthesia was maintained using a Harvard ventilator. Using sterile procedures, a thoracotomy was performed to expose the heart and the proximal left anterior descending coronary artery was permanently ligated below the middle region of the heart to obtain moderate injury using 6-0 silk sutures. The thoracic wall was closed using 3-0 silk sutures and the mice were extubated. After LAD ligation injury, mice were maintained on a heating platform (37° C.) and continuously monitored until they were fully recovered and ambulating about the cage. The hearts were collected for analysis at the designated end points. For echocardiography, conscious mice were restrained in a supine position and echocardiograms were obtained by placing the probe adjacent to the pericardial sac using a Vevo2100 machine.

RNA Isolation and qPCR

RNA isolation and qPCR analysis from newt tissue was performed as previously described[5]. For chamber based qPCR analysis, the regenerating heart including BA, AT and ventricle was harvested and rinsed in PBS to remove blood cells. Subsequently, the BA, AT and ventricle were collected from heart tissue (n=12) for further processing. RNA isolation from cultured cardiomyocytes was performed using a standard protocol as per the manufacturer's instructions. Total RNA was isolated using the miRVANA kit (Ambion) and cDNA was made using SuperScript Reverse Strand Synthesis-III kit (Invitrogen).

Wheat Germ Agglutinin (WGA) Staining

Cryosections were rinsed 3 times in PBS and incubated with a primary antibody against WGA conjugated to Alexa Fluor 488 (50 μg/mL, Invitrogen, Calif.) for 1 hour at room temperature. Slides were then rinsed in PBS and DAPI staining was performed for 10 min and mounted with Vectashield mounting medium (Vector Labs, Calif.). Stained tissues were imaged using a LSM 510 meta confocal microscope and images were processed using Photoshop CS6 software.

Lineage Tracing Studies

For lineage tracing, the αMHC:CreERT2 mouse strain was crossed with Rosa26-SmoM2/YFP mice. To lineage label the pre-existing cardiomyocytes, 4-hydroxytamoxifen was injected in neonates at P0, P3 and P6 prior to MI. Following TM-injection, all the cardiomyocytes express EGFP and were labelled green. Control and SmoM2-YFP$^{fl/+}$ mice received intraperitoneal injections of EdU (25 μg/g) and sacrificed at the time periods described. Immunohistochemical techniques were performed to detect the lineage-labeled cells as described above.

Mouse Ventricular Cardiomyocyte Isolation

Ventricular cardiomyocytes were isolated using previously published protocols (Collesi et al. 2008). Briefly, ventricles were dissected from P1 pups, minced in CBFHH (calcium and bicarbonate-free Hanks with Hepes) buffer. Subsequently, the minced ventricles were digested in CBFHH buffer containing 1.75 mg/ml of trypsin and 20 μg/ml of DNaseII (Sigma-Aldrich). Cells were preplated for 1 h (3 times) onto 100-mm primaria (Corning Life Sciences) dishes in culture medium containing 10% serum to remove fibroblasts. Unattached cardiomyocytes were plated at a desired density. Using this protocol, we routinely obtained >85-90% cardiomyocytes (confirmed using immunohistochemical techniques and an alpha-actinin antibody). After 12 h, the culture medium was changed and cells were subjected to the different treatments (SAG; 4 μg/mL and CyA; 5 μg/ml) and analyzed. For apoptotic pathway inhibition, neonatal cardiomyocytes were treated with cell permeable small molecule inhibitor (Z-VAD-FMK; R&D Systems) with or with SAG. For the EdU incorporation assay, cardiomyocytes were incubated with 20 μM EdU for 48 h and fixed using 4% PFA for 10 min at room temperature. P7 cardiomyocytes were isolated using a similar protocol as that of the P1 cardiomyocyte isolation protocol with modifications including the perfusion based tissue digestion using collagenase type-2 enzyme solution. >95% rod-shaped binucleated cardiomyocytes were routinely obtained using this protocol. For qPCR and FACS analysis, cells were harvested using trypsin and processed for further analysis. For the time-lapse microscopic experiments, isolated P7 mCherry+ cardiomyocytes were plated on glass-bottom petri dish coated with fibronectin. After 2 h of attachment, media was changed containing DMSO or SAG and the petri dish was placed in the environmental chamber for imaging. Adult cardiomyocyte isolation was performed (Mahmoud et al., 2013). Briefly, the adult heart tissue was dissociated by perfusion of a collagenase type 2 enzyme solution. Isolated cardiomyocytes were cultured in 1% serum media in the presence of DMSO or SAG. For the EdU incorporation assay, cardiomyocytes were incubated with 20 μM EdU for 48 h and fixed using 4% PFA for 10 min at room temperature.

Synthesis and Transfection of Mycn and Gfp mRNAs

PCR products with T7 promoter site in the 5' end for Mycn (Primers: Mycn T7 sense: TAATACGACTCAC-TATAGGGCACCATGCCCAGCTGCACCGCGTC (SEQ ID NO:21), Mycn reverse: TTAGCAAGTCCGAGCGTGTTCGAT (SEQ ID NO:22)) and GFP (Primers: GFP T7 forward: AATACGACTCAC-TATAGGGCACCATGAGCGGGGGCGAGGAGCTG (SEQ ID NO:23), GFP reverse: TTATCT-GAGTCCGGACCTGTACAG (SEQ ID NO:24)) coding sequences were amplified from respective plasmids (Mycn: Origene; MR207382L2, Gfp:Origene; TR30023). PCR products were purified and 500 ng was used as template for the in vitro synthesis of translation enhanced capped transcripts using the mMESSAGE mMACHINE T7 Ultra Kit (ThermoFisher #AM1345). The capped transcription reaction was performed at 37° C. for 14 hours followed by the poly(A) tailing reaction. RNA was recovered using the mirVana miRNA isolation kit (ThermoFisher #AM1560). 1.5 ug of purified RNA was used for transfection experiment using the isolated adult cardiomyocytes.

Lentiviral Constructs and Infection

Lentiviral particles to overexpress Gli1 (Origene; M2270231L2), Mycn (Origenes; MR207382L2) were generated using standard protocols. To knockdown Gli1 and Mycn, four unique 29-mer shRNA were obtained for Gli1 (Origene; TL500820) and Mycn (Origene; TL514180) and each of them tested using transient transfection assays in C2C12 myoblasts. The most efficient constructs were used to generate lentiviruses using standard protocols ((Tiscornia et al., 2006). Cultured cardiomyocytes were infected with lentiviruses using Lentiblast reagent (OZBiosciences) as per the manufacturer's instruction. After 12 h of infection, cells were washed twice using pre-warmed culture medium and EdU (20 μM) was added for an additional 36 h time period. Cells were fixed using 4% PFA for 10 min at room temperature and processed as described above using immunocytochemistry and qPCR techniques.

hiPSC Differentiation

The hiPSC differentiation protocol was adapted from the protocol described by Zhang et al (2012) with slight modifications. Briefly, cultured hiPSCs were plated on matrigel containing RPMI/B27 minus insulin, Actinin A and CMIR-99021 for one day. The media was then changed with RPMI/B27 minus insulin and BMP4 and FGF from d1-d2. On d3, the medium was changed with RPMI/B27 minus insulin and IWP-4. The differentiated cells were maintained in RPMI/B27 with insulin media from d5-d60. Beating cardiomyocytes were observed by day 10 of differentiation. For HH signaling activation and inhibition, the differentiation medium was changed containing SAG and CyA together with EdU (20 μM) for 48 h. Immunohistochemical analysis was performed as described previously.

Bootstrap-Based Gene Set Analysis

The microarray dataset consisting of 18,560 genes and 9 time points (2 hours, 6 hours, 24 hours, 48 hours, 4 days, 7 days, 14 days, 21 days and 35 days) from the regenerating newt heart following injury was downloaded from Newt-Omics (see, e.g., newt-omics.mpi-bn.mpg.de). For each gene, the expression levels across all M time points were scaled to a mean of zero and standard deviation of one. To examine whether a gene set. S with the size of |S| is dynamically expressed postinjury, the Euclidean distance was computed between the mean expression profile of genes in set S, and the background expression profile, that is, the mean expression of all genes, as d. To generate a null distribution for d, the distance was computed between the mean expression profile of randomly sampled |S| genes and the background expression profile, and repeated 1,000 times. The bootstrapped distribution of the distance to background expression profile was represented as $d^0$. Thus, the p-value was computed as:

$$\frac{\sum_{n=1}^{1000} H(d_n^0 > d) + 1}{1000 + 1}$$

where $H(x)=1$, if $x>0$, otherwise 0. The significantly changed gene sets with an adjusted p-value<0.05 are reported.

ChIP-PCR Assay

The ChIP-PCR assay for endogenous Gli1 was performed (Singh et al., 2015). Briefly, the cultured neonatal cardiomyocytes were harvested in lysis-buffer and the DNA-protein complex was immunoprecipitated using biotinylated anti-Gli1 antibody (R&D Systems), followed by streptavidin-conjugated magnetic beads. PCR was performed to detect the target region using the following primers; Fwd: 5'-CTTCGCAAGTACCGCTTC-3' (SEQ ID NO:16); Rev: 5'-ATATCCCCCGAGCTTCAA-3' (SEQ ID NO:17).

Results

Figure 1B:
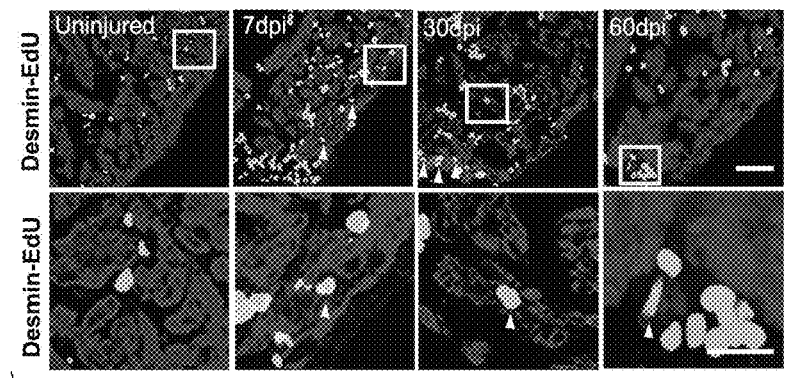
Figure 1C:
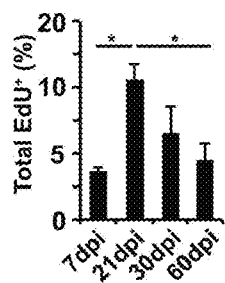

HU Signaling is Induced Upon Injury and is Essential for Heart Regeneration In Vivo Multiple lines of evidence support the conclusion that the adult newt harbors a tremendous regenerative capacity following cardiac injury (Singh et al., 2010; Witman et al., 2011; Borchart et al., 2010). To identify signaling networks during cardiac regeneration, ventricular apical resection studies were performed in the adult newt and its regenerative properties defined. The analysis revealed complete cardiac regeneration with functional restoration of the resected (~25-30%) heart by 60 days post-injury (dpi) (10a-c). Initial histological examinations revealed mitotic cardiomyocytes in the regenerating newt heart tissue following apical resection injury (FIG. 1A). An EdU-incorporation experiment labeled proliferating cardiomyocytes (desmin$^+$-EdU$^+$ cells) throughout the regenerating newt heart (FIG. 1B,C). Quantitative analysis revealed desmin$^+$-EdU$^+$ cardiomyocytes in the injured zone (20±3%), border zone (6±1%) and remote zone (2.5±0.5%) of the total cardiomyocyte pool at 21 dpi (FIG. 1B,C and FIG. 10D), suggesting a global regenerative response following resection injury.

Figure 1D:
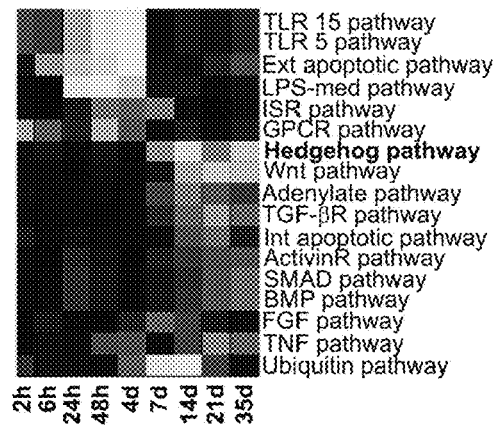
Figure 1E:
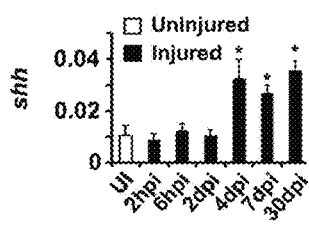
Figure 10F:
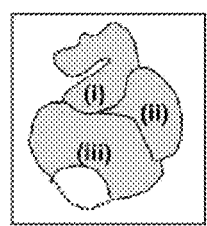
Figure 10G:
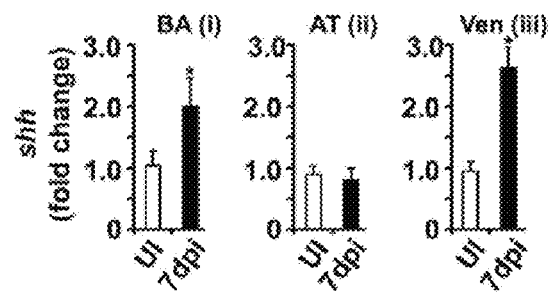
Figure 10H:
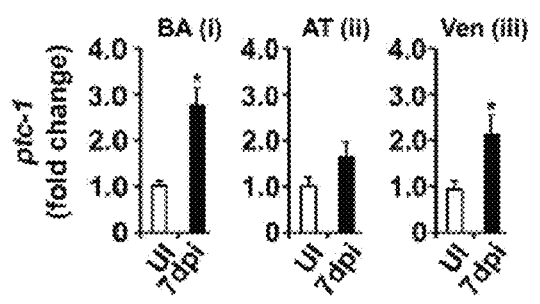
Figure 11A:
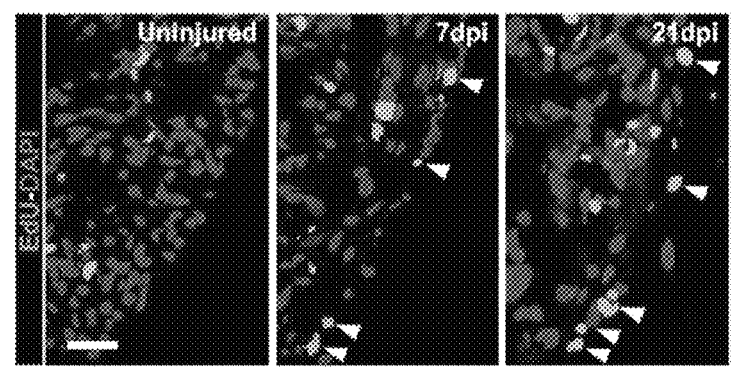
FIGS. 11A-11C. HH signaling modulated epicardial cells following apical resection injury. (A) Immunohistochemical analysis of the EdU$^+$ cells in the regenerating newt heart from uninjured, 7 dpi and 21 dpi heart tissue. The white arrowheads indicate the EdU$^+$ cells in the outermost layer of the section. (B,C) Immunohistochemical staining (B) and quantification (C) of Wt1$^+$-EdU$^+$ epicardial cells in the regenerating heart from control and CyA-treated newts at the designated time periods following injury (n=4). White arrowheads indicate the Wt1$^+$-epicardial cells following injury. Quantitative analysis represents counts from four different fields at 20× magnification from four replicates. Data represent mean±SEM (*p<0.05) and scale bars=100 µm (Panel A) and 50 µm (Panel B).
Figure 11B:
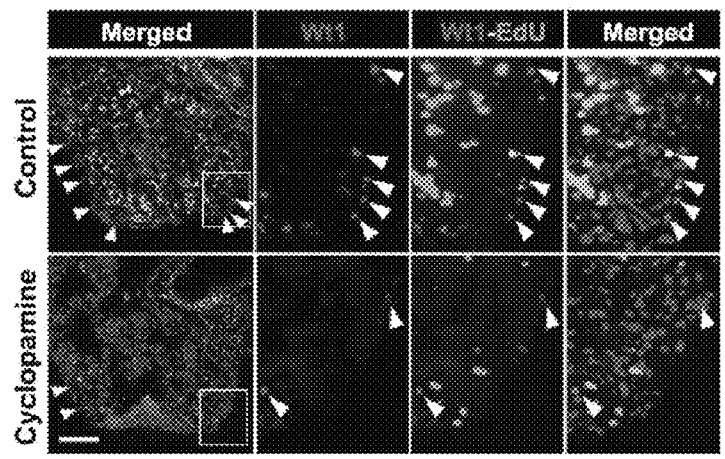
Figure 11C:
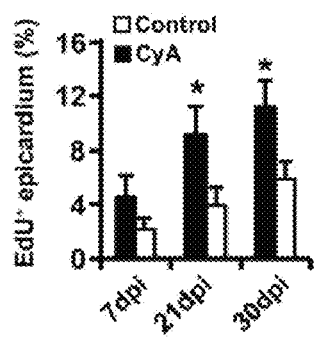

To investigate and define the molecular signals regulating regeneration, the Bootstrap bioinformatics tool was used, and the microarray datasets (Borchardt et al., 2010) (see. e.g., newt-omics.mpi-bn.mpg.de) from the regenerating newt heart analyzed at selected time periods following apical resection injury. Gene set enrichment analysis showed two distinct phases of response to injury. Multiple inflammatory pathways were upregulated during the early regenerative period (FIG. 1D and FIG. 10E). By 7 dpi, inflammatory signals were down-regulated with the subsequent activation of multiple signaling pathways including the hedgehog (HH) signaling pathway (FIG. 1D and FIG. 10E). HH signals were sustained throughout the later stages of regeneration (FIG. 1D). To validate these results, we performed qPCR using RNA isolated from the regenerating heart at selected time periods. Consistent with the Bootstrap analysis, the gene encoding the ligand of the HH pathway, shh, and the HH target, and co-receptor Patched, ptc-1, were both upregulated at 4 dpi and had sustained expression in the regenerating heart (FIG. 1E,F). Further, qPCR using RNA isolated from the bulbous arteriosus [BA (i)], atrial [AT (ii)], and ventricular [Ven (iii)] tissues, showed maximal expression of shh and ptc-1 levels in the injured ventricle and BA (FIG. 10F-H). These results supported the notion that the HH signaling pathway was important for cardiac regeneration.

Figure 1G:
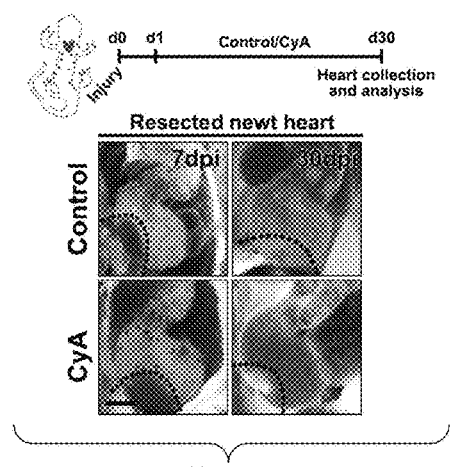
Figure 1F:
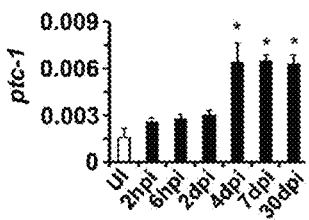
Figure 1H:
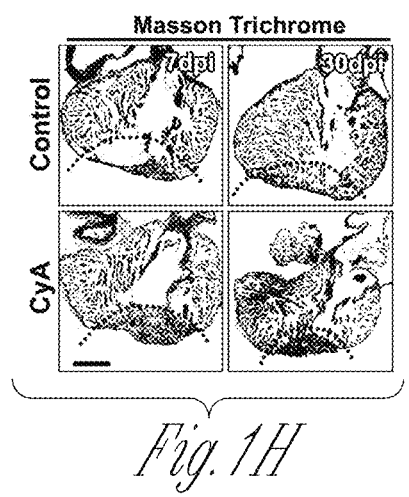
Figure 1I:
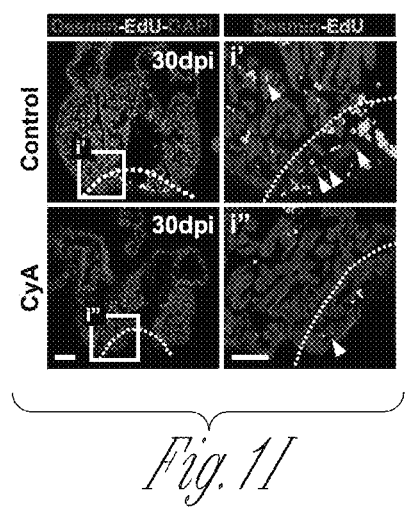
Figure 1J:
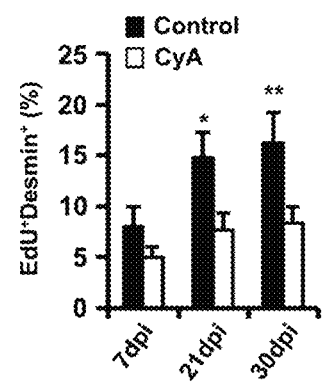

The hypothesis that HH signaling was essential for newt heart regeneration was tested by ablating HH signals in vivo using a potent Smoothened (Smo) antagonist, cyclopamine (CyA) (Chen et al., 2002). Continuous blockade of HH signals led to complete ablation of heart regeneration and induction of scar formation following injury (n=8, p<0.05) (FIG. 1G-1H). To further characterize the perturbed regeneration upon HH signalling inhibition, cellular proliferation was examined using an EdU-labeling assay at multiple time periods following ventricular resection. The EdU incorporation assay showed a 2-fold reduction in cardiomyocyte proliferation upon inhibition of HH signaling at 21 dpi and 30 dpi (n=6; p<0.05 and p<0.01, respectively) (FIG. 1I-J). Next, it was evaluated whether other lineages including epicardial cells were involved during the heart regenerative response and whether HH signaling impact these populations during regeneration. These results showed the necessity of HH signaling for heart regeneration in the newt following injury. These studies were further supported by others demonstrating the permissive role of signaling pathways on the epicardium and cardiovascular lineages in the regenerating zebrafish heart (Choi et al., 2013).

Activation of HH Signaling Promotes Mouse Neonatal Cardiomyocyte Proliferation In Vitro During mouse embryonic development, HH signaling coordinates cardiac progenitor proliferation, specification and coronary vascular development (Zhang et al., 2001; Washington et al., 2005). This ligand-receptor pathway includes hedgehog ligands (Shh, Ihh, Dhh) and membrane receptors [Smoothened (Smo) and Patched1 (Ptc1)] to regulate the downstream effectors (Singh et al., 2015; Robbins et al., 2012). While global deletion of Smo as well as $Shh^{-/-}/Ihh^{-/-}$ results in embryonic lethality due to cardiovascular defects (Zhang et al., 2001), its role in the postnatal proliferative myocardium and the perinatal regenerative period is unknown. To analyze the expression of HH signaling in the postnatal heart, qPCR was performed using RNA isolated from P1-P28 mouse hearts. qPCR analysis using P1 ventricular tissue revealed robust expression of the HH pathway transcripts, Smo and Ptc1, and cell cycle transcripts, Ccnd1, Ccnd2, and Ccne1. All of these transcripts were subsequently downregulated by P28 (FIG. 2A). In contrast, the cell cycle repressor gene, Cdkn1b, was upregulated between the P7-P28 period compared to P1 (FIG. 2A). The reduction in Smo, Ptc1, Ccnd1, Ccnd2, and Ccne1 transcripts during the first week of postnatal development indicated concomitant downregulation of HH signaling and the proliferative program as the heart loses its regenerative potential.

To assess the role of HH signaling in the regenerating neonatal mouse heart, immunohistochemical analysis of Shh and Smo was performed in postnatal day 1 (P1) heart tissue sections. Shh was strongly expressed in the non-myocyte cellular pool, including the endothelium ($Shh^+$-Endomucin$^+$ cells) and smooth muscle cells ($Shh^+$-SM22$^+$ cells) (FIG. 2B). Furthermore, immunohistochemical analysis of Shh and Desmin demonstrated an absence of co-labelled cells, suggesting that Shh was not expressed in cardiomyocytes (FIG. 2B). In contrast, the immunohistochemical analysis of Smo and Actinin revealed a punctate expression of Smo in Actinin-positive cardiomyocytes ($Smo^+$-Actinin$^+$ cells) as well as strong expression in the non-myocyte cellular ($Smo^+$-Actinin$^-$ cells; white arrow) pool (FIG. 2B). Further the analysis showed an uniform staining of Smo in these cardiomyocytes. To further verify the expression of Smo in the cardiomyocytes, qPCR analysis was undertaken using FACS-sorted αMHC-mCherry$^+$ cells (a transgenic cardiomyocyte specific promoter driving mCherry expression) from P1 hearts. qPCR analysis revealed a robust expression of the Smo transcripts in these mCherry$^+$ cells (FIG. 2C). Based on these results, it was hypothesized that a Shh morphogen secreted by the non-myocyte cellular pool signaled, in a paracrine manner, the adjacent Smo-expressing cardiomyocytes.

Figure 12A:
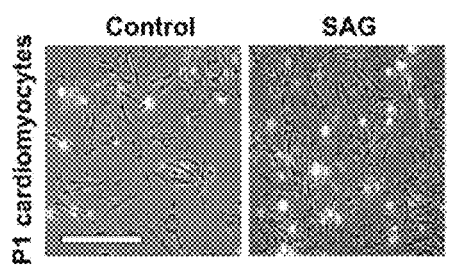
FIGS. 12A-12E. HH signaling regulates mouse neonatal cardiomyocyte proliferation. (A) Representative phase contrast image of control and SAG treated P1 cardiomyocytes. (B,C) qPCR analysis for Ptc1 and Ccne1 transcripts from control (white bar). SAG (grey bars) and CyA (black bars) treated neonatal cardiomyocytes (n=3 for each group). (D,E) Immunohistochemical (D) and quantitative analysis (E) of alpha-Actinin$^+$-EdU$^+$ cardiomyocytes from control (white bar) SAG (grey bar) and CyA (black bar)-treated isolated neonatal cardiomyocytes in serum-free conditions (n=3 for each group). Arrowheads indicate EdU$^+$-cardiomyocyte nuclei and arrows indicate EdU$^+$-nonmyocyte nuclei. Nuclei were stained with DAPI. Data in panels B, C and E represent mean±SEM (*p<0.05) and scale bars=200 µm.
Figure 12B:
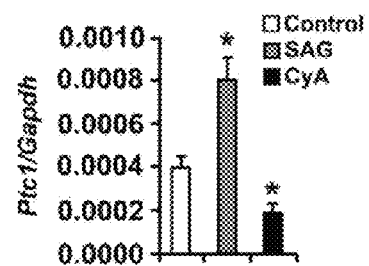
Figure 12C:
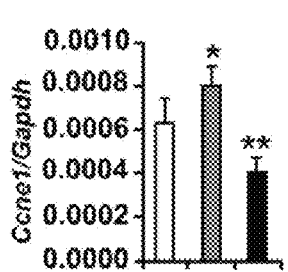
Figure 12D:
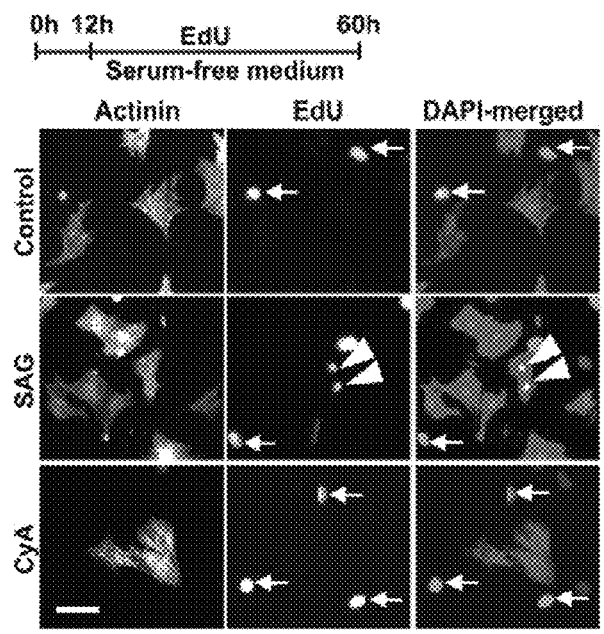
Figure 12E:
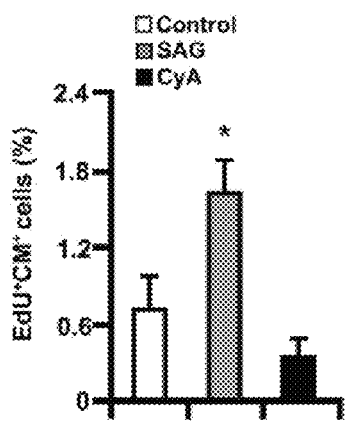
Figure 15A:
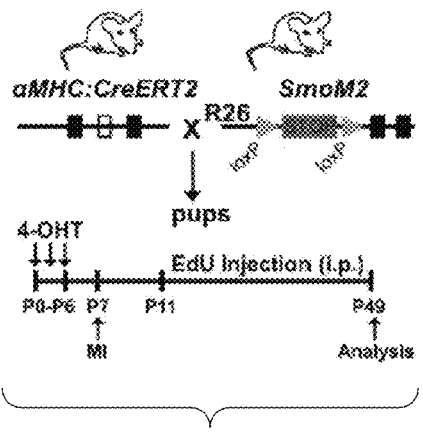
FIGS. 15A-15D. Induction of HH signaling pathway results in enhanced cardiomyocyte proliferation following injury. (A) Schematic outlining the experimental design for Smo activation and cardiac regeneration analysis following myocardial injury. (B) Immunostaining of Desmin$^+$-PCNA$^+$ cardiomyocytes and Desmin$^+$-pH3$^+$ cardiomyocytes in control and SmoM2 hearts at 42 days post-MI. Boxed regions in panel "B" are magnified in panels 1, 2, 3, 4, and 5. (C,D) Quantitative analysis of Desmin$^+$-PCNA$^+$ (C) and Desmin$^+$-pH3$^+$ cardiomyocytes (D) in control and SmoM2 hearts. Quantitation represents counts from four different fields at 20× magnification from three replicates. Data in panels C and D represent mean±SEM (*p<0.05) and scale bars=100 μm.
Figure 15C:
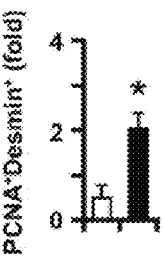
Figure 15D:
Figure 15B:
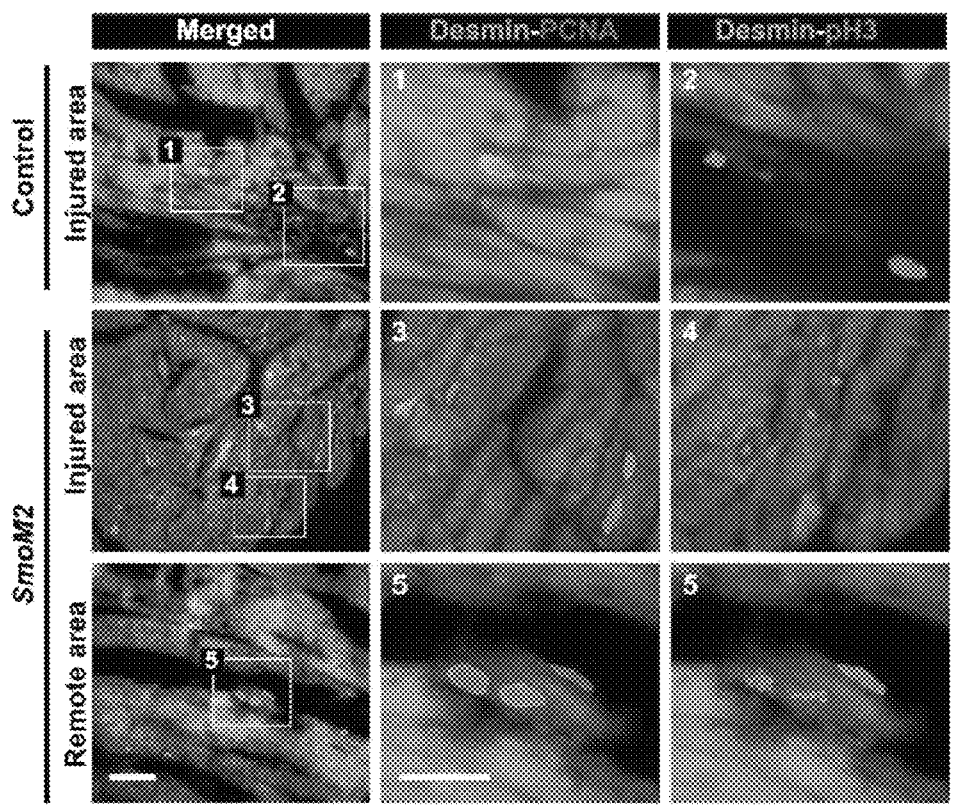

HH signaling activity was directly tested using small molecule-mediated activation and inhibition studies on isolated mouse neonatal cardiomyocytes. In vitro administration of the HH agonist (SAG) resulted in a dose-dependent increase in the number of cultured neonatal cardiomyocytes (FIG. 2D and FIG. 12A). Then an EdU-incorporation assay was performed to monitor the proliferation indices of the cultured neonatal cardiomyocytes. Compared to the controls, SAG treatment resulted in a 2.5-fold (n=4; p<0.05) increase in α-Actinin$^+$-EdU$^+$ cells. In contrast, cyclopamine (CyA)-mediated inhibition of HH signaling resulted in a significant decrease in cardiomyocyte proliferation (n=4; p<0.05) (FIG. 2E-F). To validate these EdU incorporation results, immunostaining for Ki67 was performed to examine the proliferating cardiomyocytes following treatment with DMSO, SAG, and CyA. Very few cardiomyocytes were stained for Ki67 (Ki67$^+$-Actinin$^+$ cells) in the controls, whereas, an increased number of Ki67$^+$-Actinin$^+$ cells was observed in the SAG-treated (n=3; p<0.05) cardiomyocytes. In contrast, Ki67$^+$-Actinin$^+$ cells were not detected in the CyA-treated groups (FIG. 2G-H). To evaluate if HH signaling has a protective function, a live/dead assay was performed using the cultured cardiomyocytes following treatment with DMSO and SAG for 48 h. No difference was found in the live/dead assay between control and SAG-treated cardiomyocytes (n=3) (FIG. 2I). Further, the qPCR analysis revealed that the levels of caspase-3 transcripts were unaltered between control and SAG-treated cardiomyocytes (data not shown). These data indicated that activation of HH signaling did not induced anti-apoptotic pathway in the cultured cardiomyocytes. Next, to investigate a pro-proliferative impact of HH signaling, cultured cardiomyocytes were treated with pan-caspase inhibitor in combination with/without SAG and performed EdU-incorporation assay. Pan-caspase-mediated inhibition of apoptosis did not result in any change in the EdU$^+$ cardiomyocytes (FIG. 2J). SAG treatment together with/without pan-caspase inhibition resulted in a comparable increase in the number of EdU$^+$-cardiomyocytes (n=3; p<0.05) (FIG. 2J). These results demonstrated a pro-proliferative impact of HH signaling in the cardiomyocytes. Next, qPCR analysis for Ptc1, Ccnd2, Ccnd1, and Ccne1 transcripts confirmed the induction of cell cycle kinetics upon HH signaling activation (FIG. 2K-L and FIG. 12B-C). Further, fluorescence-activated cell sorting (FACS) analysis of the α-Actinin$^+$-EdU$^+$ population demonstrated increased cardiomyocyte proliferation (2.5-fold) upon SAG treatment (n=3; p<0.05) (FIG. 2M-N). The increased cardiomyocyte proliferation upon SAG treatment was also evident in the serum-free conditions (n=3; p<0.05) (FIG. 12d, e). These results showed that activation of HH signaling promoted the proliferation of postnatal neonatal cardiomyocytes in vitro.

In Vivo Activation of HH Signaling Extends the Cardiac Regenerative Window

Next it was investigated whether activation of HH signals could modulate the cardiomyocyte proliferative potential in vivo. To evaluate the role of HH signaling in vivo, HH signaling was conditionally activated in cardiomyocytes by crossing mouse models with a floxed allele of an active, Smo mutant (SmoM2)[29] with a cardiomyocyte-specific tamoxifen-inducible Cre (αMHC-CreERT2 [αMHC-MerCre-Mer]) (Sohal et al., 2001). Subcutaneous injection of 4-hydroxytamoxifen (TM) in αMHC:CreERT2;Rosa26-ZsGreen neonates at P0/P1 resulted in specific and efficient (>95%) labeling of cardiomyocytes (FIG. 13A-B). Hearts from TM-treated αMHC:CreERT2; SmoM2-YFP$^{fl/+}$ (SmoM2) mice demonstrated increased levels of Pic1, Gli1, and Gli2 transcripts following TM treatment by qPCR, confirming the activation of the HH signaling cascade (FIG. 3A and FIG. 13C-E).

Figure 3A:
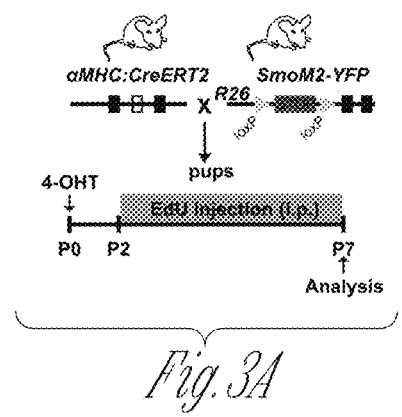
FIGS. 3A-3K. In vivo activation of HH signaling promotes cardiomyocyte proliferation. (A) Schematic for the activation of HH signaling and EdU labeling in the postnatal heart during the regenerative window (P2-P7) in the mouse. (B) Whole mount images of representative control and SmoM2 hearts obtained by crossing αMHC:CreERT2 with Rosa26-SmoM2/YFP mice. Control mice were not injected with 4-hydroxy tamoxifen. (C) Heart weight to body weight (HW/BW) ratio in control and SmoM2 mice (n=5 per group). (D) WGA staining and quantification of the heart sections from control and SmoM2 mice at P7 (n=3). (E,F) Immunostained images (E) and quantification (F) of Nkx2-5$^+$-EdU$^+$ cardiomyocytes in control and SmoM2 hearts. The boxed regions are magnified in E' and E" panels. Arrowheads indicate EdU$^+$-cardiomyocytes. Quantitative analysis in panel F represents the counting of four random fields at 20× magnification from three biological replicates. (G) qPCR analysis of Ccnd2, Ccne1 and Cdkn1b (p27) transcripts using RNA isolated from control and SmoM2 heart tissue (n=3) at P7. (H) Schematic outlining the experimental protocol of cardiomyocyte specific conditional deletion of the Smo-floxed allele (Smo CKO) by crossing αMHC:CreERT2;Smo$^{L/L}$ with Smo$^{L/L}$ mice. (I-K) qPCR analysis of Smo, Ccnd2 and Ccne1 transcripts using RNA isolated from control (white bar) and Smo CKO (black bar) heart tissues (n=3 hearts in each group). Data are presented as mean±SEM (*p<0.05) (see also FIG. 13) and scale bars=100 μm (Panels D,E) and 500 μm (Panel B) as indicated.
Figure 3B:
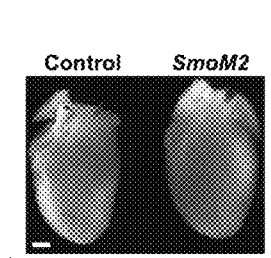
Figure 3C:
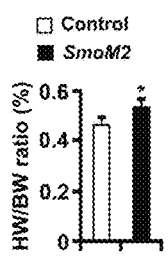
Figure 3D:
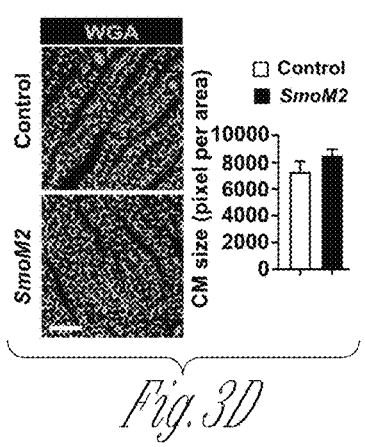
Figure 3E:
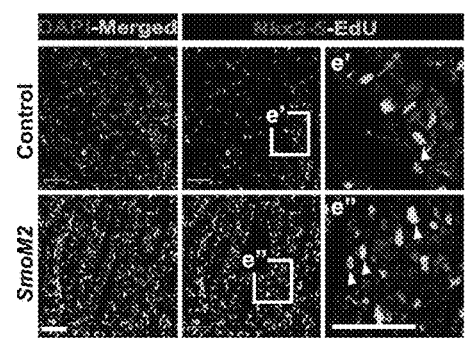
Figure 3F:
Figure 3G:
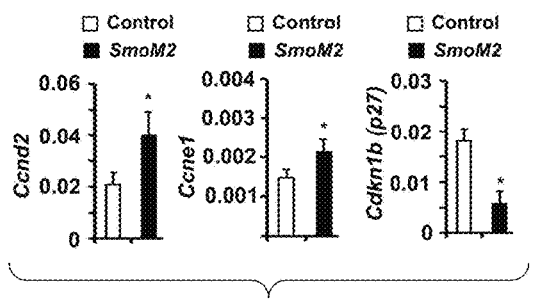
Figure 3H:
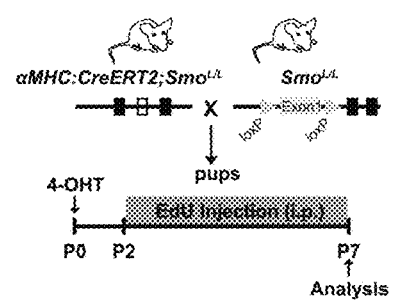
Figure 3I:
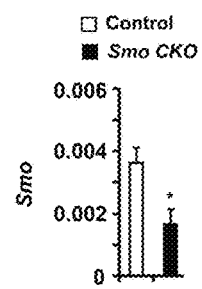
Figure 3J:
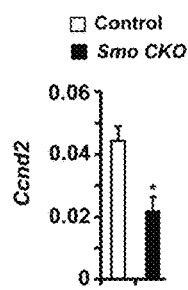
Figure 3K:
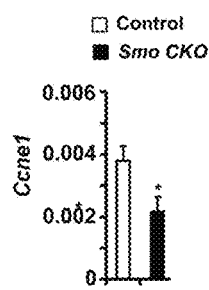

Increased HH signaling in TM-treated αMHC:CreERT2; SmoM2-YFP$^{fl/+}$ (SmoM2) mice revealed cardiac enlargement with increased ventricular wall thickness, heart weight to body weight (HW/BW) ratio (n=5; p<0.05), and heart weight to tibia length (HW/TL) ratio (n=5; p<0.05) (FIG. 3B-C, and FIG. 13F-G). To determine whether cardiac enlargement was due to a hyperplastic or hypertrophic effect, cardiomyocyte proliferation was analyzed between P2-P7 (regenerative period) (Porrello et al., 2012). EdU incorporation assays revealed an increased percentage of EdU$^+$ cells (n=4; p<0.05) and. Nkx2-5$^+$-EdU$^+$ cardiomyocytes (n=4; p<0.05) in the SmoM2 hearts without any detectable change in cardiomyocyte size relative to control hearts (FIG. 3D-F, and FIG. 13H-I). qPCR analysis demonstrated increased levels of Ccnd2 and Ccne1 with reduced expression of Cdkn1b (p27) in SmoM2 hearts (FIG. 3G). These results support the notion that the activation of HH signaling promotes cardiomyocyte proliferation. To further examine this hypothesis, Smo was conditionally deleted in the cardiomyocyte by crossing the αMHC:CreERT2; Smo$^{L/L}$ with Smo-floxed (Smo$^{L/L}$) mice at P0. Deletion of Smo in the cardiomyocyte resulted in reduced levels of Ccnd2 and Ccne1 at P7 (FIG. 3H-K). Overall, these results established that HH signaling regulated the proliferation program of the neonatal cardiomyocyte population in vivo.

Figure 4A:
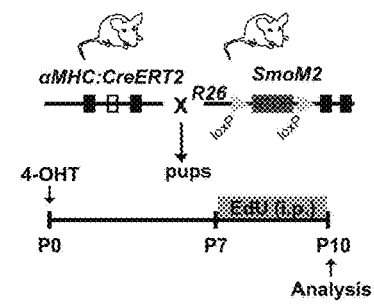
FIGS. 4A-4K. Activation of HH signaling promotes cardiomyocyte proliferation during the non-regenerative period. (A) Schematic for the activation of HH signaling and EdU labeling in the postnatal heart during the non-regenerative window (P7-P10). (B,C) Immunostaining (B) and quantification (C) of Nkx2-5$^+$-EdU$^+$ cardiomyocytes in control and SmoM2 hearts. The boxed region in panel b is magnified in B' and B" panels. Arrowheads indicate EdU$^+$ cardiomyocytes. Quantitative analysis in panel c represents the counting of four random fields at 20× magnification from three biological replicates. (D-F) Immunohistochemical images (D,E) and quantification (F) of α-Actinin$^+$-EdU$^+$ cultured P7 cardiomyocytes from control and SAG treated conditions. Quantitative analysis represents the counting of three random fields from four replicates (n=2,100 cardiomyocytes for each condition). Representative images and quantification of the number of mono-, bi-, multi-nucleated and total myocytes from control and SAG treated samples are shown. (G-J) qPCR analysis of Ptc1, Ccnd2, Ccne1 and Cdkn1b (p27) transcripts using RNA isolated from control and SAG treated P7 cardiomyocytes (n=3). (K) Time-lapse microscopic images of αMHC-mCherry$^+$ cardiomyocytes from control and SAG treated conditions at the specified time intervals. The white arrow indicates the dividing cardiomyocyte. Data are presented as mean±SEM (n=3; *p<0.05) (see also FIG. 14) and scale bars=100 μm.
Figure 4B:
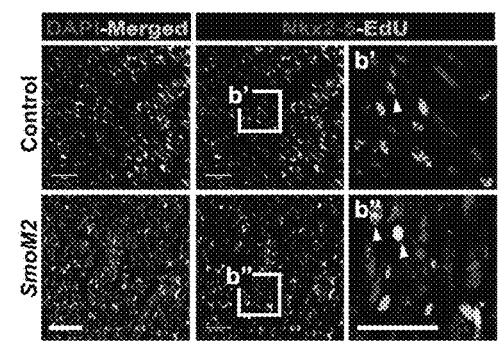
Figure 4C:
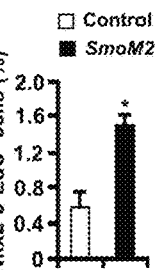
Figure 4D:
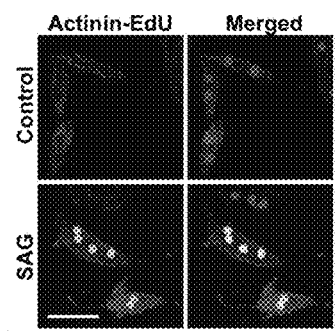
Figure 4E:
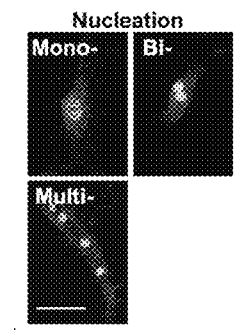
Figure 4F:
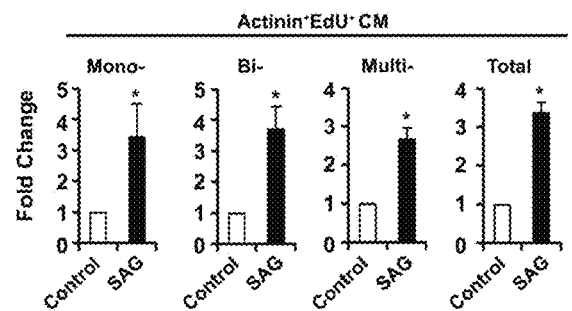
Figure 4G:
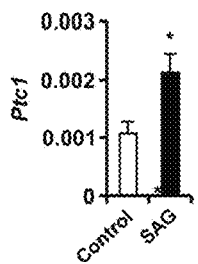
Figure 4H:
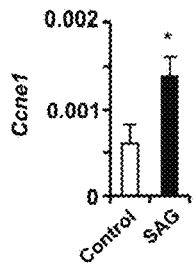
Figure 4I:
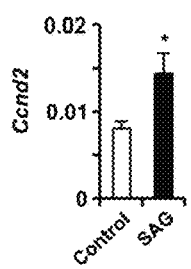
Figure 4J:
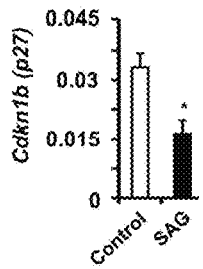
Figure 4K:
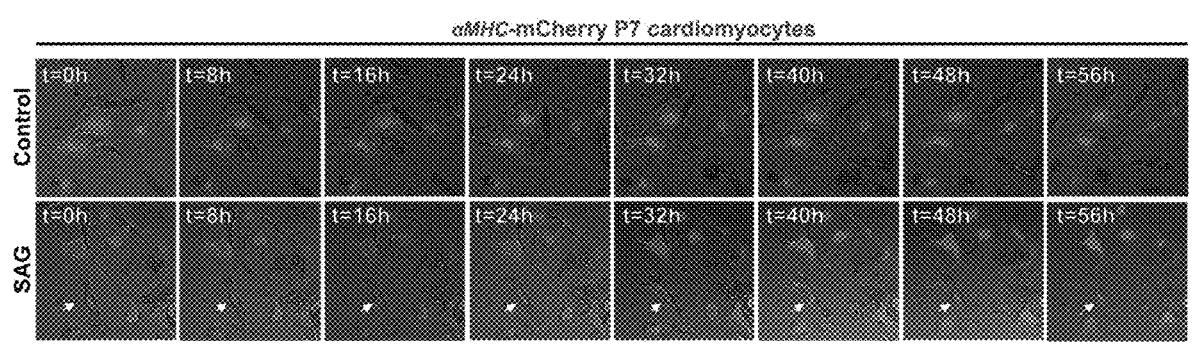

Having established the role of HH signaling in the regenerative period or window (<P7) (Porrello et al., 2012), it was tested whether HH signaling activation was able to promote cardiomyocyte proliferation in the non-proliferative/non-regenerative window (>P7). SmoM2 pups were pulsed with EdU between P7-P10 (FIG. 4A). As expected, few proliferating cardiomyocytes were noted at P10 in the wild-type control. In contrast, activation of Smo (SmoM2) resulted in an increased percentage of Nkx2-5$^+$-EdU$^+$ cells (~2-fold) relative to control (n=3; p<0.05) (FIG. 4B-C). To confirm these in vivo findings, P7 cardiomyocytes (>95% rod-shaped binucleated cardiomyocytes) were isolated, treated with SAG and cardiomyocyte proliferation examined. Remarkably, SAG treatment resulted in an increased number of α-Actinin$^+$-EdU$^+$ cardiomyocytes with a significant increase (~3-fold) in the number of mono-, bi-, and multi-nucleated cardiomyocytes (n=4; p<0.05) (FIG. 4D-F). SAG treatment of P7-isolated cardiomyocytes resulted in increased expression of Ptc1, Ccne1, and Ccnd2, and reduced expression of Cdkn1b (p27) as detected by qPCR (FIG. 4G-J). To further monitor the HH signaling mediated activation of cardiomyocyte cell division, time-lapse microscopic experiments were undertaken using αMHC-mCherry$^+$ cardiomyocytes isolated from P7 mice following treatment with either DMSO or SAG. P7 cardiomyocytes have relatively low proliferative ability as compared to P1-P2 cardiomyocytes. Similar to immunostaining results, a dividing P7 cardiomyocyte was not found in the control condition (FIG. 4K). Interestingly, multiple dividing αMHC-mCherry$^+$ P7 cardiomyocytes were observed in the SAG treatment condition (FIG. 4K). Overall, these findings clearly demonstrated a proliferative role of HH signaling in the post-natal cardiomyocytes. Next, the ability of HH signaling to activate proliferation during the late juvenile stage (P28) was investigated (FIG. 14A). A significant increase was observed in heart size (n=4; p<0.05) (FIG. 14B-D), in the number of EdU$^+$ cells (2-fold), and in the number of Nkx2-5$^+$-EdU$^+$ cardiomyocytes (1.8-fold) (n=3; p<0.05) in TM-treated SmoM2 mice (FIG. 14E-F). Collectively, these results demonstrated that HH signaling activation was sufficient to extend cardiomyocyte proliferation during the non-proliferative/non-regenerative window.

HH Signaling Regulates Mammalian Heart Regeneration Following Injury

Figure 5A:
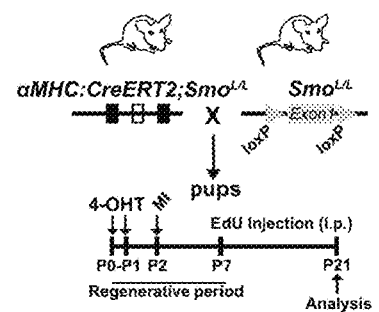
FIGS. 5A-5F. Conditional deletion of Smoothened (Smo CKO) results in impaired neonatal heart regeneration following myocardial injury. (A) Schematic of cardiomyocyte specific conditional deletion of the floxed-Smo allele and heart regeneration analysis following MI. The MI was performed on P2. (B,C) Masson trichrome staining of representative sections (B) and fibrotic area quantification (C) of heart sections at 21 days post injury (n=5 for each group). (D) Echocardiographic measurements (SF) of cardiac function from control and Smo CKO at 21 day post-MI (n=5 per group). (E,F) Immunostaining (E) and quantification (F) of Nkx2-5$^+$-EdU$^+$ cardiomyocytes from control and Smo CKO at 21 day post-MI (n=4 per group). The boxed region in the middle panel of "E" is magnified in panels E' and E". Arrowheads indicate EdU$^+$ cardiomyocytes. Quantitative analysis represents counting of three random fields at 20× magnification from four biological replicates in each group. Data are presented as mean±SEM (*p<0.05, **p<0.01) and scale bars=100 μm.
Figure 5B:
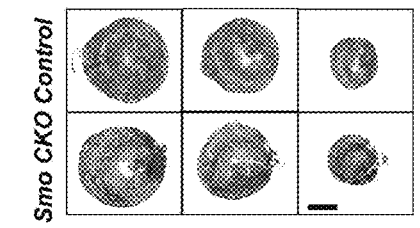
Figure 5C:
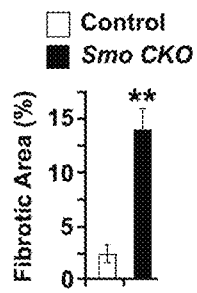
Figure 5D:
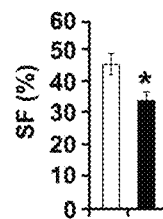
Figure 5E:
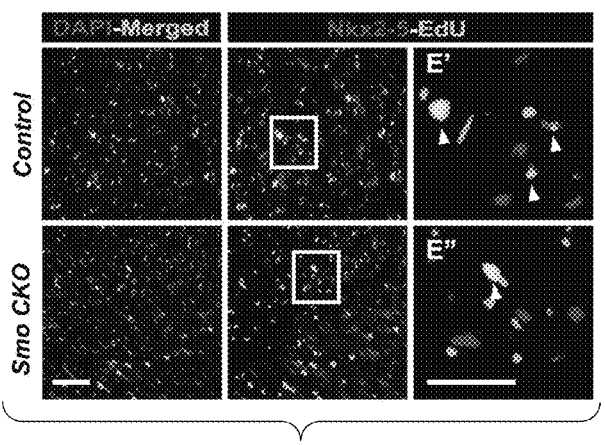
Figure 5F:
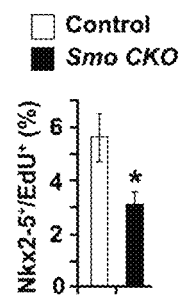

Having established that HH signals could modulate cardiomyocyte proliferation both in vitro and in vivo, the role of HH signaling during heart regeneration following injury was directly evaluated. To determine whether HH signaling is required for heart regeneration during the regenerative window (<P7), it was tested whether conditional deletion of floxed-Smo (Smo$^{L/L}$) resulted in impaired neonatal heart regeneration. 4-hydroxytamoxifen (TM) was injected in the αMHC:CreERT2;Smo$^{L/L}$ (Smo CKO) neonatal pups at P0 and P1, and performed myocardial infarction (MI) injury by ligating the left anterior descending (LAD) coronary artery at P2 (regenerative period) (FIG. 5A). Previous studies have shown a robust regenerative potential in the P2 heart following injury (Porrello et al., 2011). Regeneration in TM-treated Smo CKO and control mice was analyzed at P21 following MI (FIG. 5A). While the control hearts regenerated normally, Smo CKO hearts showed impaired regeneration and scar tissue formation at 21 days post-MI (n=5; p<0.01) (FIG. 5B-C). To further validate these results, a functional analysis of the control and Smo CKO regenerating hearts was undertaken. Echocardiographic data analysis revealed decreased cardiac function at 21 days post-MI (n=5; p<0.05) (FIG. 5D). Next, we performed an EdU-labeling assay using the regenerating tissues from control and Smo CKO hearts. Smo CKO mice showed a reduced percentage of Nkx2-5$^+$-EdU$^+$ cardiomyocytes relative to controls (n=4; p<0.05) using immunohistochemical analysis (FIG. 5E-F). These results indicated that HH signaling is required for cardiomyocyte proliferation and heart regeneration in vivo.

Based on these results, it was next hypothesized that HH signaling activation may promote the regenerative response in vivo during the non-regenerative period (>P7). The effect of HH signaling activation following myocardial infarction (MI) injury was examined by ligating the left anterior descending (LAD) coronary artery at P7 (FIG. 6A). Activating HH signaling in TM-treated SmoM2 mice led to a significant improvement in cardiac function following MI compared to controls at 21 dpi and 42 dpi (n=4; p<0.05) (FIG. 6B). Extensive scarring and loss of myocardial tissue was observed in the control hearts. In contrast, TM-treated SmoM2 hearts revealed cardiac regeneration with a significantly reduced fibrotic area (n=4; p<0.05) (FIG. 6C-D). Immunohistochemical analysis of the regenerating tissue was performed to visualize the cellular proliferation upon HH activation. SmoM2-expressing hearts revealed increased Desmin$^+$-EdU$^+$ cardiomyocytes (2.1-fold; n=3; p<0.05) with a higher percentage of Desmin$^+$-PCNA$^+$ cardiomyocytes (4-fold; n=3; p<0.05) and Desmin$^+$-pH3$^+$ (2-fold; n=3; p<0.05) cardiomyocytes compared to controls (FIG. 6E-F, and FIG. 15A-D). Furthermore, a significantly higher percentage of Mef2a$^+$-PCNA$^+$ cardiomyocytes (>2-fold; n=3; p<0.05) was conserved in the injured, border, and remote areas of the SmoM2-expressing hearts relative to controls (FIG. 6G-H). Next, lineage-tracing experiments were performed to monitor the contribution of pre-existing cardiomyocytes to the regenerating tissue (FIG. 6I). These experiments demonstrated that SmoM2-expressing hearts induced the proliferative response in pre-existing cardiomyocytes, and that largely (>80%) contributed to the regenerating heart (FIG. 6J-K). These results indicated that HH signaling was able to extend the temporal window for heart regeneration in vivo.

Figure 7A:
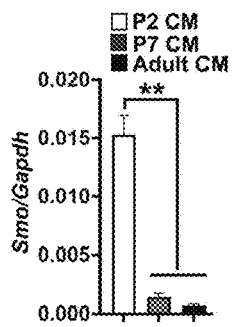
FIGS. 7A-7S. Constitutively active Smoothened mutant (SmoM2) promotes adult heart regeneration. (A) qPCR analysis of Smoothened (Smo) transcripts using RNA obtained from isolated cardiomyocytes at P2, P7 and P60 mouse hearts (n=3). (B) qPCR analysis of Smoothened (Smo) transcripts using RNA obtained from isolated cardiomyocytes from adult uninjured and injured heart tissue at 7 dpi (n=3). (C,D) Immunohistochemical images (C) and quantification (D) of α-Actin$^+$-EdU$^+$ isolated adult cardiomyocytes following exposure to control (white bar) and SAG (black bar) and pulsed with EdU. Quantitative analysis represents the counting of four different fields at 10× from three replicates (n=1500 cardiomyocytes for each condition). (E) qPCR analysis of Shh transcripts using RNA obtained from adult uninjured and injured heart tissue at 7 dpi (n=3). (F) qPCR analysis of Shh transcripts using RNA obtained from adult injured heart tissue, FACS-sorted CD31$^+$- and CD90$^+$-cells at 7 days post-MI (n=3). (G) Schematic outlining the experimental design for Smo activation (SmoM2) and cardiac regeneration analysis following myocardial injury. (H) Whole mount images of representative control and SmoM2 hearts following MI. Control mice were injected with corn oil. (I) Heart weight to body weight (HW/BW) ratio in control and SmoM2 adult mice at 42 dpi (n=3 per group). (J,K) Masson trichrome staining (J) and fibrotic area quantification (K) of representative heart sections at 42 days post injury from control and SmoM2 hearts. (L) Time series echocardiographic measurement of ejection fraction (EF %) of control and SmoM2 mice following MI (n=3 per group). (M,N) Immunostaining (M) and quantification (N) of α-Actinin$^+$-Ki67$^+$ cardiomyocytes in control and SmoM2 hearts. Arrowheads indicate Ki67$^+$ labeled cardiomyocytes and arrows indicate Ki67$^+$ labeled non-cardiomyocytes. Quantitative analysis represents counting three different fields at 20× magnification. The boxed region is magnified and shown in the right panel. (O) Schematic outlining the EdU-pulse experiment and cardiac regeneration analysis following myocardial injury. (P,Q) Immunostaining (P) and quantification (Q) of Actinin$^+$-EdU$^+$ cardiomyocytes in control and SmoM2 hearts. Arrowheads indicate EdU-labeled cardiomyocytes. Quantitative analysis represents counting three different fields at 20× magnification near the injured area. The boxed region is magnified and shown in the right panel. (R) Immunostaining of control and SmoM2-expressing heart tissue sections using endomucin antibodies at 42 dpi. The boxed region is magnified and shown in the right panel. (S) Immunostaining of control and SmoM2-expressing heart tissue sections using α-Actinin and active caspase-3 antibodies at 42 dpi. The white arrows indicate α-Actinin$^+$-caspase-3$^+$ cardiomyocytes. The boxed region is magnified and shown in the right panel. Data are presented as mean±SEM (*p<0.05) and scale bars=100 μm.
Figure 7B:
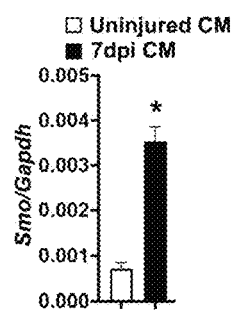
Figure 7C:
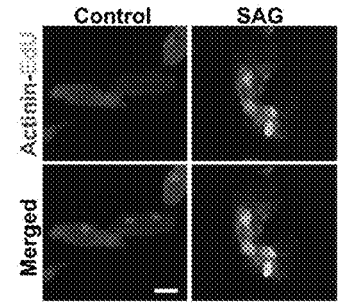
Figure 7D:
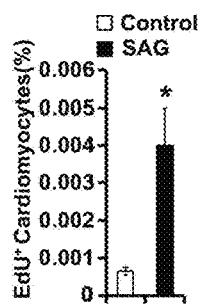
Figure 7E:
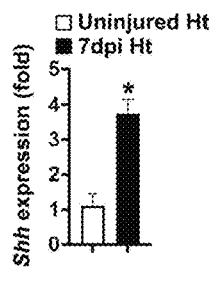
Figure 7F:
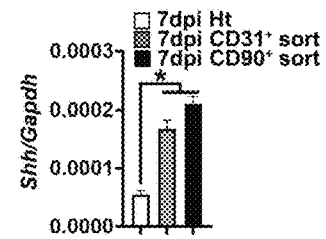
Figure 7G:
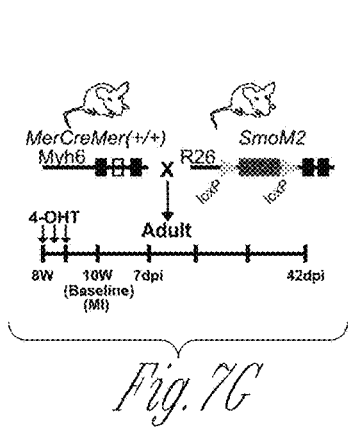
Figure 7H:
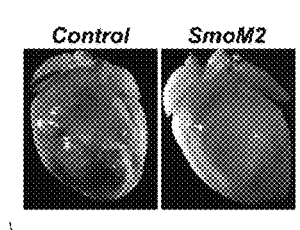
Figure 7I:
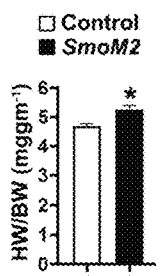
Figure 7J:
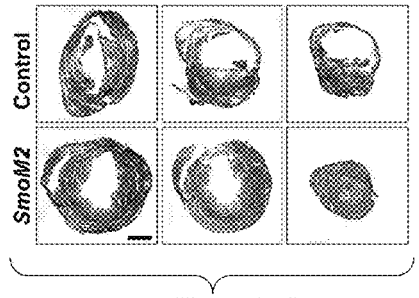
Figure 7K:
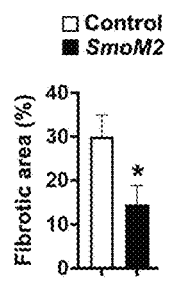
Figure 7L:
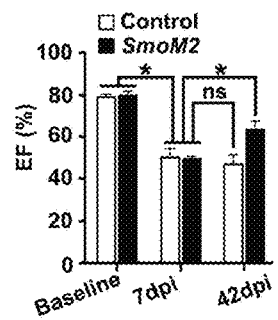
Figure 7M:
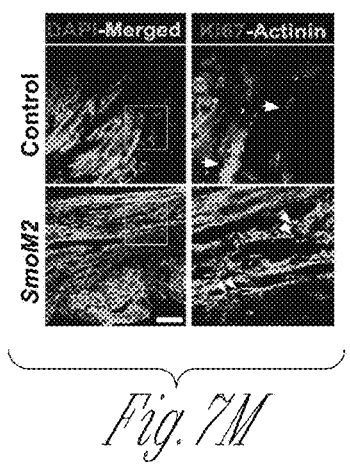
Figure 7N:
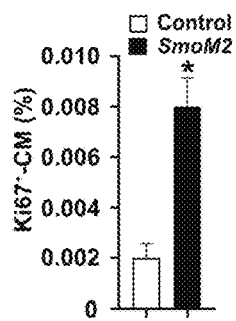
Figure 7O:
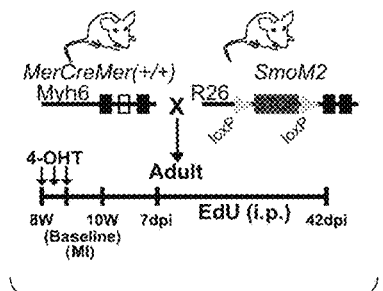
Figure 7P:
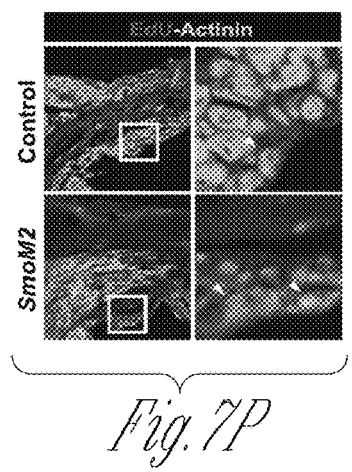
Figure 7Q:
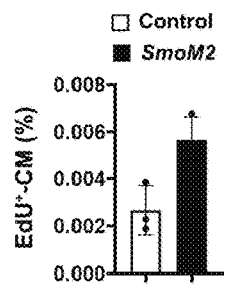

To determine the role of Smo during the regulation of adult mouse heart regeneration, expression analysis of Smoothened (Smo) transcript was performed using RNA obtained from the isolated cardiomyocytes at P2, P7 and P60 stages. Robust expression of Smo was observed in the P2 FACS-sorted αMHC-mCherry$^+$ cardiomyocytes (FIG. 7A). The levels of Smo transcripts were decreased at the subsequent stages with least expression in the P60 isolated cardiomyocytes (FIG. 7A). To visualize the expression of Smo transcripts upon injury, adult LAD ligation injury was performed and the expression of Smo evaluated using the isolated cardiomyocytes at 7 dpi following injury. qPCR analysis at 7 dpi revealed increased expression of Smo in the injured cardiomyocytes relative to uninjured cardiomyocytes (FIG. 7B). To monitor whether activated Smoothened could modulate regeneration capacity of the adult mouse heart, adult mouse cardiomyocytes were isolated, treated with SAG, and then analyzed using EdU-incorporation assays. No or minimal α-Actinin$^+$-EdU$^+$ cardiomyocytes were observed in the control or untreated adult cardiomyocytes. Notably, SAG-mediated activation of HH signaling led to an increased number of α-Actinin$^+$-EdU$^+$ cardiomyocytes (n=3; p<0.05) (FIG. 7C-D). These results demonstrated that HH signaling activation was sufficient to induce proliferation in the mature cardiomyocytes. Next the role of HH signaling during adult heart regeneration was evaluated following injury. Initially, the expression of Shh transcripts were investigated using the injured heart tissue. qPCR analysis revealed 4-fold increase in the levels of Shh transcripts in the injured heart tissue relative to uninjured tissue (FIG. 7E). Next, to evaluate the source of Shh transcripts, CD31$^+$ cells (endothelial lineage) and CD90$^+$ cells (fibroblast population) were sorted from the injured heart tissue and qPCR experiments perfumed at 7 dpi. The analysis revealed robust expression of Shh in both CD31$^+$ and CD90$^+$ lineages, indicating that these cells could be the major source of Shh morphogen (FIG. 7F). To interrogate the functions of HH signaling during adult heart regeneration following injury, adult αMHC:CreERT2;SmoM2-YFP$^{fl/+}$ (SmoM2) mice were utilized, and HH signaling was activated in cardiomyocytes by subcutaneous injection of 4-hydroxytamoxifen (TM) at P56 (8 weeks (8 W) old). Following corn oil/TM-injection, the animals were allowed to recover for one week and MI-injury was performed at 10 W of age (FIG. 7G). Whole-mount image analysis revealed enlarged heart with increased heart weight to body weight ratio in the TM-treated SmoM2 mice following injury at 42 dpi (FIG. 7H-I). Subsequent analysis of the whole-mount images demonstrated presence of scar tissue in the control animals, whereas TM-treated SmoM2 mice showed relatively less scarring (FIG. 7H). Further, histological examination showed extensive scarring and loss of myocardial tissue in the control hearts, correlating with the lack of regeneration in the adult tissue (FIG. 7J). Remarkably, TM-treated SmoM2 hearts revealed significantly reduced fibrotic area following ischemic injury (n=3; p<0.05) (FIG. 7J-K). Activation of HH signaling in TM-treated SmoM2 mice led to a significant improvement in ejection fraction (EF) as compared to controls at 42 dpi (n=3; p<0.05) (FIG. 7L). To determine whether the decreased fibrosis in the TM-treated SmoM2 hearts was due to increased cardiomyocyte proliferation, immunohistochemical analysis WAS UNDERTAKEN using Ki67-antibodies. An increased number of Ki67$^+$-Actinin$^+$ cells was observed in the SmoM2 hearts as compared to control tissue (n=3; p<0.05) (FIG. 7M-N). Next, to further validate these results, the LAD-ligated animals were pulsed with EdU (i.p.) every 3 day post-MI and performed EdU-incorporation assay at 42 dpi following injury (FIG. 7O). TM-treated SmoM2-expressing hearts revealed increased Actinin$^+$-EdU$^+$ cardiomyocytes (1.8-fold; n=3; p<0.05) as compared to controls (FIG. 7P-Q). These experiments demonstrated that SmoM2-expressing hearts induced the proliferative response following injury in the adult animals. Multiple reports have described a global anti-apoptotic as well as neovascularization impact of Shh on cardiac tissue following MI, however, these studies were performed in a non-specific manner (Kusano et al., 2005).

Figure 7R:
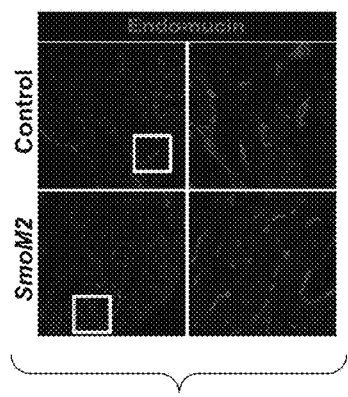
Figure 7S:
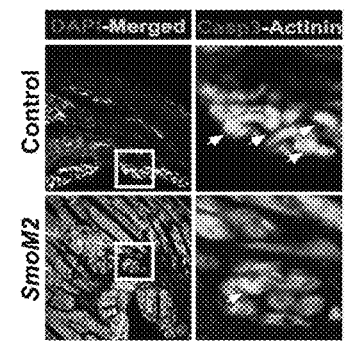

To analyze whether cardiomyocyte-specific expression of SmoM2 hearts have increased neovascularization following MI, endomucin staining was performed at 42 days post-MI. The fluorescence microscopic analysis showed a mild increase in the vascular structures in the SmoM2-expressing hearts as compared to control hearts (FIG. 7R). Next active caspase-3 immunostaining was performed and low numbers of α-Actinin$^+$-caspase-3$^+$ cardiomyocytes (n=3) were found in the SmoM2-expressing hearts as compared to control hearts (FIG. 7S). These results provide compelling evidence for the essential role of HH signaling during heart regeneration in the adult animals.

Conserved Role of HH Signaling in the Regulation of Cardiomyocyte Proliferation

Having described the role of HH signaling in the regulation of cardiomyocyte proliferation and regeneration in both newt and mouse (FIG. 1-7), the conserved function of HH signaling was investigated using human-induced pluripotent stem cell (hiPSC)-derived cardiomyocytes (hiPSC-CMs). hiPSCs were differentiated using a protocol that yields functional cardiomyocytes (Lian et al., 2013). Using this protocol, robustly beating cardiomyocytes were obtained with high efficiency (>78% cTnT+ cardiomyocytes) at day 60 (FIG. 16A-B). The effect of increased HH signaling on the proliferation of terminally differentiated hiPSC-CMs was examined (FIG. 16C-F). Administration of SAG to day-60 hiPSC-CMs resulted in increased α-Actinin$^+$-EdU$^+$ cardiomyocytes (2-fold; n=3; p<0.01) and α-Actinin$^+$-Ki67$^+$ cardiomyocytes (~3-fold; n=3; p<0.01), respectively (FIG. 16C-F). In contrast, CyA-treatment resulted in a significant decrease (n=3; p<0.05) in the proliferation of day 60 hiPSC-CMs (FIG. 16C-F). These findings support an evolutionary conserved role for HH signaling in the regulation of cardiomyocyte proliferation.

Gli1-Mycn Cascade Regulates the Cardiomyocyte Proliferative Response

Figure 8A:
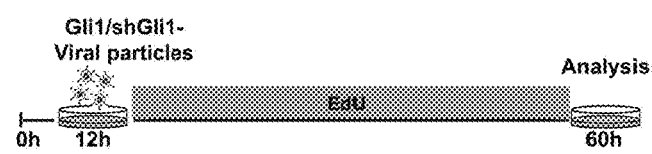
FIGS. 8A-8S. HH-Gli1-Mycn network regulates cardiomyocyte proliferation. (A) Schematic of Gli1 over-expression and knockdown experiments in the neonatal cardiomyocytes. (B,C) Immunostaining (B) and quantification of α-Actinin$^+$-EdU$^+$ cells (C) from control, Gli1 and shGli1 lentiviral infected cardiomyocytes. Quantitative analysis represents counting from four randomly selected fields at 10× magnification from three biological replicates. (D-F) qPGR analysis of Ccnd2, Ccne1 and Cdkn1b (p27) following lentiviral Gli1 overexpression or knockdown (shGli1) in the P1 cardiomyocytes. (G) qPCR analysis of Mycn transcripts using RNA isolated from P1 and P28 wild-type heart tissue (n=3). (H) qPCR analysis of Mycn transcripts using RNA isolated from control, SAG and CyA treated isolated neonatal cardiomyocytes (n=3 replicates from each group). (I) Schematic of Mycn over-expression and knockdown experiments in the P1 cardiomyocytes. (J,K) Immunostaining (J) and quantification of α-Actinin$^+$-EdU$^+$ cells K) from control, Mycn and shMycn lentiviral infected neonatal cardiomyocytes. Quantification was performed from three biological replicates. (L,M) qPCR analysis of Ccnd2 and Cdk1b (p27) in the cultured cardiomyocytes following Mycn overexpression and knockdown (shMycn) conditions (n=3 for each group). (N) Schematic showing the Mycn genomic locus (top panel) harboring evolutionary conserved Gli1 binding motifs. (O) ChIP-PCR and quantification (P) for the Mycn promoter region following immunoprecipitation for endogenous Gli1 using isolated neonatal cardiomyocytes. (Q) Schematic of combinatorial lentiviral infection studies using Gil1, shGli1, Mycn and shMycn viral particles. (R,S) Immunostaining (R) and quantification of α-Actinin$^+$-EdU$^+$ cells (S) from control, Gli1, shGli1, Mycn and shMycn (using Clone A; see FIG. 16J) infected using isolated neonatal cardiomyocytes. Quantitative analysis represents counting of three random fields from three replicates (n=1000 cardiomyocytes for each condition). Arrowheads indicate EdU$^+$ labeled cardiomyocytes Data are presented as mean±SEM (*p<0.05; **p<0.01; $^\#$represents significance (p<0.05) between Gli1+shMycn compared Gli1 conditions; $^\delta$represents significance (p<0.05) between shGli1+Mycn compared to Mycn conditions) (see also FIG. 16) and scale bars=200 µm.
Figure 8C:
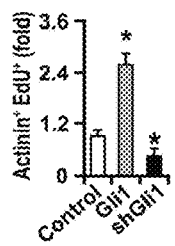
Figure 8B:
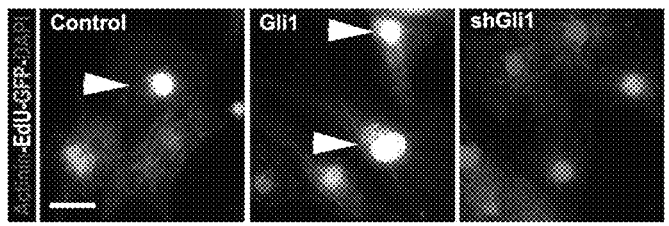
Figure 8D:
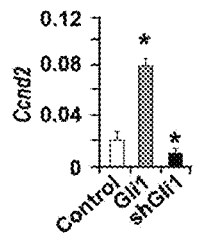
Figure 8E:
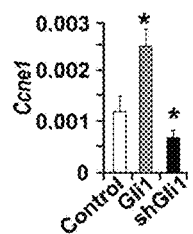
Figure 8F:
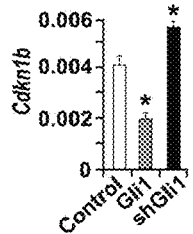
Figure 17A:
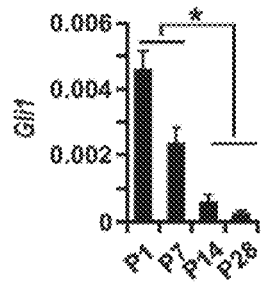
FIGS. 17A-17J. Gli1-Mycn network regulates neonatal cardiomyocyte proliferation. (A,B) qPCR analysis of Gli1 and Gli3 transcripts using RNA isolated from P1-P28 wild type heart tissue (n=3 at each time period). (C,D) qPCR analysis of Gli1 and Gli3 transcripts using RNA isolated from control, SAG and CyA-treated P1 cultured cardiomyocytes (n=3 for each group). (E,F) qPCR analysis of Gli1 transcripts following lentiviral Gli1 overexpression or following Gli1 knockdown using three different shRNA clones. (G,H) qPCR analysis of Mycn transcripts following Gli1 overexpression and Gli1 knockdown (using shRNA clone B) in P1 cultured cardiomyocytes. (I,J) qPCR analysis of Mycn transcripts following lentiviral Mycn overexpression or following Mycn knockdown using three different shRNA clones. Data in panels A-J represent mean±SEM (*p<0.05; **p<0.01).
Figure 17B:
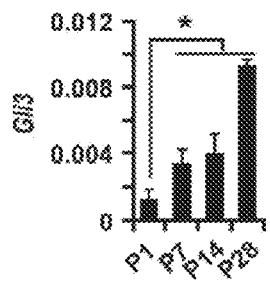
Figure 17C:
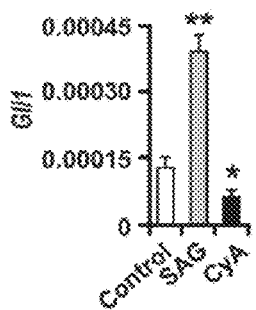
Figure 17D:
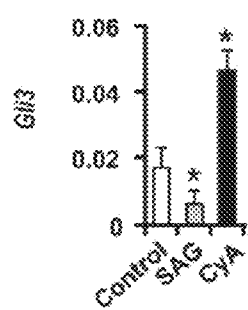
Figure 17E:
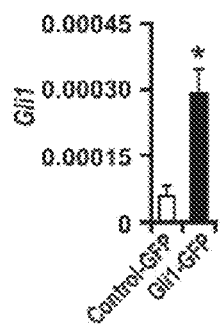
Figure 17F:
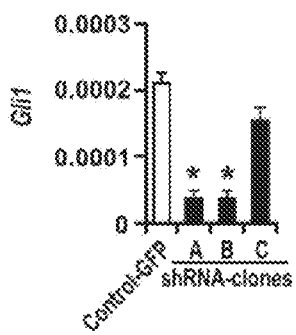

To decipher the mechanism by which HH signaling mediates cardiomyocyte proliferation, the expression of the downstream effectors Gli1 and Gli 3 from the P1-P28 mouse heart was determined. Robust Gli1 expression was observed at P1, which was essentially extinguished by P28; conversely, Gli3 expression was low at P1 and increased significantly by P28 (FIG. 17A-B). Activation of HH signaling by SAG-treatment induced Gli1 and reduced Gli3 expression. Conversely, CyA-treatment caused reduced Gli1 and increased Gli3 expression in isolated mouse neonatal cardiomyocytes (FIG. 17C-D). To further explore Gli1-dependent regulation of cardiomyocyte proliferation, lentiviral-mediated overexpression and knockdown of Gli1 in neonatal cardiomyocytes was performed (FIG. 8A and FIG. 17E-F). Overexpression of Gli1 by lentiviral particles resulted in increased α-Actinin$^+$-EdU$^+$ cardiomyocytes (2-fold; n=3; p<0.05) with higher levels of Ccnd2 and Ccne1 transcripts (FIG. 8B-E). In contrast, Gli1-knockdown (shGli1) led to impaired cardiomyocyte proliferation (n=3; p<0.05) and reduced expression of cyclins with a concomitant increase in Cdkn1b (p27) levels (FIG. 8B-F).

Figure 8G:
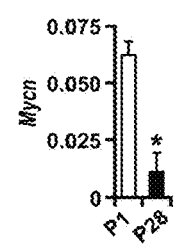
Figure 8H:
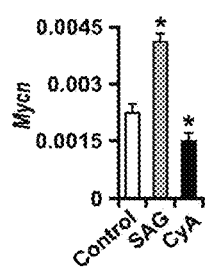
Figure 8I:
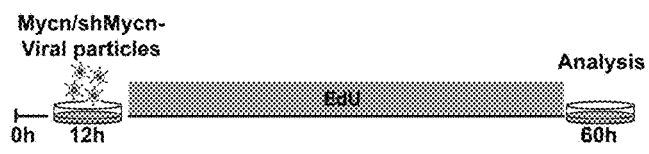
Figure 17G:
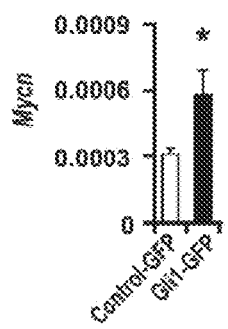
Figure 17H:
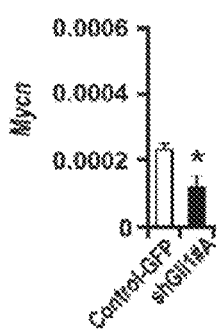

Next, to identify downstream targets of Gli1, Gli1-ChIPseq data sets (Peterson et al., 2012) were used and putative candidates based on their expression in the cardiomyocyte, ChIPseq binding proximity and proliferative function were examined. Using these criteria, the candidates were prioritized and Mycn identified as the top-ranked candidate (FIG. 19). Notably, Mycn transcripts paralleled Gli1 expression with increased expression in the P1 heart and extinguished expression by P28 (FIG. 8G). The Mycn transcripts were increased following SAG-treatment, whereas CyA-treatment resulted in reduced expression in isolated mouse neonatal cardiomyocytes (FIG. 8H). Lentiviral-mediated Gli1 overexpression or knockdown in isolated neonatal cardiomyocytes led to an increase or decrease in Mycn transcripts, respectively (FIG. 17G-H), suggesting that the function of Gli1 was mediated through Mycn.

Figure 8J:
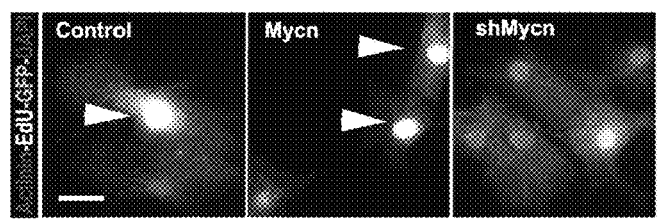
Figure 8K:
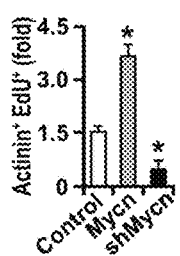
Figure 8L:
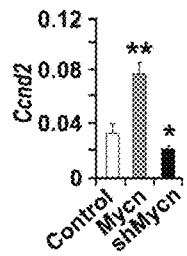
Figure 8M:
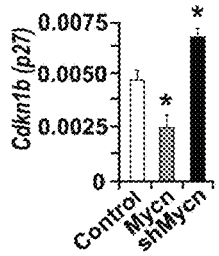
Figure 8N:
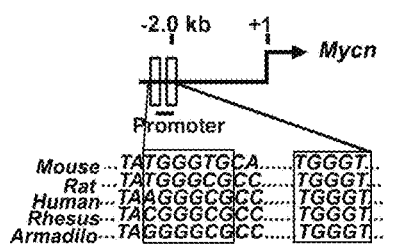
Figure 8O:
Figure 8P:
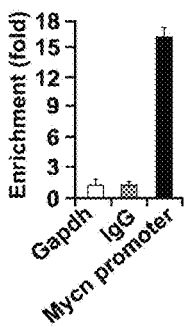
Figure 8Q:
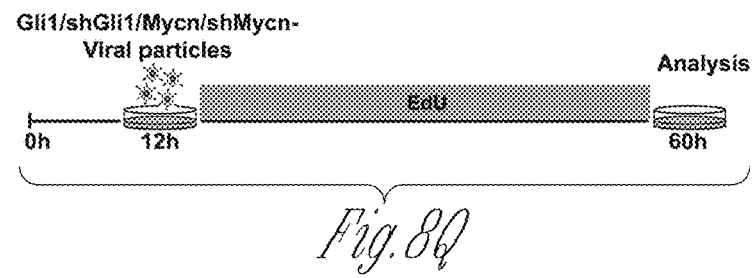
Figure 8R:
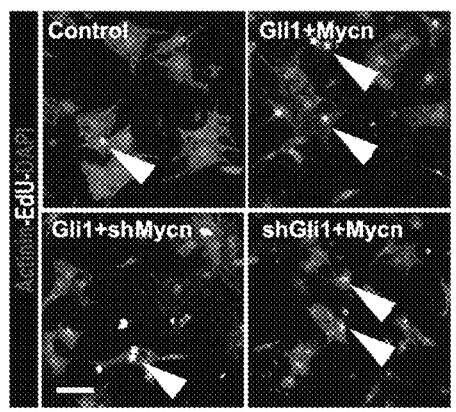
Figure 8S:
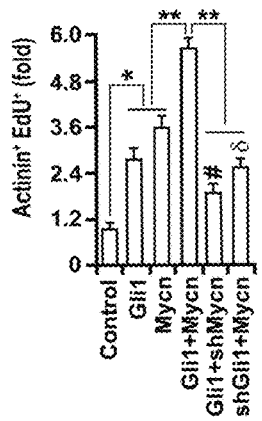
Figure 17I:
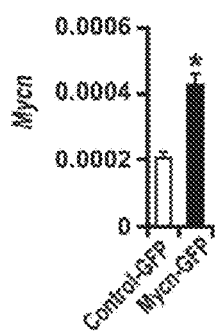
Figure 17J:
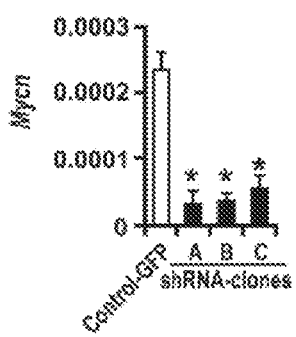
Figure 18A:
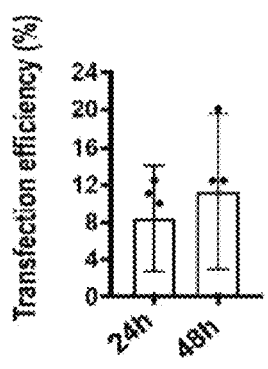
FIGS. 18A-B. mRNA mediated transfection of Gfp and Mycn in adult cardiomyocyte proliferation. (A,B) Quantification (A) and microscopic images (B) of the Gfp transfected adult cardiomyocytes at 24 h and 48 h post-transfection.
Figure 18B:
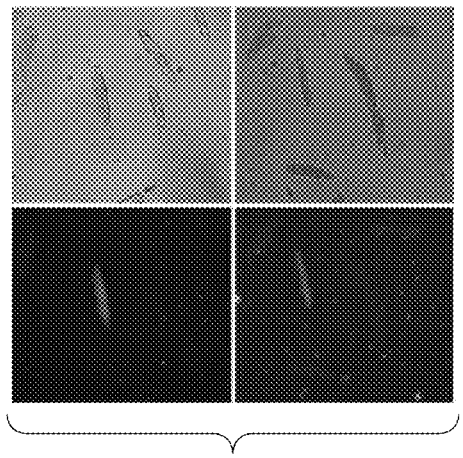

The direct effect of Mycn on neonatal cardiomyocyte proliferation was examined using lentiviral-mediated over-expression and knockdown of Mycn (FIG. 8J and FIG. 17I-J). Induction of Mycn led to a significant increase in the number of α-Actinin$^+$-EdU$^+$ cardiomyocytes (3.5-fold; n=3; p<0.05) with increased Ccnd2 transcript expression (FIG. 8J-L). Conversely, the knockdown of Mycn resulted in a decreased proliferative response and increased Cdkn1b (p27) levels in the cardiomyocytes (FIG. 8J-M). To examine Gli1-Mycn interaction in vivo, chromatin immunoprecipitation (ChIP)-PCR for endogenous Gli1 proteins was performed using isolated neonatal cardiomyocytes and demonstrated Gli1 binding to the Mycn promoter (FIG. 8N-P). To further define the Gli1-Mycn regulatory pathway, combinatorial lentiviral infection studies were performed using Gil1, shGli1, Mycn, and shMycn viral particles in isolated neonatal murine cardiomyocytes (FIG. 8Q). Co-expression of Gli1 and Mycn resulted in a robust increase (5-fold; n=3; p<0.01) in the EdU$^+$-cardiomyocytes, suggesting an additive role of these two factors (FIG. 8R-S). Induction of Mycn together with Gli1-knockdown or vice-versa resulted in impaired proliferative index in isolated cardiomyocytes as compared to Gli1 or Mycn by itself (FIG. 8R-S). Next, to determine the proliferative role of Mycn in the adult mouse myocardium, expression analysis of Mycn transcript were performed using the isolated cardiomyocytes from three postnatal stages including P2, P7 and P60. The qPCR analysis revealed a robust expression of Mycn in the P2, FACS-sorted αMHC-mCherry$^+$ cardiomyocytes (p<0.01) (FIG. 9A). Low levels of Mycn transcripts were detected at the subsequent stages with least expression in the P60 isolated cardiomyocytes (FIG. 9A). Next the expression of Mycn transcripts following adult LAD ligation injury was tested at 7 dpi. qPCR analysis at 7 dpi showed a non-significant change in the levels of Mycn in the injured hearts as compared to uninjured tissue (n=3) (FIG. 9B). To evaluate whether the levels of Mycn transcripts were altered upon activation of HH signaling, LAD ligation injury was conducted in the control and TM-treated SmoM2-expressing hearts and its expression analyzed at 7 dpi. qPCR analysis revealed a significant increase in the Mycn transcripts in the SmoM2-expressing hearts as compared to control injured hearts (n=3; p<0.05) (FIG. 9C). These results further supported the notion that HH signaling is upstream of the Mycn regulatory network in the in vivo settings as well. Next, to monitor whether over-expression of Mycn could recapitulate the impact of HH signaling stimulation in the adult cardiomyocyte proliferation (FIG. 7C-D), Gfp and Mycn mRNA transfection experiments were undertaken using the isolated adult cardiomyocytes and performed proliferative assay. Based on the GFP expression, ~8-12% of transfection efficiency was observed at 24 h. The number of transfected GFP$^+$ cells did not change till 48 h (FIG. 18A-B). Cardiomyocyte proliferation was examined using the mitosis marker pH3 (phosphorylated histone H3) and α-Actinin antibodies in these settings. No pH3$^+$-Actinin$^+$ cells were found in the Gfp transfected conditions, indicating low or no proliferative ability of the adult mature cardiomyocytes (n=3) (FIG. 9D-E). mRNA-mediated over-expression of Mycn resulted in induction of cardiomyocyte proliferation as measured by the increased percentage of pH3$^+$-Actinin$^+$ cells relative to the Gfp transfected cells (n=3; p<0.05) (FIG. 9D-E). Remarkably, Mycn transfections led to a significant increase (~1.9-fold) in the number of mono-nucleated cardiomyocytes, with non-significant changes in the bi- and multi-nucleated myocytes (n=3; p<0.05) (FIG. 9f-h). These results clearly support the notion that Mycn is one of the downstream effectors of Gli1 in cardiomyocyte proliferation and regeneration both in vitro as well as in vivo (FIG. 9K).

Discussion

Evolutionary conserved mechanisms that govern development and cellular proliferation have been described. These studies have uncovered mechanisms in lower organisms such as the fly, zebrafish, frogs, and newt, and have been used to interrogate and modulate pathways in mammalian organs. These strategies have led to discoveries including Hippo signaling, Wnt signaling, Notch signaling, and other pathways that regulate tissue regeneration in lower organisms, and have been shown to harbor a similar role in mammalian organisms (Xin et al., 2013; Xin et al., 2011). Several signaling factors, transcription factors, and microRNAs have been shown to regulate cardiogenesis, however, their roles in the postnatal heart following injury are unclear. In the present study, the power of the regenerating newt heart, genomics, and pharmacological perturbations, as well as genetic perturbations, were used to show the impact of HH signaling on cardiomyocyte proliferation from newt to mouse to human. At least three findings resulted from the experiments.

First, the role of hedgehog signaling as a promoter of cardiomyocyte proliferation was defined. The present studies clearly demonstrated a pro-proliferative effect of HH signaling without impacting the apoptotic pathway. The hedgehog signaling pathway has been shown to have essential roles during embryogenesis (Jeong et al., 2004; Goodrich et al., 1996). Previous studies have identified a role for the HH signaling pathway in regulating progenitor cell proliferation and angiogenesis (Singh et al., 2015; Singh et al., 2012). Global deletion of the ligand, Sonic hedgehog, and/or its G protein-coupled receptor, Smoothened (Smo), resulted in early embryonic lethality and perturbed cardiogenesis in the mouse (Zhang et al., 2001) Similarly, gene disruption studies of the HH downstream effectors (Gli1/Gli2/Gli3) demonstrated perturbed cardiogenesis ((Kim et al., 2001). Previous studies have shown that the role and expression of the Gli transcription factors are context dependent (Hu et al., 2006; Park et al., 2000). These studies support the notion that Gli1 and Gli2 have overlapping functions as transcriptional activators, whereas Gli3 functions, in a context-dependent fashion, to repress HH signaling. The present studies support the hypothesis that HH/Gli1-dependent developmental mechanisms that govern embryogenesis are also operational during the regenerative process and are mechanistic drivers for the regeneration of postnatal tissues. Therefore, the role of Gli1 from its role during development to its role in cardiac repair has been expanded.

The role of Mycn as a downstream target of Gli1 was also defined. Mycn is a proto-oncogene that encodes a protein that has a basic helix-loop-helix DNA-binding domain (Knoepfler et al., 2002). Mycn mutations are associated with Feingold syndrome, which is a disorder associated with congenital heart defects (Marcelis et al., 2008). Global as well as cardiac-specific deletion of Mycn locus results in lethality by midgestational age and displays growth retardation and perturbed cardiogenesis (Harmelink et al., 2013; Charron et al., 1992). While there are functional redundancies associated with Myc family members, the overall homology between Mycn and c-Myc is only about 30%, suggesting that specific domains harbor functions for these proteins for the growth and development of specific lineages (Malynn et al., 2000). In the present study, Mycn was defined as a direct downstream target of Gli1. Moreover, the impact of a hedgehog-Gli1-Mycn cascade as an inducer of cardiomyocyte proliferation and a facilitator of heart regeneration following injury was defined.

The essential nature of evolutionary conserved signaling pathways that can be deciphered using emerging bioinformatics algorithms, which can then be coupled with pharmacological and genetic technologies in mammalian organisms, was also shown. In the present study, the Bootstrap algorithm was used to interrogate cardiac regeneration in the adult newt. This strategy was used to identify candidate factors/pathways that were induced and had sustained expression during cardiac regeneration. While this bioinformatics strategy successfully identified the hedgehog signaling pathway, other signaling pathways were also identified and warrant further examination. The present studies also used the neonatal mouse heart, hiPSC-derived cardiomyocytes, and genetic mouse models, which are powerful models to examine the impact of evolutionary conserved factors and their impact on cardiomyocyte proliferation. The neonatal mouse heart has a tremendous regenerative capacity which is rapidly extinguished by P7 following birth[12]. This regenerative model may serve as an extension of the developmental programs expressed during embryogenesis and is a powerful model to define regulators that promote cardiomyocyte proliferation. The regenerative and non-regenerative windows/periods during the postnatal heart development were used to interrogate and the impact of hedgehog signaling and cardiomyocyte proliferation was demonstrated. Multiple reports have described additional roles of HH signaling in the neovascularization and anti-apoptotic process following myocardial ischemia (Kusano et al., 2005; Xin et al. 2011). Based on the present study as well as others, it is possible that HH signaling plays multiple roles including proliferation, vasculogenic and protective functions following injury. The present data indicated that Shh was expressed and secreted as a morphogen by both $CD90^+$- and $CD31^+$-cell populations following injury. Therefore, we propose that Shh morphogen might function as both autocrine as well as paracrine manner, however, overexpression of Shh alone in these cells might not be sufficient to drive the pathway for an effective repair. In this study, we have provided a new mechanistic proliferative pathway mediated via Mycn. Since the levels of both Smoothened and Mycn were low in the adult myocardium, gene therapy and/or mRNA mediated over-expression of these factors could help mediate adult heart regeneration following injury.

In summary, the present studies support the power of using multiple organisms to uncover evolutionary conserved networks that impact cardiomyocyte proliferation and regeneration. These studies also emphasize the importance of examining development pathways that are reexpressed following injury and function to promote regeneration. Moreover, it was found that the HH-Gli1-Mycn regulatory mechanism that facilitates cardiomyocyte proliferation and enhances the understanding of just one of the keys that unlock the myocardial regeneration program. The highly conserved nature of these newly discovered mechanisms suggest the importance of this pathway in promoting cardiac regeneration. Successful induction of this molecular pathway holds unique potential for induction of cardiac regeneration following injury in humans.

Example II

Figure 20:
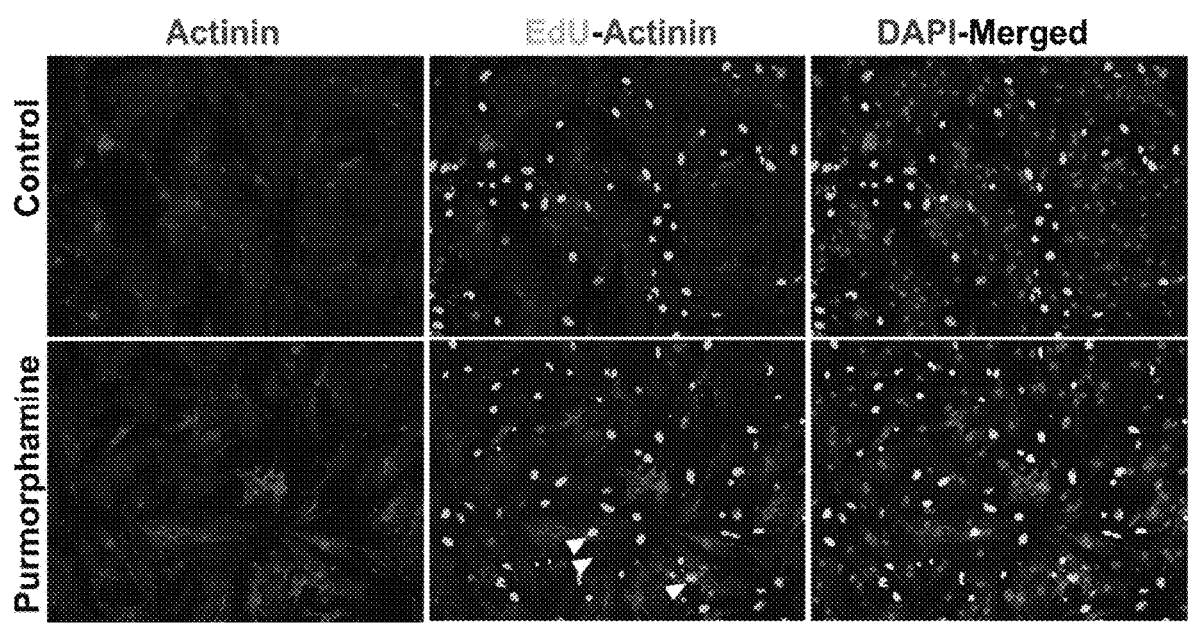
FIG. 20. Purmorphamine promotes cardiomyocyte proliferation. Immunohistochemical images of Actinin$^+$-EdU$^+$ isolated neonatal cardiomyocytes following exposure to control and purmorphamine and pulsed with EdU. Arrowheads show cardiomyocyte (red) positive for EdU (Green). Nuclei are shown in blue.

Agents including but not limited to Gli1, Gli2, Purmorphamine, other small molecules with desirable activity, Mycn and SAG all promote cardiomyocyte proliferation in the mammalian heart and isolated cardiomyocytes (FIG. 20).

Figure 21A:
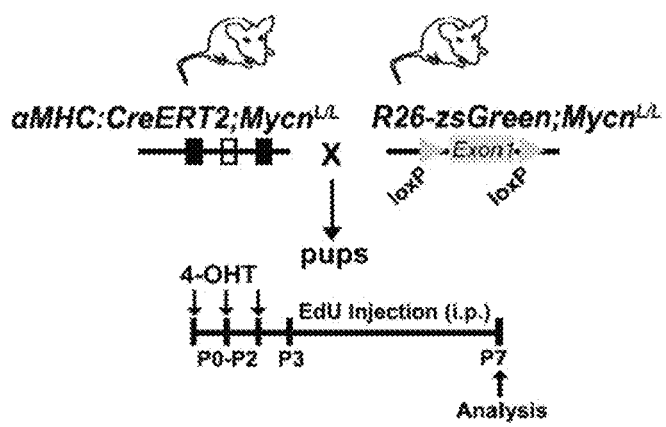
FIGS. 21A-21D. Conditional deletion of Mycn results in impaired development of the neonatal heart. A) Schematic of cardiomyocyte-specific conditional deletion of the floxed-Mycn allele. B) Heart weight to body weight (HW/BW) ratio in control and Mycn CKO mice (n=3 per group). C, D). Whole-mount images of representative control and Mycn CKO pups and hearts obtained by crossing αMHC-CreERT2;Mycn$^{L/L}$ with Rosa26-zsGreen;Mycn$^{L/L}$ mice. Control mice were not injected with 4-hydroxytamoxifen.
Figure 21B:
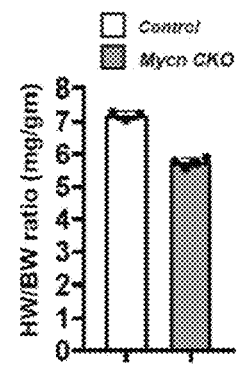
Figure 21C:
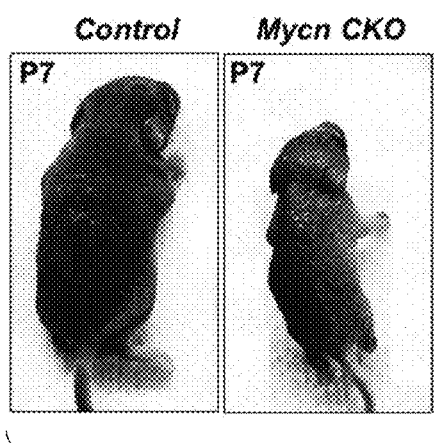
Figure 21D:
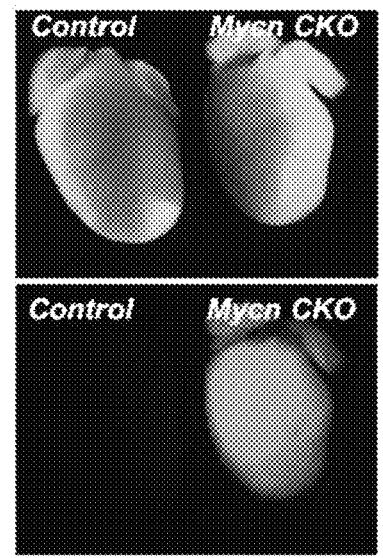

Studies further demonstrated the role of Mycn as a mediator of cardiomyocyte proliferation in the mammalian heart. Using a gene deletion strategy, Mycn expression was ablated using an alpha-MHC-Cre driver in the neonatal heart (following delivery of 4-OHT on P0-P2) (FIG. 21). This experimental strategy is schematized in FIG. 21A and conditionally deleted Mycn only in the heart. Analysis of the Mycn conditional knockouts (Mycn CKO) reveal a smaller heart (FIGS. 21B and 21D).

Using the conditional knockout strategy, it was demonstrated that the alpha MHC (Myh6) strategy was sensitive and comprehensive (FIGS. 22A and 22B). It was further demonstrated that this strategy resulted in an ~80% decrease of Mycn expression (FIG. 22C).

The loss of members of the Shh signaling pathway (e.g., Gli1Gli2, SAG, Small Molecules, Mycn) all impact or ablate the ability of the mammalian heart to grow and development. As outlined in FIG. 23, the conditional knockout of Mycn in the mammalian heart resulted in perturbed growth and decreased heart function (FIG. 23A-C). Collectively, these data provide further evidence that members of the Shh Signaling pathway (Gli1, Gli2, SAG, Small Molecules, Purmorphamine, Mycn) can promote (to regenerate the heart) or repress (following deletion of these genes) cardiomyocyte proliferation in the mammalian heart.

REFERENCES

Adhikari et al., *Biochim. Biophys. Acta*, 1813:1532 (2011).
Aguirre et al., *Cell. Stem Cell*, 15:589 (2014).
Bergmann et al., *Science*, 324:98 (2009).
Borchardt et al., *BMC Genomics*, 11:4 (2010).
Charron et al., *Genes Dev.*, 6:2248 (1992).
Chen et al., *Genes Dev.*, 16:2743 (2002).
Choi et al., *Development*, 140:660 (2013).
Collesi et al., *J. Cell Biol.*, 183:117 (2008).
Dubois et al., *Nat. Biotechnol.*, 29:1011 (2011).
D'Uva et al., *Nat. Cell Biol.*, 17:627 (2015).
Dyer et al., *Dev. Biol.*, 330:305 (2009).
Ferdous et al., *Proc. Natl. Acad. Sci. U.S.A.*, 106:814 (2009).
Gong et al., *Nat. Commun.*, 8:14362 (2017).
Goodrich et al., *Genes Dev.*, 10:301 (1996).
Harmelink et al., *Dev. Biol.*, 373:53 (2013).
Hu et al., *Development*, 133:569 (2006).
Jeong et al., *Genes Dev.*, 18:937 (2004).
Jopling et al., *Nature*, 464:606 (2010).
Kawakami et al., *Genes Dev.*, 20:3232 (2006).
Kikuchi et al., *Dev. Cell*, 20:397 (2011).
Kikuchi et al., *Nature*, 464:601 (2010).
Kim et al., *J. Pediatr. Surg.*, 36:381 (2001).
King et al., *PLoS One*, 11:e0157106, (2016).
Knoepfler et al., *Genes Dev.*, 16:2699 (2002).
Koyano-Nakagawa et al., *J. Biol. Chem.*, 290:25107 (2015).
Koyano-Nakagawa et al., *Stem Cells*, 30:1611 (2012).
Kragl et al., *Nature*, 460:60 (2009).
Kusano et al., *Nat. Med.*, 11:1197 (2005).
Lavine et al., *J. Clin. Invest.*, 118:2404 (2008).
Lee et al., *Development*, 132:5173 (2005).
Lian et al., *Nat. Protoc.*, 8:162 (2013).
Mahmoud et al., *Nature*, 497:249 (2013).
Malynn et al., *Genes Dev.*, 14:1390 (2000).
Marcelis et al., *Hum. Mutat.*, 29:1125 (2008).
Park et al., *Development*, 127:1593 (2000).
Peterson et al., *Genes Dev.*, 26:2802 (2012).
Porrello et al., *Science*, 331:1078 (2011).
Poss et al., *Science*, 298:2188 (2002).
Rasmussen et al., *Development*, 138:4801 (2011).
Robbins et al., *Sci. Signal*, 5:re6 (2012).
Senyo et al., *Nature*, 493:433 (2013).
Singh et al., *Biochim. Biophys. Acta*, 1803:288 (2010).
Singh et al., *Cell Rep.*, 13:915 (2015).
Singh et al., *Dev. Biol.*, 371:23 (2012).
Singh et al., *Genes (Basel)*, 6:417 (2015).
Singh et al., *J. Cardiovasc. Transl. Res.*, 3:397 (2010).
Singh et al., *J. Mol. Biol.*, 366:756 (2007).
Singh et al., *PLoS One*, 12: (2017).
Sohal et al., *Circ. Res.*, 89:20 (2001).
Tiscornia et al., *Nat. Protoc.*, 1:241 (2006).
van Amerongen et al., *J. Cell. Mol. Med.*, 12:2233 (2008).
Washington Smoak et al., *Dev. Biol.*, 283:357 (2005).
Weaver et al., *Regen. Med.*, 3:63 (2008).
Witman et al., *Dev. Biol.*, 354:67 (2011).
Xin et al., *Nat. Rev. Mol. Cell. Biol.*, 14:529 (2013).
Xin et al., *Proc. Natl. Acad. Sci. USA*, 110:13839 (2013).
Xin et al., *Sci. Signal*, 4:ra70 (2011).
Zhang et al., *Cell*, 105:781 (2001).
Zhang et al., *Circ. Res.*, 111:1125 (2012).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. A method to enhance repair or regeneration of a mammalian heart in need thereof comprising:
directly administering to the heart of a mammal a composition comprising an effective amount of nucleic acid that encodes Gli1 or Mycn.

2. The method of claim 1 wherein the mammal is a human.

3. The method of claim 1 wherein the nucleic acid encodes Mycn.

4. The method of claim 1 wherein the nucleic acid is in a recombinant adenovirus, adeno-associated virus, lentivirus, retrovirus, sendai virus or herpesvirus.

5. The method of claim 1 wherein the composition is administered with a catheter.

6. The method of claim 1 wherein the effective amount enhances cardiac regeneration.

7. The method of claim 1 further comprising determining neovascularization, ejection fraction or shortening fraction, or any combination thereof.

8. The method of claim 1 wherein the mammal has heart failure, a heart injury, a myocardial infarction, a vascular disease, or a cardiac arrhythmia.

9. The method of claim 1 further comprising determining fibrosis or scar formation.

10. The method of claim 1 further comprising determining epicardial cell, cardiomyocyte, endothelial cell or vascular cell proliferation.

11. The method of claim 1 wherein the mammal has a cardiac injury.

12. The method of claim 1 wherein the composition is administered after a myocardial infarction.

13. The method of claim 1 wherein the agent is intracardially administered.

14. The method of claim 1 wherein the nucleic acid comprises RNA.

15. The method of claim 1 wherein the nucleic acid encodes Gli1.

* * * * *

SEQUENCE LISTING

```
<160> NUMBER OF SEQ ID NOS: 24

<210> SEQ ID NO 1
<211> LENGTH: 787
<212> TYPE: PRT
<213> ORGANISM: Mus musculus

<400> SEQUENCE: 1

Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
                20                  25                  30

Ser Gly Asn Ala Thr Gly Pro Gly Pro Arg Ser Ala Gly Gly Ser Ala
            35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95
```

```
Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125

Val Tyr Met Pro Lys Cys Glu Asn Asp Arg Val Glu Leu Pro Ser Arg
    130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
            180                 185                 190

Cys Glu Val Pro Leu Val Arg Thr Asp Asn Pro Lys Ser Trp Tyr Glu
        195                 200                 205

Asp Val Glu Gly Cys Gly Ile Gln Cys Gln Asn Pro Leu Phe Thr Glu
    210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
            260                 265                 270

Cys Phe Phe Val Gly Ser Ile Gly Trp Leu Ala Gln Phe Met Asp Gly
        275                 280                 285

Ala Arg Arg Glu Ile Val Cys Arg Ala Asp Gly Thr Met Arg Leu Gly
    290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
            340                 345                 350

Leu Ser Gly Lys Thr Ser Tyr Phe His Leu Leu Thr Trp Ser Leu Pro
        355                 360                 365

Phe Val Leu Thr Val Ala Ile Leu Ala Val Ala Gln Val Asp Gly Asp
    370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
            420                 425                 430

His Pro Gly Leu Leu Ser Glu Lys Ala Ala Ser Lys Ile Asn Glu Thr
        435                 440                 445

Met Leu Arg Leu Gly Ile Phe Gly Phe Leu Ala Phe Gly Phe Val Leu
    450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
            500                 505                 510
```

```
Pro Ser Leu Leu Val Glu Lys Ile Asn Leu Phe Ala Met Phe Gly Thr
            515                 520                 525

Gly Ile Ala Met Ser Thr Trp Val Trp Thr Lys Ala Thr Leu Leu Ile
        530                 535                 540

Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Gln Ala Asn Leu Trp Leu
                645                 650                 655

Val Glu Ala Glu Ile Ser Pro Glu Leu Gln Lys Arg Leu Gly Arg Lys
                660                 665                 670

Lys Lys Arg Arg Lys Arg Lys Lys Glu Val Cys Pro Leu Ala Pro Pro
                675                 680                 685

Pro Glu Leu His Pro Pro Ala Pro Ala Pro Ser Thr Ile Pro Arg Leu
            690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
                740                 745                 750

Pro Ala Pro Val Ala Trp Ala His Gly Arg Arg Gln Gly Leu Gly Pro
            755                 760                 765

Ile His Ser Arg Thr Asn Leu Met Asp Thr Glu Leu Met Asp Ala Asp
    770                 775                 780

Ser Asp Phe
785

<210> SEQ ID NO 2
<211> LENGTH: 1447
<212> TYPE: PRT
<213> ORGANISM: Mus musculus

<400> SEQUENCE: 2

Met Ala Ser Ala Gly Asn Ala Ala Glu Pro Gln Asp Arg Gly Gly Gly
1               5                   10                  15

Gly Ser Gly Cys Ile Gly Ala Pro Gly Arg Pro Ala Gly Gly Arg
            20                  25                  30

Arg Arg Arg Thr Gly Gly Leu Arg Arg Ala Ala Pro Asp Arg Asp
        35                  40                  45

Tyr Leu His Arg Pro Ser Tyr Cys Asp Ala Ala Phe Ala Leu Glu Gln
    50                  55                  60

Ile Ser Lys Gly Lys Ala Thr Gly Arg Lys Ala Pro Leu Trp Leu Arg
65                  70                  75                  80

Ala Lys Phe Gln Arg Leu Leu Phe Lys Leu Gly Cys Tyr Ile Gln Lys
                85                  90                  95
```

```
Asn Cys Gly Lys Phe Leu Val Val Gly Leu Ile Phe Gly Ala Phe
                100                 105                 110

Ala Val Gly Leu Lys Ala Ala Asn Leu Glu Thr Asn Val Glu Glu Leu
        115                 120                 125

Trp Val Glu Val Gly Gly Arg Val Ser Arg Glu Leu Asn Tyr Thr Arg
        130                 135                 140

Gln Lys Ile Gly Glu Glu Ala Met Phe Asn Pro Gln Leu Met Ile Gln
145                 150                 155                 160

Thr Pro Lys Glu Glu Gly Ala Asn Val Leu Thr Thr Glu Ala Leu Leu
                165                 170                 175

Gln His Leu Asp Ser Ala Leu Gln Ala Ser Arg Val His Val Tyr Met
                180                 185                 190

Tyr Asn Arg Gln Trp Lys Leu Glu His Leu Cys Tyr Lys Ser Gly Glu
        195                 200                 205

Leu Ile Thr Glu Thr Gly Tyr Met Asp Gln Ile Ile Glu Tyr Leu Tyr
        210                 215                 220

Pro Cys Leu Ile Ile Thr Pro Leu Asp Cys Phe Trp Glu Gly Ala Lys
225                 230                 235                 240

Leu Gln Ser Gly Thr Ala Tyr Leu Leu Gly Lys Pro Pro Leu Arg Trp
                245                 250                 255

Thr Asn Phe Asp Pro Leu Glu Phe Leu Glu Glu Leu Lys Lys Ile Asn
                260                 265                 270

Tyr Gln Val Asp Ser Trp Glu Glu Met Leu Asn Lys Ala Glu Val Gly
        275                 280                 285

His Gly Tyr Met Asp Arg Pro Cys Leu Asn Pro Ala Asp Pro Asp Cys
        290                 295                 300

Pro Ala Thr Ala Pro Asn Lys Asn Ser Thr Lys Pro Leu Asp Met Ala
305                 310                 315                 320

Leu Val Leu Asn Gly Gly Cys His Gly Leu Ser Arg Lys Tyr Met His
                325                 330                 335

Trp Gln Glu Glu Leu Ile Val Gly Gly Thr Val Lys Asn Ser Thr Gly
        340                 345                 350

Lys Leu Val Ser Ala His Ala Leu Gln Thr Met Phe Gln Leu Met Thr
        355                 360                 365

Pro Lys Gln Met Tyr Glu His Phe Lys Gly Tyr Glu Tyr Val Ser His
        370                 375                 380

Ile Asn Trp Asn Glu Asp Lys Ala Ala Ala Ile Leu Glu Ala Trp Gln
385                 390                 395                 400

Arg Thr Tyr Val Glu Val Val His Gln Ser Val Ala Gln Asn Ser Thr
                405                 410                 415

Gln Lys Val Leu Ser Phe Thr Thr Thr Thr Leu Asp Asp Ile Leu Lys
                420                 425                 430

Ser Phe Ser Asp Val Ser Val Ile Arg Val Ala Ser Gly Tyr Leu Leu
        435                 440                 445

Met Leu Ala Tyr Ala Cys Leu Thr Met Leu Arg Trp Asp Cys Ser Lys
        450                 455                 460

Ser Gln Gly Ala Val Gly Leu Ala Gly Val Leu Leu Val Ala Leu Ser
465                 470                 475                 480

Val Ala Ala Gly Leu Gly Leu Cys Ser Leu Ile Gly Ile Ser Phe Asn
                485                 490                 495

Ala Ala Thr Thr Gln Val Leu Pro Phe Leu Ala Leu Gly Val Gly Val
                500                 505                 510
```

-continued

```
Asp Asp Val Phe Leu Leu Ala His Ala Phe Ser Glu Thr Gly Gln Asn
            515                 520                 525

Lys Arg Ile Pro Phe Glu Asp Arg Thr Gly Glu Cys Leu Lys Arg Thr
530                 535                 540

Gly Ala Ser Val Ala Leu Thr Ser Ile Ser Asn Val Thr Ala Phe Phe
545                 550                 555                 560

Met Ala Ala Leu Ile Pro Ile Pro Ala Leu Arg Ala Phe Ser Leu Gln
                565                 570                 575

Ala Ala Val Val Val Phe Asn Ala Met Val Leu Leu Ile Phe
                580                 585                 590

Pro Ala Ile Leu Ser Met Asp Leu Tyr Arg Arg Glu Asp Arg Arg Leu
            595                 600                 605

Asp Ile Phe Cys Cys Phe Thr Ser Pro Cys Val Ser Arg Val Ile Gln
            610                 615                 620

Val Glu Pro Gln Ala Tyr Thr Asp Thr His Asp Asn Thr Arg Tyr Ser
625                 630                 635                 640

Pro Pro Pro Pro Tyr Ser Ser His Ser Phe Ala His Glu Thr Gln Ile
                645                 650                 655

Thr Met Gln Ser Thr Val Gln Leu Arg Thr Glu Tyr Asp Pro His Thr
                660                 665                 670

His Val Tyr Tyr Thr Thr Ala Glu Pro Arg Ser Glu Ile Ser Val Gln
            675                 680                 685

Pro Val Thr Val Thr Gln Asp Thr Leu Ser Cys Gln Ser Pro Glu Ser
            690                 695                 700

Thr Ser Ser Thr Arg Asp Leu Leu Ser Gln Phe Ser Asp Ser Ser Leu
705                 710                 715                 720

His Cys Leu Glu Pro Pro Cys Thr Lys Trp Thr Leu Ser Ser Phe Ala
                725                 730                 735

Glu Lys His Tyr Ala Pro Phe Leu Leu Lys Pro Lys Ala Lys Val Val
                740                 745                 750

Val Ile Phe Leu Phe Leu Gly Leu Leu Gly Val Ser Leu Tyr Gly Thr
            755                 760                 765

Thr Arg Val Arg Asp Gly Leu Asp Leu Thr Asp Ile Val Pro Arg Glu
            770                 775                 780

Thr Arg Glu Tyr Asp Phe Ile Ala Ala Gln Phe Lys Tyr Phe Ser Phe
785                 790                 795                 800

Tyr Asn Met Tyr Ile Val Thr Gln Lys Ala Asp Tyr Pro Asn Ile Gln
                805                 810                 815

His Leu Leu Tyr Asp Leu His Arg Ser Phe Ser Asn Val Lys Tyr Val
                820                 825                 830

Met Leu Glu Glu Asn Lys Gln Leu Pro Lys Met Trp Leu His Tyr Phe
            835                 840                 845

Arg Asp Trp Leu Gln Gly Leu Gln Asp Ala Phe Asp Ser Asp Trp Glu
850                 855                 860

Thr Gly Lys Ile Met Pro Asn Asn Tyr Lys Asn Gly Ser Asp Asp Gly
865                 870                 875                 880

Val Leu Ala Tyr Lys Leu Leu Val Gln Thr Gly Ser Arg Asp Lys Pro
                885                 890                 895

Ile Asp Ile Ser Gln Leu Thr Lys Gln Arg Leu Val Asp Ala Asp Gly
                900                 905                 910

Ile Ile Asn Pro Ser Ala Phe Tyr Ile Tyr Leu Thr Ala Trp Val Ser
            915                 920                 925
```

```
Asn Asp Pro Val Ala Tyr Ala Ser Gln Ala Asn Ile Arg Pro His
    930                 935                 940

Arg Pro Glu Trp Val His Asp Lys Ala Asp Tyr Met Pro Glu Thr Arg
945                 950                 955                 960

Leu Arg Ile Pro Ala Ala Glu Pro Ile Glu Tyr Ala Gln Phe Pro Phe
                965                 970                 975

Tyr Leu Asn Gly Leu Arg Asp Thr Ser Asp Phe Val Glu Ala Ile Glu
            980                 985                 990

Lys Val Arg Thr Ile Cys Ser Asn Tyr Thr Ser Leu Gly Leu Ser Ser
        995                 1000                1005

Tyr Pro Asn Gly Tyr Pro Phe Leu Phe Trp Glu Gln Tyr Ile Gly Leu
    1010                1015                1020

Arg His Trp Leu Leu Leu Phe Ile Ser Val Val Leu Ala Cys Thr Phe
1025                1030                1035                1040

Leu Val Cys Ala Val Phe Leu Leu Asn Pro Trp Thr Ala Gly Ile Ile
                1045                1050                1055

Val Met Val Leu Ala Leu Met Thr Val Glu Leu Phe Gly Met Met Gly
            1060                1065                1070

Leu Ile Gly Ile Lys Leu Ser Ala Val Pro Val Val Ile Leu Ile Ala
        1075                1080                1085

Ser Val Gly Ile Gly Val Glu Phe Thr Val His Val Ala Leu Ala Phe
    1090                1095                1100

Leu Thr Ala Ile Gly Asp Lys Asn Arg Arg Ala Val Leu Ala Leu Glu
1105                1110                1115                1120

His Met Phe Ala Pro Val Leu Asp Gly Ala Val Ser Thr Leu Leu Gly
                1125                1130                1135

Val Leu Met Leu Ala Gly Ser Glu Phe Asp Phe Ile Val Arg Tyr Phe
            1140                1145                1150

Phe Ala Val Leu Ala Ile Leu Thr Ile Leu Gly Val Leu Asn Gly Leu
        1155                1160                1165

Val Leu Leu Pro Val Leu Leu Ser Phe Phe Gly Pro Tyr Pro Glu Val
    1170                1175                1180

Ser Pro Ala Asn Gly Leu Asn Arg Leu Pro Thr Pro Ser Pro Glu Pro
1185                1190                1195                1200

Pro Pro Ser Val Val Arg Phe Ala Met Pro Pro Gly His Thr His Ser
                1205                1210                1215

Gly Ser Asp Ser Ser Asp Ser Glu Tyr Ser Ser Gln Thr Thr Val Ser
            1220                1225                1230

Gly Leu Ser Glu Glu Leu Arg His Tyr Glu Ala Gln Gln Gly Ala Gly
        1235                1240                1245

Gly Pro Ala His Gln Val Ile Val Glu Ala Thr Glu Asn Pro Val Phe
    1250                1255                1260

Ala His Ser Thr Val Val His Pro Glu Ser Arg His His Pro Pro Ser
1265                1270                1275                1280

Asn Pro Arg Gln Gln Pro His Leu Asp Ser Gly Ser Leu Pro Pro Gly
                1285                1290                1295

Arg Gln Gly Gln Gln Pro Arg Arg Asp Pro Arg Glu Gly Leu Trp
            1300                1305                1310

Pro Pro Pro Tyr Arg Pro Arg Arg Asp Ala Phe Glu Ile Ser Thr Glu
        1315                1320                1325

Gly His Ser Gly Pro Ser Asn Arg Ala Arg Trp Gly Pro Arg Gly Ala
    1330                1335                1340
```

-continued

```
Arg Ser His Asn Pro Arg Asn Pro Ala Ser Thr Ala Met Gly Ser Ser
1345                1350                1355                1360

Val Pro Gly Tyr Cys Gln Pro Ile Thr Thr Val Thr Ala Ser Ala Ser
            1365                1370                1375

Val Thr Val Ala Val His Pro Pro Val Pro Gly Pro Gly Arg Asn
        1380                1385                1390

Pro Arg Gly Gly Leu Cys Pro Gly Tyr Pro Glu Thr Asp His Gly Leu
        1395                1400                1405

Phe Glu Asp Pro His Val Pro Phe His Val Arg Cys Glu Arg Arg Asp
    1410                1415                1420

Ser Lys Val Glu Val Ile Glu Leu Gln Asp Val Glu Cys Glu Arg
1425                1430                1435                1440

Pro Arg Gly Ser Ser Ser Asn
            1445

<210> SEQ ID NO 3
<211> LENGTH: 462
<212> TYPE: PRT
<213> ORGANISM: Mus musculus

<400> SEQUENCE: 3

Met Leu Leu Leu Ala Arg Cys Leu Leu Val Leu Val Ser Ser Leu
1               5                   10                  15

Leu Val Cys Ser Gly Leu Ala Cys Gly Pro Gly Arg Gly Phe Gly Lys
            20                  25                  30

Arg Arg His Pro Lys Lys Leu Thr Pro Leu Ala Tyr Lys Gln Phe Ile
        35                  40                  45

Pro Asn Val Ala Glu Lys Thr Leu Gly Ala Ser Gly Arg Tyr Glu Gly
    50                  55                  60

Lys Ile Ser Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ala Leu Ala Ile Ser
            100                 105                 110

Val Met Asn Gln Trp Pro Gly Val Lys Leu Arg Val Thr Glu Gly Trp
        115                 120                 125

Asp Glu Asp Gly His His Ser Glu Glu Ser Leu His Tyr Glu Gly Arg
    130                 135                 140

Ala Val Asp Ile Thr Thr Ser Asp Arg Asp Arg Ser Lys Tyr Gly Met
145                 150                 155                 160

Leu Ala Arg Leu Ala Val Glu Ala Gly Phe Asp Trp Val Tyr Tyr Glu
                165                 170                 175

Ser Lys Ala His Ile His Cys Ser Val Lys Ala Glu Asn Ser Val Ala
            180                 185                 190

Ala Lys Ser Gly Gly Cys Phe Pro Gly Ser Ala Thr Val His Leu Glu
        195                 200                 205

Gln Gly Gly Thr Lys Leu Val Lys Asp Leu Ser Pro Gly Asp Arg Val
    210                 215                 220

Leu Ala Ala Asp Asp Gln Gly Arg Leu Leu Tyr Ser Asp Phe Leu Thr
225                 230                 235                 240

Phe Leu Asp Arg Asp Asp Gly Ala Lys Lys Val Phe Tyr Val Ile Glu
                245                 250                 255

Thr Arg Glu Pro Arg Glu Arg Leu Leu Leu Thr Ala Ala His Leu Leu
            260                 265                 270
```

```
Phe Val Ala Pro His Asn Asp Ser Ala Thr Gly Glu Pro Glu Ala Ser
            275                 280                 285

Ser Gly Ser Gly Pro Pro Ser Gly Gly Ala Leu Gly Pro Arg Ala Leu
        290                 295                 300

Phe Ala Ser Arg Val Arg Pro Gly Gln Arg Val Tyr Val Val Ala Glu
305                 310                 315                 320

Arg Asp Gly Asp Arg Arg Leu Leu Pro Ala Ala Val His Ser Val Thr
                325                 330                 335

Leu Ser Glu Glu Ala Ala Gly Ala Tyr Ala Pro Leu Thr Ala Gln Gly
            340                 345                 350

Thr Ile Leu Ile Asn Arg Val Leu Ala Ser Cys Tyr Ala Val Ile Glu
        355                 360                 365

Glu His Ser Trp Ala His Arg Ala Phe Ala Pro Phe Arg Leu Ala His
    370                 375                 380

Ala Leu Leu Ala Ala Leu Ala Pro Ala Arg Thr Asp Arg Gly Gly Asp
385                 390                 395                 400

Ser Gly Gly Gly Asp Arg Gly Gly Gly Gly Arg Val Ala Leu Thr
                405                 410                 415

Ala Pro Gly Ala Ala Asp Ala Pro Gly Ala Gly Ala Thr Ala Gly Ile
            420                 425                 430

His Trp Tyr Ser Gln Leu Leu Tyr Gln Ile Gly Thr Trp Leu Leu Asp
        435                 440                 445

Ser Glu Ala Leu His Pro Leu Gly Met Ala Val Lys Ser Ser
    450                 455                 460

<210> SEQ ID NO 4
<211> LENGTH: 1106
<212> TYPE: PRT
<213> ORGANISM: Mus musculus

<400> SEQUENCE: 4

Met Phe Asn Ser Met Thr Pro Pro Ile Ser Ser Tyr Gly Glu Pro
1               5                   10                  15

Cys Cys Leu Arg Pro Leu Pro Ser Gln Gly Ala Pro Ser Val Gly Thr
            20                  25                  30

Glu Gly Leu Ser Gly Pro Pro Phe Cys His Gln Ala Asn Leu Met Ser
        35                  40                  45

Gly Pro His Ser Tyr Gly Pro Ala Arg Glu Thr Asn Ser Cys Thr Glu
    50                  55                  60

Gly Pro Leu Phe Ser Ser Pro Arg Ser Ala Val Lys Leu Thr Lys Lys
65                  70                  75                  80

Arg Ala Leu Ser Ile Ser Pro Leu Ser Asp Ala Ser Leu Asp Leu Gln
                85                  90                  95

Thr Val Ile Arg Thr Ser Pro Ser Ser Leu Val Ala Phe Ile Asn Ser
            100                 105                 110

Arg Cys Thr Ser Pro Gly Gly Ser Tyr Gly His Leu Ser Ile Gly Thr
        115                 120                 125

Met Ser Pro Ser Leu Gly Phe Pro Ala Gln Met Asn His Gln Lys Gly
    130                 135                 140

Pro Ser Pro Ser Phe Gly Val Gln Pro Cys Gly Pro His Asp Ser Ala
145                 150                 155                 160

Arg Gly Gly Met Ile Pro His Pro Gln Ser Arg Gly Pro Phe Pro Thr
                165                 170                 175

Cys Gln Leu Lys Ser Glu Leu Asp Met Leu Val Gly Lys Cys Arg Glu
            180                 185                 190
```

```
Glu Pro Leu Glu Gly Asp Met Ser Pro Asn Ser Thr Gly Ile Gln
        195                 200                 205

Asp Pro Leu Leu Gly Met Leu Asp Gly Arg Glu Asp Leu Glu Arg Glu
210                 215                 220

Glu Lys Arg Glu Pro Glu Ser Val Tyr Glu Thr Asp Cys Arg Trp Asp
225                 230                 235                 240

Gly Cys Ser Gln Glu Phe Asp Ser Gln Glu Gln Leu Val His His Ile
                245                 250                 255

Asn Ser Glu His Ile His Gly Glu Arg Lys Glu Phe Val Cys His Trp
                260                 265                 270

Gly Gly Cys Ser Arg Glu Leu Arg Pro Phe Lys Ala Gln Tyr Met Leu
            275                 280                 285

Val Val His Met Arg Arg His Thr Gly Glu Lys Pro His Lys Cys Thr
        290                 295                 300

Phe Glu Gly Cys Arg Lys Ser Tyr Ser Arg Leu Glu Asn Leu Lys Thr
305                 310                 315                 320

His Leu Arg Ser His Thr Gly Glu Lys Pro Tyr Met Cys Glu His Glu
                325                 330                 335

Gly Cys Ser Lys Ala Phe Ser Asn Ala Ser Asp Arg Ala Lys His Gln
            340                 345                 350

Asn Arg Thr His Ser Asn Glu Lys Pro Tyr Val Cys Lys Leu Pro Gly
        355                 360                 365

Cys Thr Lys Arg Tyr Thr Asp Pro Ser Ser Leu Arg Lys His Val Lys
370                 375                 380

Thr Val His Gly Pro Asp Ala His Val Thr Lys Arg His Arg Gly Asp
385                 390                 395                 400

Gly Pro Leu Pro Arg Ala Pro Ser Ile Ser Thr Val Glu Pro Lys Arg
                405                 410                 415

Glu Arg Glu Gly Gly Pro Ile Arg Glu Glu Ser Arg Leu Thr Val Pro
            420                 425                 430

Glu Gly Ala Met Lys Pro Gln Pro Ser Pro Gly Ala Gln Ser Ser Cys
        435                 440                 445

Ser Ser Asp His Ser Pro Ala Gly Ser Ala Ala Asn Thr Asp Ser Gly
450                 455                 460

Val Glu Met Thr Gly Asn Ala Gly Gly Ser Thr Glu Asp Leu Ser Ser
465                 470                 475                 480

Leu Asp Glu Gly Pro Cys Ile Ala Gly Thr Gly Leu Ser Thr Leu Arg
                485                 490                 495

Arg Leu Glu Asn Leu Arg Leu Asp Gln Leu His Gln Leu Arg Pro Ile
            500                 505                 510

Gly Thr Arg Gly Leu Lys Leu Pro Ser Leu Ser His Thr Gly Thr Thr
        515                 520                 525

Val Ser Arg Arg Val Gly Pro Pro Val Ser Leu Glu Arg Arg Ser Ser
530                 535                 540

Ser Ser Ser Ser Ile Ser Ser Ala Tyr Thr Val Ser Arg Arg Ser Ser
545                 550                 555                 560

Leu Ala Ser Pro Phe Pro Pro Gly Ser Pro Glu Asn Gly Ala Ser
                565                 570                 575

Ser Leu Pro Gly Leu Met Pro Ala Gln His Tyr Leu Leu Arg Ala Arg
            580                 585                 590

Tyr Ala Ser Ala Arg Gly Gly Gly Thr Ser Pro Thr Ala Ala Ser Ser
        595                 600                 605
```

```
Leu Asp Arg Ile Gly Gly Leu Pro Met Pro Pro Trp Arg Ser Arg Ala
610                 615                 620
Glu Tyr Pro Gly Tyr Asn Pro Asn Ala Gly Val Thr Arg Arg Ala Ser
625                 630                 635                 640
Asp Pro Ala Gln Ala Ala Asp Arg Pro Ala Pro Ala Arg Val Gln Arg
                645                 650                 655
Phe Lys Ser Leu Gly Cys Val His Thr Pro Thr Val Ala Gly Gly
                660                 665                 670
Gly Gln Asn Phe Asp Pro Tyr Leu Pro Thr Ser Val Tyr Ser Pro Gln
                675                 680                 685
Pro Pro Ser Ile Thr Glu Asn Ala Ala Met Asp Ala Arg Gly Leu Gln
690                 695                 700
Glu Glu Pro Glu Val Gly Thr Ser Met Val Gly Ser Gly Leu Asn Pro
705                 710                 715                 720
Tyr Met Asp Phe Pro Pro Thr Asp Thr Leu Gly Tyr Gly Gly Pro Glu
                725                 730                 735
Gly Ala Ala Ala Glu Pro Tyr Gly Ala Arg Gly Pro Gly Ser Leu Pro
                740                 745                 750
Leu Gly Pro Gly Pro Pro Thr Asn Tyr Gly Pro Asn Pro Cys Pro Gln
                755                 760                 765
Gln Ala Ser Tyr Pro Asp Pro Thr Gln Glu Thr Trp Gly Glu Phe Pro
770                 775                 780
Ser His Ser Gly Leu Tyr Pro Gly Pro Lys Ala Leu Gly Gly Thr Tyr
785                 790                 795                 800
Ser Gln Cys Pro Arg Leu Glu His Tyr Gly Gln Val Gln Val Lys Pro
                805                 810                 815
Glu Gln Gly Cys Pro Val Gly Ser Asp Ser Thr Gly Leu Ala Pro Cys
                820                 825                 830
Leu Asn Ala His Pro Ser Glu Gly Pro Pro His Pro Gln Pro Leu Phe
                835                 840                 845
Ser His Tyr Pro Gln Pro Ser Pro Pro Gln Tyr Leu Gln Ser Gly Pro
850                 855                 860
Tyr Thr Gln Pro Pro Pro Asp Tyr Leu Pro Ser Glu Pro Arg Pro Cys
865                 870                 875                 880
Leu Asp Phe Asp Ser Pro Thr His Ser Thr Gly Gln Leu Lys Ala Gln
                885                 890                 895
Leu Val Cys Asn Tyr Val Gln Ser Gln Gln Glu Leu Leu Trp Glu Gly
                900                 905                 910
Gly Gly Arg Glu Asp Ala Pro Ala Gln Glu Pro Ser Tyr Gln Ser Pro
                915                 920                 925
Lys Phe Leu Gly Asp Ser Gln Val Ser Pro Ser Arg Ala Lys Ala Pro
930                 935                 940
Val Asn Thr Tyr Gly Pro Gly Phe Gly Pro Asn Leu Pro Asn His Lys
945                 950                 955                 960
Ser Gly Ser Tyr Pro Thr Pro Ser Pro Cys His Glu Asn Phe Val Val
                965                 970                 975
Gly Ala Asn Arg Ala Ser His Arg Ala Ala Pro Arg Leu Leu
                980                 985                 990
Pro Pro Leu Pro Thr Cys Tyr Gly Pro Leu Lys Val Gly Gly Thr Asn
                995                 1000                1005
Pro Ser Cys Gly His Pro Glu Val Gly Arg Leu Gly Gly Gly Pro Ala
                1010                1015                1020
```

Leu Tyr Pro Pro Pro Glu Gly Gln Val Cys Asn Pro Leu Asp Ser Leu
1025                1030                1035                1040

Asp Leu Asp Asn Thr Gln Leu Asp Phe Val Ala Ile Leu Asp Glu Pro
                1045                1050                1055

Gln Gly Leu Ser Pro Pro Ser His Asp Gln Arg Gly Ser Ser Gly
                1060                1065                1070

His Thr Pro Pro Pro Ser Gly Pro Pro Asn Met Ala Val Gly Asn Met
            1075                1080                1085

Ser Val Leu Leu Arg Ser Leu Pro Gly Glu Thr Gln Phe Leu Asn Ser
            1090                1095                1100

Ser Ala
1105

<210> SEQ ID NO 5
<211> LENGTH: 464
<212> TYPE: PRT
<213> ORGANISM: Mus musculus

<400> SEQUENCE: 5

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ala Ser Pro Ala Gly Arg
145                 150                 155                 160

Gly His Gly Gly Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Glu Glu Glu Asp
            260                 265                 270

Glu Glu Glu Glu Ile Asp Val Val Thr Val Glu Lys Arg Arg Ser Ser
        275                 280                 285

```
Ser Asn Thr Lys Ala Val Thr Thr Phe Thr Ile Thr Val Arg Pro Lys
    290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
    370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Lys Ile Glu His Ala Arg Thr Cys
    450                 455                 460

<210> SEQ ID NO 6
<211> LENGTH: 3977
<212> TYPE: DNA
<213> ORGANISM: Mus musculus

<400> SEQUENCE: 6
ccagctagag caacaaagga gcccggtagt cggcagggag agctcagggg gctgcggcgc      60
gctcgcgcgg aggtggctgc tgggccgcgg gctggcgtgg gggcggagcc ggggacccac     120
tcccgcaccc cccccccccc ccggccggcc gcctggcctc catcgagggg ctgggagtcg     180
gttttaatgg tgggagaggg aatggggctg gagatcgggg ccccggaggg ttcccagggt     240
tgaagacagc ttcgatctcc aggccaggga gtccgggggtc tgtgcatcct ggcccgggcc     300
tgcgctgctc aacatggggc ccgggttcca aagtttgcaa agttgggagt cgaggggccc     360
ggacgcgcgc ggcgcctggc gaaagctggc cccagacttt cggggcgcac cggtcgccta     420
agtagcctcc gcggcccccg ggtcgtgtg tgtggccagg ggactccggg gagctccggg     480
gcgcctcagc ttttgctgag ttggctgttt ggccatggcc gctggccgcc ccgtgcgtgg     540
gcccgagctg gcgccccgga ggctgctgca gttgctgctg ctggtactgc tggggggccc     600
gggccggggg gcggccttga gcgggaacgt gaccgggcct gggcctcaca gcgccagcgg     660
gagctcgagg agggacgtgc cggtgaccag ccctccgccg ccgctgctga gccactgcgg     720
ccgggccgcc cactgcgagc cttttgcgcta caacgtgtgc ctgggctcgg cgctgcccta     780
cggagccacc accacgctgc tggctgggga ctcggactcg caggaggaag cgcacggcaa     840
gctcgtgctc tggtccggcc tccgaatgc ccccgctgc tgggcagtga tccagccccct     900 gctgtgtgct gtctacatgc caagtgtga aatgaccga gtggagttgc ccagccgtac     960
cctctgccag gccacccgag gccctgtgc cattgtggag cgggagcgag ggtggcctga    1020 cttcttctgcgt tgcacaccgg accacttccc tgaaggctgc ccaaacgagg tacaaaacat    1080
caagttcaac agctcaggcc aatgtgaagc acccttggtg cgaacagaca ccccaagag    1140
```

```
ctggtatgag gacgtggagg gctgtgggat tcagtgtcag aacccgctgt tcaccgaggc    1200
cgagcaccag gacatgcaca gctacatcgc agccttcggg gcggtcactg gtctctgcac    1260
gctcttcaca ctggccacct tgtggctga ctggcggaac tccaatcgct accctgcggt     1320
tattctcttc tatgtcaatg cgtgtttctt cgtgggcagc attggctggc tggcccagtt    1380
catggatggt gcccgccgag agattgtttg ccgagcagat ggcaccatga gatttgggga    1440
gcccacctcc agtgagaccc tgtcctgtgt catcatcttt gtcattgtgt actatgcctt    1500
gatggctgga gtagtctggt tcgtggtcct cacctatgcc tggcacacct ccttcaaagc    1560
cctgggcacc acctaccagc ctctctcggg caagacatcc tatttccacc tgctcacgtg    1620
gtcactcccc tttgtcctca cggtggcaat cctggctgtg gctcaggtag atggagactc    1680
cgtgagtggc atctgttttg taggctacaa gaactatcgg taccgtgctg gctttgtcct    1740
ggccccaatt ggcctggtgc ttattgtggg aggctacttc ctcatcagag gggtcatgac    1800
tctgttctcc atcaagagca accacccctgg gcttctgagt gagaaggcag ccagcaagat    1860
caacgagacc atgctgcgcc tgggcatttt tggcttcctg gcctttggct ttgtgctcat    1920
caccttcagc tgccacttct atgacttctt caaccaggct gagtgggagc gtagcttccg    1980
ggactatgtg ctatgccaag ccaacgtgac catcgggctg cctaccaaga gcccattcc    2040 tgactgtgag atcaagaatc ggcccagcct cctggtggag aagatcaatc tatttgccat    2100
gtttggcact ggcattgcca tgagcacctg ggtctggacc aaggccaccc tgctcatctg    2160
gaggcgcacc tggtgcaggt tgactgggca cagtgatgat gagcccaaga gaatcaagaa    2220
gagcaagatg atcgccaagg ccttctctaa gcggcgtgag ctgctgcaga cccgggcca    2280 ggagctctcc ttcagcatgc acactgtctc ccatgatgga cctgttgcgg gtttggcttt    2340
tgacctcaat gaaccctcag ctgacgtctc ctctgcctgg gctcagcatg tcaccaagat    2400
ggtggctcgg agaggagcca tattgccca ggatgtgtcc gttacccctg tggcaactcc    2460
agtgccacca gaagaacaag ccaacatgtg gctggttgag gcagagatct ccccagagtt    2520
agagaagcgt ttgggccgga gaaaaagcg gaggaagagg aagaaggagg tgtgccctt     2580 gaggccagcc cctgagcttc accactctgc ccctgttcct gccaccagtg cagttcctcg    2640
gctgcctcag ctgcctcggc agaagtgcct ggtagctgca aacgcctggg gaacagggga    2700
gtcctgccga cagggagcct ggactctagt ctccaacccc ttctgcccag agcctagtcc    2760
ccatcaagat ccatttctcc ctggtgcctc agccccccgg gtctgggctc agggccgcct    2820
ccaggggctg ggatccattc attcccgcac taacctaatg gaggctgaga tcttggatgc    2880
agactcggac ttctgagcct gcagggcagg tcctaggatg ggaaagacaa atgtacacct    2940
ttctatggct cttcctgaga gcacacctct gggtctcatc tgacagagtc tgtgggccaa    3000
gtgtctgcct agaagagctg tgtatgtctg gctagaagca gccaggccat ggaaacaagt    3060
tgaatacagc gattggtagg cctcatgtca gaatcaggac cctgcacttc aggacccttg    3120
cttctgccca ccaatcagag tctgactggc agtgttagtc tccgacagag cttgtactag    3180
ggcaggaatg gcagagacag ggatgatggt acccagagtg ggctgtggtg gtctgtgagg    3240
taaccaagcc catgtctggc agatgagggc tgtttgccct ttctgtgcc aatgagtgcc     3300 cttttctggc actctcagac caaaagtgtt tattgtgtca tttgtccttt gtctaggaga    3360
ggacaggact ctcttttttcc tcttcctggt agttgtaatg accactccca taagggctat    3420
aactgttctt cacaggtggc cctgctcaaa atacatcctc tcttttcccg ttctatccct    3480
acattcacat ctcagttcca ctaggccaac ctcttcctgg ttagcacctt aaaactgcag    3540
```

| | | | | |
|---|---|---|---|---|
| tgagcacaca | cagacacaca | cacacataca | ctctcacaca | cacagacagg | catgcacaca | 3600 |
| cacacacaca | cacacacaca | cacacacacc | ccttacttct | gagctctgtc | ttaagagact | 3660 |
| actggttcag | ctccaggcct | ctgaaagaca | tgttatttct | tcctcacatc | catccagtgg | 3720 |
| ggaggaccct | ctgacttaag | ggaccacctt | gggaagcttc | tgtagcttca | gccaggcaag | 3780 |
| aaagcttctt | ccaacttctg | tttctggtgg | gagcggggg | actcccactt | tttacaatgt | 3840 |
| ctagtcattt | tcatagtgcc | ccacattcaa | gaaccagaca | acaggatgcc | ttagaagctg | 3900 |
| gctgggtttt | gggtcagggg | ctcagtatga | aagaagaaa | tatgaacagc | aaataaaaca | 3960 |
| ttttgtata | agctcat | | | | | 3977 |

<210> SEQ ID NO 7
<211> LENGTH: 7323
<212> TYPE: DNA
<213> ORGANISM: Mus musculus

<400> SEQUENCE: 7

| | | | | | | |
|---|---|---|---|---|---|---|
| gcggccgcaa | agacctcggg | actcacgcgc | aatgtggcaa | tggaaggcgc | agggtctgag | 60 |
| tccccggcag | cggccacggc | cgcagcaccc | gcagcgcccg | ccgtgtgagc | ggcagcagcg | 120 |
| ggtctgtcac | ccggagccgg | agtccccggc | ggccagcagc | gtcctcgcga | gccgagcgcc | 180 |
| caggcgcgcc | cggagcccgc | ggcggcggcg | gcaacatggc | ctcggctggt | aacgccgccg | 240 |
| gggccctggg | caggcaggcc | ggcggcggga | ggcgcagacg | gaccggggga | ccgcaccgcg | 300 |
| ccgcgccgga | ccgggactat | ctgcaccggc | ccagctactg | cgacgccgcc | ttcgctctgg | 360 |
| agcagatttc | caaggggaag | gctactgccc | ggaaagcgcc | gctgtggctg | agagcgaagt | 420 |
| tcagagact | cttatttaaa | ctgggttgtt | acattcaaaa | gaactgcggc | aagttttgg | 480 |
| ttgtgggtct | cctcatattt | ggggccttcg | ctgtgggatt | aaaggcagct | aatctcgaga | 540 |
| ccaacgtgga | ggagctgtgg | gtggaagttg | gtggacgagt | gagtcgagaa | ttaaattata | 600 |
| cccgtcagaa | gataggagaa | gaggctatgt | ttaatcctca | actcatgata | cagactccaa | 660 |
| agaagaagg | cgctaatgtt | ctgaccacag | aggctctcct | gcaacacctg | gactcagcac | 720 |
| tccaggccag | tcgtgtgcac | gtctacatgt | ataacaggca | atggaagttg | gaacatttgt | 780 |
| gctacaaatc | aggggaactt | atcacggaga | caggttacat | ggatcagata | atagaatacc | 840 |
| tttaccctg | cttaatcatt | acacctttgg | actgcttctg | ggaaggggca | aagctacagt | 900 |
| ccgggacagc | atacctccta | ggtaagcctc | ctttacggtg | gacaaacttt | gacccccttgg | 960 |
| aattcctaga | agagttaaag | aaaataaact | accaagtgga | cagctgggag | gaaatgctga | 1020 |
| ataaagccga | agttggccat | gggtacatgg | accggccttg | cctcaaccca | gccgacccag | 1080 |
| attgccctgc | cacagcccct | aacaaaaatt | caaccaaacc | tcttgatgtg | gcccttgttt | 1140 |
| tgaatggtgg | atgtcaaggt | ttatccagga | agtatatgca | ttggcaggag | gagttgattg | 1200 |
| tgggtggtac | cgtcaagaat | gccactggaa | aacttgtcag | cgctcacgcc | ctgcaaacca | 1260 |
| tgttccagtt | aatgactccc | aagcaaatgt | atgaacactt | caggggctac | gactatgtct | 1320 |
| ctcacatcaa | ctgaatgaa | gacagggcag | ccgccatcct | ggaggcctgg | cagaggactt | 1380 |
| acgtggaggt | ggttcatcaa | agtgtcgccc | caaactccac | tcaaaaggtg | cttcccttca | 1440 |
| caaccacgac | cctggacgac | atcctaaaat | ccttctctga | tgtcagtgtc | atccgagtgg | 1500 |
| ccagcggcta | cctactgatg | cttgcctatg | cctgttaac | catgctgcgc | tgggactgct | 1560 |
| ccaagtccca | gggtgccgtg | gggctggctg | gcgtcctgtt | ggttgcgctg | tcagtggctg | 1620 |
| caggattggg | cctctgctcc | ttgattggca | tttcttttaa | tgctgcgaca | actcaggttt | 1680 |

-continued

```
tgccgtttct tgctcttggt gttggtgtgg atgatgtctt cctcctggcc catgcattca    1740
gtgaaacagg acagaataag aggattccat ttgaggacag gactggggag tgcctcaagc    1800
gcaccggagc cagcgtggcc ctcacctcca tcagcaatgt caccgccttc ttcatggccg    1860
cattgatccc tatccctgcc ctgcgagcgt tctccctcca ggctgctgtg gtggtggtat    1920
tcaattttgc tatggttctg ctcattttc ctgcaattct cagcatggat ttatacagac    1980
gtgaggacag aagattggat attttctgct gtttcacaag ccctgtgtc agcagggtga    2040
ttcaagttga gccacaggcc tacacagagc ctcacagtaa cacccggtac agccccccac    2100
ccccatacac cagccacagc ttcgcccacg aaacccatat cactatgcag tccaccgttc    2160
agctccgcac agagtatgac cctcacacgc acgtgtacta caccaccgcc gagccacgct    2220
ctgagatctc tgtacagcct gttaccgtca cccaggacaa cctcagctgt cagagtcccg    2280
agagcaccag ctctaccagg gacctgctct cccagttctc agactccagc ctccactgcc    2340
tcgagccccc ctgcaccaag tggacactct cttcgtttgc agagaagcac tatgctcctt    2400
tcctcctgaa acccaaagcc aaggttgtgg taatccttct tttcctgggc ttgctggggg    2460
tcagccttta tgggaccacc cgagtgagag acgggctgga cctcacggac attgttcccc    2520
gggaaaccag agaatatgac ttcatagctg cccagttcaa gtacttctct ttctacaaca    2580
tgtatatagt cacccagaaa gcagactacc cgaatatcca gcacctactt tacgaccttc    2640
ataagagttt cagcaatgtg aagtatgtca tgctggagga aacaagcaa cttccccaaa    2700
tgtggctgca ctactttaga gactggcttc aaggacttca ggatgcattt gacagtgact    2760
gggaaactgg gaggatcatg ccaaacaatt ataaaaatgg atcagatgac ggggtcctcg    2820
cttacaaact cctggtgcag actggcagcc gagacaagcc catcgacatt agtcagttga    2880
ctaaacagcg tctggtagac gcagatggca tcattaatcc gagcgctttc tacatctacc    2940
tgaccgcttg ggtcagcaac gaccctgtag cttacgctgc ctcccaggcc aacatccggc    3000
ctcaccggcc ggagtgggtc catgacaaag ccgactacat gccagagacc aggctgagaa    3060
tcccagcagc agagcccatc gagtacgctc agttcccttt ctacctcaac ggcctacgag    3120
acacctcaga ctttgtggaa gccatagaaa aagtgagagt catctgtaac aactatacga    3180
gcctgggact gtccagctac cccaatggct accccttcct gttctgggag caatacatca    3240
gcctgcgcca ctggctgctg ctatccatca gcgtggtgct ggcctgcacg tttctagtgt    3300
gcgcagtctt cctcctgaac ccctggacgg ccgggatcat tgtcatggtc ctggctctga    3360
tgaccgttga gctcttggc atgatgggcc tcattgggat caagctgagt gctgtgcctg    3420
tggtcatcct gattgcatct gttggcatcg agtggagtt caccgtccac gtggctttgg    3480
cctttctgac agccattggg acaagaacc acagggctat gctcgctctg gagcacatgt    3540
ttgctcccgt tctggacggt gctgtgtcca ctctgctggg tgtactgatg cttgcagggt    3600
ccgaatttga tttcattgtc agatacttct ttgccgtcct ggccattctc accgtcttgg    3660
gggttctcaa tggactggtt ctgctgcctg tcctcttatc cttctttgga ccgtgtcctg    3720
aggtgtctcc agccaatggc ctaaaccgac tgcccactcc ttcgcctgag ccgcctccaa    3780
gtgtcgtccg gtttgccgtg cctcctggtc acacgaacaa tgggtctgat tcctccgact    3840
cggagtacag ctctcagacc acggtgtctg gcatcagtga ggagctcagg caatacgaag    3900
cacagcaggg tgccggaggc cctgccacc aagtgattgt ggaagccaca gaaaaccctg    3960
tctttgcccg gtcactgtg gtccatccgg actccagaca tcagcctccc ttgacccctc    4020
ggcaacagcc ccacctggac tctggctcct tgtcccctgg acggcaaggc cagcagcctc    4080
```

```
gaagggatcc ccctagagaa ggcttgcggc cacccccta cagaccgcgc agagacgctt    4140
ttgaaatttc tactgaaggg cattctggcc ctagcaatag ggaccgctca gggccccgtg    4200
gggcccgttc tcacaaccct cggaacccaa cgtccaccgc catgggcagc tctgtgccca    4260
gctactgcca gcccatcacc actgtgacgg cttctgcttc ggtgactgtt gctgtgcatc    4320
ccccgcctgg acctgggcgc aaccccgag ggggccctg tccaggctat gagagctacc    4380
ctgagactga tcacgggta tttgaggatc ctcatgtgcc ttttcatgtc aggtgtgaga    4440
ggagggactc aaaggtggag gtcatagagc tacaggacgt ggaatgtgag gagaggccgt    4500
gggggagcag ctccaactga gggtaattaa aatctgaagc aaagaggcca aagattggaa    4560
agccccgccc ccacctcttt ccagaactgc ttgaagagaa ctgcttggaa ttatgggaag    4620
gcagttcatt gttactgtaa ctgattgtat tattttgtga aatatttcta taaatattta    4680
aaaggtgtac acatgtaata tacatggaaa tgctgtacag tctatttcct ggggcctctc    4740
cactcctgcc ccagagtggg gagaccacag gggcccttc ccctgtgtac attggtctct    4800
gtgccacaac caagcttaac ttagttttaa aaaaaatctc ccagcatatg tcgctgctgc    4860
ttaaatattg tataatttac ttgtataatt ctatgcaaat attgcttatg taataggatt    4920
atttgtaaag gtttctgttt aaaatatttt aaatttgcat atcacaaccc tgtggtagga    4980
tgaattgtta ctgttaactt ttgaacacgc tatgcgtggt aattgtttaa cgagcagaca    5040
tgaagaaaac aggttaatcc cagtggcttc tctaggggta gttgtatatg gttcgcatgg    5100
gtggatgtgt gtgtgcatgt gactttccaa tgtactgtat tgtggtttgt tgttgttgtt    5160
gctgttgttg ttcattttg tgttttttgt tgctttgtat gatcttagct ctggcctagg    5220
tgggctggga aggtccaggt ctttttctgt cgtgatgctg gtggaaaggt gacccaatc    5280 atctgtccta ttctctggga ctattcaaga gaagccagat ttgcttcatg cctgtgtgtg    5340
gcagcttctg aggtcatggg tagccctcca agcacctctg cttgggtttc aaagagaaga    5400
tgttctcaca aacattgtgc tgcctattag ggcctctata tagtcagcag tcagcactag    5460
tggtgaaaga ttggacaatg ttgcctgatg gtgagactca gccgggtcat gagattaccc    5520 tctagggggtg tgtggttgtt cctttctgat gatcacacat acacacagcc tcccaccccc    5580
atactccaga tacaggccca aaaaaaccta tttcactgaa ggtctatatt cgagccttta    5640
caaatgatag tccctcccctt gctatgactg cctggttgga gcaggctagg ctaatcgtgg    5700
ttcagtcaac tgtgtgggga gagtttctaa ggactctttt ccacacggtc ttttcctgtg    5760
tatactttct tctcttcccc actgttagca tccatccagt gtgatgtctg tgaaagcagg    5820
aagatgccac ctcgtaaaag catatagggt aagctctttg aaccaggtgt tgggctttag    5880
agtttgattg tgttctcctt ccccaaggtt tgggttctt tgtctctggt cagcaactag    5940
tagataggga aggaaatgcc cttattcctt gcaagtgaac attgaggact tgtctcagag    6000
gaaggaagcc tagtgctcat ggaagctgtt gtgaggaatg tactctgtct gcatgcagct    6060
tccctgaatc cctcctatcc ttcatggaaa aatttaagga gatgggtccc tagtagtacc    6120
aataatctag tgccctcaga tcctaaaatt tatcccccaa attgtaaggt actaattgga    6180
agccacctgt gactaccgtg tgtgtgtgtg tctgtgtctg tctgtatatc cgtgtgcgcg    6240
tgcgcgccag aagccctggc catccactgc tactgtctta atgcctgtca agccactgtc    6300
tgcctaccca acaccagctc tgctcggata tcttgcaccc tgagttgagg agggagatgt    6360
agagtgcgga agccaccttg gctgtggttc ttgattgtgt ccctcatgcc tgagccttgt    6420
gcatgtggca gaaggaagtt tgtacagcct ctcggcttct gtgcatcatc atgagtccca    6480
```

```
tcagccaagg caggaaggac acagagctgg caggagacta aagtcagaga gtgtgtgtct    6540
ctgtctgtct ctctcatagt tttattttgt ctgtattgtt tgttcatttg gatgttttaa    6600
tttgtaaaag aaaagatctt tgctgatatt tataattttg tatcataaga atgtcctcca    6660
gaatttgtca tgccagttta taacaagaag aaaaaattgc agggatttta tttctattgg    6720
aaacacttat tgcagttatg ttttactttt gaacagaagt tttatttgta tagagtgctt    6780
actaatgtta aatagttcag agtatataac atttacatta aggactcatg gtaggtttta    6840
gtgtaaggag tttaaaggaa ataaatattc aaactgggtc tcgtctgcca atttgggtgg    6900
aaatgagttt gtgtcacttc aattacaaag atgaaagtat gccatataat ttatttatat    6960
gaaaatttat ttttgtagtg tacatagtag tcatcaagtc tttcgacaga agtatatttt    7020
taaagaattt atatgtgatg aaatccataa tgtctggaac tttgctgaga catgggtgtg    7080
aggacacgtt tcgttataaa tgacagcaag ggagagaaga gagtatgttt taacagtgtt    7140
aggagagtac acgtgagcag tgatccatgt gattggaaag tatcggtgtg aacatggtga    7200
cctagtgcgg ttctcagatg aaaatgtaca aaactctcta aatattaatg ttcaaacact    7260
gatagaaatt ctaacatgaa taaagataat ataacttgtt ggtttaaaaa aaaaaaaaaa    7320
aaa                                                                 7323
```

\<210\> SEQ ID NO 8
\<211\> LENGTH: 2727
\<212\> TYPE: DNA
\<213\> ORGANISM: Mus musculus

\<400\> SEQUENCE: 8

```
acaagctctc cagccttgct accatttaaa atcaggctct ttttgtcttt taattgctgt      60
ctcgagaccc aactccgatg tgttccgtta ccagcgaccg gcagcctgcc atcgcagccc     120
cagtctgggt ggggatcgga gacaagtccc ctgcagcagc ggcaggcaag gttatatagg     180
aagagaaaga gccaggcagc gccagaggga acgaacgagc cgagcgagga agggagagcc     240
gagcgcaagg aggagcgcac acgcacacac ccgcgcgtac ccgctcgcgc acagacagcg     300
cggggacagc tcacaagtcc tcaggttccg cggacgagat gctgctgctg ctggccagat     360
gttttctggt gatccttgct tcctcgctgc tggtgtgccc cgggctggcc tgtgggcccg     420
gcagggggtt tggaaagagg cggcacccca aaaagctgac ccctttagcc tacaagcagt     480
ttattcccaa cgtagccgag aagaccctag ggccagcgg cagatatgaa gggaagatca     540
caagaaactc cgaacgattt aaggaactca ccccccaatta caaccccgac atcatattta     600
aggatgagga aaacacggga gcagaccggc tgatgactca gaggtgcaaa gacaagttaa     660
atgccttggc catctctgtg atgaaccagt ggcctggagt gaagctgcga gtgaccgagg     720
gctgggatga ggacggccat cattcagagg agtctctaca ctatgagggt cgagcagtgg     780
acatcaccac gtccgaccgg gaccgcagca agtacggcat gctggctcgc tggctgtgg    840
aagcaggttt cgactgggtc tactatgaat ccaaagctca catccactgt tctgtgaaag     900
cagagaactc cgtggcggcc aaatccggcg gctgtttccc gggatccgcc accgtgcacc     960
tggagcaggg cggcaccaag ctggtgaagg acttacgtcc ggagaccgc gtgctggcg    1020
ctgacgacca gggccggctg ctgtacagcg acttcctcac cttcctggac cgcgacgaag    1080
gcgccaagaa ggtcttctac gtgatcgaga cgctggagcc gcgcgagcgc ctgctgctca    1140
ccgccgcgca cctgctcttc gtggcgccgc acaacgactc ggggcccacg cccgggccaa    1200
gcgcgctctt tgccagccgc gtgcgccccg ggcagcgcgt gtacgtggtg gctgaacgcg    1260
```

| | |
|---|---|
| gcggggaccg ccggctgctg cccgccgcgg tgcacagcgt gacgctgcga gaggaggagg | 1320 |
| cgggcgcgta cgcgccgctc acggcgcacg gcaccattct catcaaccgg gtgctcgcct | 1380 |
| cgtgctacgc tgtcatcgag gagcacagct gggcacaccg ggccttcgcg cctttccgcc | 1440 |
| tggcgcacgc gctgctggcc gcgctggcac ccgcccgcac ggacggcggg ggcggggca | 1500 |
| gcatccctgc agcgcaatct gcaacggaag cgaggggcgc ggagccgact gcgggcatcc | 1560 |
| actggtactc gcagctgctc taccacattg gcacctggct gttggacagc gagaccatgc | 1620 |
| atcccttggg aatggcggtc aagtccagct gaagcccgac gggaccgggc aaggggcggg | 1680 |
| cggggcgggg agcgactgcg aaataaggaa ctgatgggaa agcgcacgga aggagacttt | 1740 |
| taattataag aataattcat aataataata ataatgataa taataataat aataagtagg | 1800 |
| gcagtccaaa gtagactata aggaagcaaa accccgggg agttctgttg ttatgtttag | 1860 |
| tttatatatt tttttgaaat ttttcgttat tgtcttatat gggttgtttt tctcctctcc | 1920 |
| tggctattta tttgtttcgt atgaatagat gttttaaaaa tatgaacgga ccttcaagag | 1980 |
| ccttaactag tttgtgtctt ggataattta ttattgtgtg aactgtactc acagtgaggg | 2040 |
| aaagattatt ttgtgaggcc aagcaacctg ctgaaagtct attttctac atgtcccttg | 2100 |
| tcctgcgttt cagaaggcaa acctccgcat tcctctcctg ctatgctcct gctttccgc | 2160 |
| aagtgtaaac taaaacctgc tccatggggg tccacaaatt atattttat acacagaatt | 2220 |
| gtaaattaga ttttttgagag atcaatacct aactgaatga catttcattt tttgaaagtg | 2280 |
| taaaatatga aaatatatta ttttaattta actatttcc aatgtaatag ccgtcttctg | 2340 |
| tactgccttc ttggtttgta tttgctttgt aaccgccact ttgtcatgtt cttggaaacc | 2400 |
| aagactgtta acgcacacat atacactttt tttttgaca gactggaaga actctgttat | 2460 |
| ttttaacttc aaagaattta ttagaaaata atattttta aaagtgcacc tagcagcgag | 2520 |
| cccacgagga tggagcctgt agtttgtaca gagaaaaaca aggatgtttt tgcattaata | 2580 |
| aactgagaag taactgctgt aaatttacta aaatgtattt ttgaatattt tgtaatagtt | 2640 |
| ttatagaaat aaagcgtgcc acacacaaaa aaaaaaaaaa aaaaaaaaa aaaaaaaaa | 2700 |
| aaaaaaaaaa aaaaaaaaaa aaaaaaa | 2727 |

<210> SEQ ID NO 9
<211> LENGTH: 3686
<212> TYPE: DNA
<213> ORGANISM: Mus musculus

<400> SEQUENCE: 9

| | |
|---|---|
| cacgcatccc gagcaccgcg ccccgacgga ggtctctttg tccgcgcctc tcccacatac | 60 |
| tagaaatctc tcccttcctt gaggttggga tgaagaagca gttgggacgg ccagctggag | 120 |
| gtctgcgtgg tagagggaac tccaggtccc ctcatccttc cctgagacgc catgttcaat | 180 |
| ccaatgactc caccacaagt caatagctat agtgagccat gctgtctccg accctccac | 240 |
| agccaaggag tccccagcat gggaacagaa ggactttctg gtctgccctt ttgccaccaa | 300 |
| gccaacttta tgtcagggtc ccaggggttat ggagcagcca gagagaccag cagctgcact | 360 |
| gaaggatctc tctttcctcc tcctcctcct cctcggagtt cagtcaaatt aacaaagaag | 420 |
| cgggctctct ccatctcgcc cctttctgat gccagcctcg acctgcaaac cgtaatccgg | 480 |
| acctcaccca gctccctggt ggctttcatc aactctcgct gtacatctcc gggcggttcc | 540 |
| tacgccatc tctccattgg taccatgagc ccttctttag gattcccacc tcagatgagt | 600 |
| catcaaaaag gaacttcacc tccctatgga gtccagccct gtgttccaca tgactctact | 660 |

```
cggggttcaa tgatgcttca cccccaggcc cggggaccac gtgcaacctg ccagctgaag      720
tcagagctgg atatgatggt tggcaagtgc ccggaggacc ctttggaagg ggacatgtct      780
agccccaact ccacaggcat acaggatcac ctgttgggga tgctggatgg gcgggaggac      840
ctggagagag aggagaagcc tgagcctgag tctgtgtatg agacagactg ccgctgggat      900
ggttgcagcc aggagttcga ttcccaggag cagctggtgc accacatcaa cagtgagcat      960
atccacgggg agcggaagga attcgtgtgc cattggggag gttgctccag ggagctgagg     1020
cccttcaagg cccaatacat gctggtggtg cacatgcgca gacacacggg cgagaagcca     1080
cacaagtgca cgtttgaagg ctgtcggaag tcctattcac gccttgaaaa cctcaagacg     1140
caccttcggt cgcacacggg tgagaagcct acatgtgtg agcaagaagg ttgcagcaag     1200
gcctttagca atgccagtga ccgcgccaag caccagaatc ggacccactc caatgagaag     1260
ccatacgtgt gcaagctccc cggctgcacc aagcgctaca cagatcccag ctcgctccgc     1320
aaacacgtga agacagtgca tggtccggat gcccacgtga ccaagcggca tcgaggggat     1380
ggccccttgc cacgggctca gcccctctcc acagtggagc caagcgggga aagggaagga     1440
ggatccggca gggaagagag cagactgact gtgcccgaga gtgccatgcc gcagcagagc     1500 cccgagcgc agtcctcttg cagcagcgac cactccccag caggcagtgc ggccaacacg     1560
gacagcggcg tggagatggc cggcaacgcc ggggcagca ctgaggactt gtccagcttg     1620
gatgaaggac cttgtgtctc ggccaccgga ctctccacgc ttcgccgcct ggagaacctt     1680
aggctggatc agctgcatca gctccggccc atagggtctc ggggtctcaa attgccagc     1740 ttaacccacg ctggcgcacc tgtgtctcgc cgtctgggcc cccagtctc cctgaccgc     1800 cgcagcagca gctccagcag catgagctct gcttacacag tcagccgcag gtcctccctg     1860
gcatcccctt tccgccgggg aaccccacca gagaatgggg catcgtcact acctggcctc     1920
acacctgctc agcactacat gctccgtgcc agatatgctt cagccagggg gagtggcacc     1980
ccgcccactg cagctcacag cctggatcgg atggggaggtc tttctgttcc tccttggaga     2040
agccgaaccg agtacccggg atacaaccca aatgcagggg tcactcggag ggccagtgac     2100
ccagcccggg ctgctgacca cccagctcca gccagagtcc agcggttcaa gagcctggga     2160
tgtgtccaca cgcccctag tgtggcaacg ggacggaact tcgatcccca ccacctaccc     2220
tctgtctatt cgccacagcc ccccagcatc accgaaaatg ttgccatgga tactagggg     2280 ctacaggagg agccagaggt tggaacttct gtgatgggca atggtctgaa cccatacatg     2340 gattttttcct ccactgatac tctgggtatat gggggacccg aggggacggc agctgagcct     2400
tatgaagcta ggggtccagg ttccctgcct cttgggcctg gtccaccaac caactatggc     2460
cctggccact gtgcccagca ggtctcctat cctgatccca cccagaaaaa ctggggtgag     2520
ttcccttctc atgctggggt gtaccctagc aataaggctc cgggtgctgc ctatagccag     2580
tgtcctcgac ttgagcatta tggacaagtg caggtaaaac cagaacaagg gtgcccagtg     2640
gggtctgact ccaccggatt ggcaccctgc ctcaatgccc accccagtga agggtcccca     2700
ggcccgcagc ctctgttttc acatcatccc cagctccctc agcccagta tcccagtcg     2760 ggtccctatc ctcagcctcc ccatggttat ctctcaacag aacccaggct tggcctcaat     2820
ttcaacccct cctcctctca ttccacagga cagctcaaag ctcagctggt gtgtaattac     2880
gttcagtcgc agcaggaatt gttgtgggag ggaagaaacc ggggagggct ccccaaccag     2940
gaactcccat accagagccc caagtttctg ggggttccc aagttagtca gagccctgcc     3000 aagacccag cagcagcggc ggcagcatat ggatctggct ttgcacctgc ttcggccaat     3060
```

| | |
|---|---|
| cacaaatcag gctcctatcc tgcccttca ccctgccatg aaactttcac cgtgggagta | 3120 |
| aacaggcctt cccacaggcc agcagcacca ccccgacttc tgccccgct gtccccttgc | 3180 |
| tatgggcccc tcaaggtggg ggataccaac cccagctgtg gccatcctga ggtgggcagg | 3240 |
| ttaggagcag gccctgcctt gtaccctcct cctgaagggc aggtgtgtaa cgctctggac | 3300 |
| tctcttgacc tggacaacac tcagctggac tttgtggcta tcctagatga ggcccagggc | 3360 |
| ctgagccctc ctcttcccca tgagcaaggg gacagctcta aaacaccccc atctccctct | 3420 |
| gggcccccca acatggcagt gggtaacatg agtgtcttgc tggggtctct gcctggagag | 3480 |
| acacaattcc tcaactctag tgcctaaaag ggtaaggaac cccaagcaga tggtatttcc | 3540 |
| taaatggcta catgaggtgc ccagggatgg gaggtttggg ctgggggctg tatttagtct | 3600 |
| atgtatgttc caggaaagaa caaactttaa taatgacaca gtttcctgac aataaaggaa | 3660 |
| tactgagaac aaaaaaaaaa aaaaaa | 3686 |

<210> SEQ ID NO 10
<211> LENGTH: 2596
<212> TYPE: DNA
<213> ORGANISM: Mus musculus

<400> SEQUENCE: 10

| | |
|---|---|
| agtgacagtc atctgtctgg acgcgctggg tggatgcggg gggctcctgg gaactgggtt | 60 |
| ggagccgaac gagcgctagc caggcgtaag cgcgcacaca ctgcagccgc cggaggacaa | 120 |
| ccccctcccg ccgccgctcc ctcagcccac ccggagaccc cagccccgag tcgcctccgg | 180 |
| atccccggca gtctgcggga gagttggagg ttggcgcgac tctgctgctc tccacgggaa | 240 |
| ggaagcactc cccatatta aaaagagcgg agatattaaa agagaggcga acccatgccc | 300 |
| agctgcaccg cgtccaccat gccggggatg atctgcaaga acccagacct cgagtttgac | 360 |
| tcactgcagc cctgcttcta cccggacgaa gatgacttct acttcggcgg tcccgactcg | 420 |
| accccaccgg gggaggacat ctggaagaag tttgagctgc tgcccacgcc ccgttgtcg | 480 |
| cccagccgcg ccttcccaga gcacagcccg gagccttcga attgggctac ggagatgctg | 540 |
| ctgccggagg ccgacctgtg gggcaacccg gccgaggagg atgcgttcgg tctcgggggc | 600 |
| ctgggtggcc tcactcctaa tccggtcatc cttcaggact gcatgtggag cggcttctct | 660 |
| gcccgcgaga agctagagcg cgcagtgaac gaaaaactac agcacggcca cgggcccccg | 720 |
| ggcgtcagct cagcctgctc ggctcccgga gtgggtgcca gcagcccgg gggccgtgcc | 780 |
| cttggtgggt cgtcgagtgc tagccacacc ggggccaccc tgcctaccga cctctcccac | 840 |
| ccggctgccg aatgtgtgga ccccgccgtg gtcttcccct tccggtgaa caagcgagag | 900 |
| tcggcgtcgg tgcccgctgc ccccactagc gccccggcga ccagcgctgc ggtcactagt | 960 |
| gtgtctgttc cagctactgc cccggtggct gctcctgctc gtgcaggcgg ccgtcctgcc | 1020 |
| agcagtgggg aggccaaggc cctcagcacc tccggagagg ataccttgag cgactcagat | 1080 |
| gatgaggatg acgaggagga agatgaagag gaggaaatcg atgtggtcac cgtagagaag | 1140 |
| agacgttcct cctctaacaa caaggcggta accactttca cgatcactgt gcgtcccaag | 1200 |
| acctccgctc tgggcctggg gcgagcacag cctggcgagc tgatcctcaa gcgctgtgtt | 1260 |
| cccatccatc agcagcacaa ctatgctgca ccctcaccct acgtggagag cgaggacgcg | 1320 |
| ccccgcagaa aaagatcaa gagcgaggct ctccacgcc cctcaaaag tgttgttcca | 1380 |
| gcaaaagcga agagcctgag cccccgaaac tcagactcgg aggacagcga gcgccgccgc | 1440 |
| aaccacaaca tcctggagcg tcaacgccgg aacgacctgc gctccagctt cctgacgctc | 1500 |

-continued

| | |
|---|---|
| agggaccatg tgcctgagct ggtgaagaac gagaaggccg ccaaggtggt catcttgaaa | 1560 |
| aaggccaccg agtacgtgca cgccctacag gccaacgagc accagctcct gctggaaaag | 1620 |
| gagaaactgc aggcgaggca gcagcagttg ctaaagaaga tcgaacacgc tcggacttgc | 1680 |
| taaacgtttc ccacacggac agtcactgcc actttgcaca ttttgatttt ttttttttt | 1740 |
| taaacaaaca ttgtgttgac attaagaatg ttggtttact ttcaaattgg tccctgtcg | 1800 |
| agtctggatc tgggtagggg gcaggacacg gggttctgcc atgaccttgg aaaaaaaact | 1860 |
| gacttatggg atgctgggtg gcttgttttc ctcctccata tcacctggtg acagccgtgg | 1920 |
| aagttcggga cactaaggag cttcaggagg ctgtgaagtc accttgttcc ggtccaagat | 1980 |
| tccaaacaga gtcattcctt cttttacaa tggtgcttaa gttccagcaa atgccacaga | 2040 |
| aggggggtt gccatttgat gcccctggga acacttgtgt aaataccatt gatacacccg | 2100 |
| cctttgtat acgtcctggg taatgagagg tggctcttgc ggccagtatt agactggaag | 2160 |
| ttcacccta agtactgtaa gaatacctca atgtttgagg ggcatgtttt gtatacaaat | 2220 |
| atattgttaa tctgttatgt actgtactaa ttcctacacg gcctgtatac tttagtatga | 2280 |
| cgctgataca taactaaatt tgatacttat attttcgtat gaaatgagt tgtggaagtt | 2340 |
| ttgagtagat attactttat cacttttga actaagaaac ttttgtaaag aaattttact | 2400 |
| atatatatat attccttttt ttcctagcct gtttcttcct tgtttactgt atttgttcat | 2460 |
| gtttggtgca tagaactggg taaaatggca aagttctgtg tttaatttct tcaaaatgta | 2520 |
| tatatttagt gctgcacctt agagcacttt gaaatacctc atgtttatga aaataaatag | 2580 |
| caattaaatg atgcaa | 2596 |

<210> SEQ ID NO 11
<211> LENGTH: 2364
<212> TYPE: DNA
<213> ORGANISM: Homo sapiens

<400> SEQUENCE: 11

| | |
|---|---|
| atggccgctg cccgcccagc gcggggggccg gagctcccgc tcctggggct gctgctgctg | 60 |
| ctgctgctgg ggacccgggg ccgggggggcg gcctcgagcg ggaacgcgac cgggcctggg | 120 |
| cctcggagcg cgggcgggag cgcgaggagg agcgcggcgg tgactggccc tccgccgccg | 180 |
| ctgagccact gcgccgggc tgccccctgc gagccgctgc gctacaacgt gtgcctgggc | 240 |
| tcggtgctgc cctacggggc cacctccaca ctgctggccg gagactcgga ctcccaggag | 300 |
| gaagcgcacg gcaagctcgt gctctggtcg ggctcccgga tgccccccg ctgctgggca | 360 |
| gtgatccagc ccctgctgtg tgccgtatac atgcccaagt gtgagaatga ccgggtggag | 420 |
| ctgcccagcc gtaccctctg ccaggccacc cgaggccct gtgccatcgt ggagagggag | 480 |
| cggggctggc ctgacttcct gcgctgcact cctgaccgct tccctgaagg ctgcacgaat | 540 |
| gaggtgcaga acatcaagtt caacagttca ggccagtgcg aagtgccctt ggttcggaca | 600 |
| gacaaccca agagctggta cgaggacgtg gagggctgcg gcatccagtg ccagaacccg | 660 |
| ctcttcacag aggctgagca ccaggacatg cacagctaca tcgcggcctt cggggccgtc | 720 |
| acgggcctct gcacgctctt caccctggcc acattcgtgg ctgactggcg gaactcgaat | 780 |
| cgctacccctg ctgttattct cttctacgtc aatgcgtgct tctttgtggg cagcattggc | 840 |
| tggctggccc agttcatgga tggtgcccgc cgagagatcg tctgccgtgc agatggcacc | 900 |
| atgaggcttg gggagcccac ctccaatgag actctgtcct cgtcatcat ctttgtcatc | 960 |
| gtgtactacg ccctgatggc tggtgtggtt tggtttgtgg tcctcaccta tgcctggcac | 1020 |

```
acttccttca aagccctggg caccacctac cagcctctct cgggcaagac ctcctacttc    1080
cacctgctca cctggtcact ccctttgtc  ctcactgtgg caatccttgc tgtggcgcag    1140
gtggatgggg actctgtgag tggcatttgt tttgtgggct acaagaacta ccgataccgt    1200
gcgggcttcg tgctggcccc aatcggcctg gtgctcatcg tgggaggcta cttcctcatc    1260
cgaggagtca tgactctgtt ctccatcaag agcaaccacc ccgggctgct gagtgagaag    1320
gctgccagca agatcaacga gaccatgctg cgcctgggca ttttttggctt cctggccttt    1380 ggctttgtgc tcattacctt cagctgccac ttctacgact tcttcaacca ggctgagtgg    1440
gagcgcagct tccgggacta tgtgctatgt caggccaatg tgaccatcgg gctgcccacc    1500
aagcagccca tccctgactg tgagatcaag aatcgcccga gccttctggt ggagaagatc    1560
aacctgtttg ccatgtttgg aactggcatc gccatgagca cctgggtctg gaccaaggcc    1620
acgctgctca tctggaggcg tacctggtgc aggttgactg ggcagagtga cgatgagcca    1680
aagcggatca agaagagcaa gatgattgcc aaggccttct ctaagcggca cgagctcctg    1740
cagaacccag gccaggagct gtccttcagc atgcacactg tgtcccacga cgggcccgtg    1800
gcgggcttgg cctttgacct caatgagccc tcagctgatg tctcctctgc ctgggcccag    1860
catgtcacca agatggtggc tcggagagga gccatactgc cccaggatat ttctgtcacc    1920
cctgtggcaa ctccagtgcc cccagaggaa caagccaacc tgtggctggt tgaggcagag    1980
atctccccag agctgcagaa cgcctgggcc cggaagaaga agaggaggaa gaggaagaag    2040
gaggtgtgcc cgctggcgcc gccccctgag cttcacccc  ctgcccctgc cccagtacc    2100 attcctcgac tgcctcagct gccccggcag aaatgcctgg tggctgcagg tgcctgggga    2160
gctggggact cttgccgaca gggagcgtgg accctggtct ccaacccatt ctgcccagag    2220
cccagtcccc ctcaggatcc atttctgccc agtgcaccgg ccccgtggc atgggctcat    2280 ggccgccgac agggcctggg gcctattcac tcccgcacca acctgatgga cacagaactc    2340
atggatgcag actcggactt ctga                                          2364
```

<210> SEQ ID NO 12
<211> LENGTH: 787
<212> TYPE: PRT
<213> ORGANISM: Homo sapiens

<400> SEQUENCE: 12

```
Met Ala Ala Ala Arg Pro Ala Arg Gly Pro Glu Leu Pro Leu Leu Gly
1               5                   10                  15

Leu Leu Leu Leu Leu Leu Leu Gly Asp Pro Gly Arg Gly Ala Ala Ser
            20                  25                  30

Ser Gly Asn Ala Thr Gly Pro Gly Pro Arg Ser Ala Gly Ser Ala
        35                  40                  45

Arg Arg Ser Ala Ala Val Thr Gly Pro Pro Pro Leu Ser His Cys
    50                  55                  60

Gly Arg Ala Ala Pro Cys Glu Pro Leu Arg Tyr Asn Val Cys Leu Gly
65                  70                  75                  80

Ser Val Leu Pro Tyr Gly Ala Thr Ser Thr Leu Leu Ala Gly Asp Ser
                85                  90                  95

Asp Ser Gln Glu Glu Ala His Gly Lys Leu Val Leu Trp Ser Gly Leu
            100                 105                 110

Arg Asn Ala Pro Arg Cys Trp Ala Val Ile Gln Pro Leu Leu Cys Ala
        115                 120                 125
```

```
Val Tyr Met Pro Lys Cys Glu Asn Asp Arg Val Glu Leu Pro Ser Arg
130                 135                 140

Thr Leu Cys Gln Ala Thr Arg Gly Pro Cys Ala Ile Val Glu Arg Glu
145                 150                 155                 160

Arg Gly Trp Pro Asp Phe Leu Arg Cys Thr Pro Asp Arg Phe Pro Glu
                165                 170                 175

Gly Cys Thr Asn Glu Val Gln Asn Ile Lys Phe Asn Ser Ser Gly Gln
                180                 185                 190

Cys Glu Val Pro Leu Val Arg Thr Asp Asn Pro Lys Ser Trp Tyr Glu
                195                 200                 205

Asp Val Glu Gly Cys Gly Ile Gln Cys Gln Asn Pro Leu Phe Thr Glu
210                 215                 220

Ala Glu His Gln Asp Met His Ser Tyr Ile Ala Ala Phe Gly Ala Val
225                 230                 235                 240

Thr Gly Leu Cys Thr Leu Phe Thr Leu Ala Thr Phe Val Ala Asp Trp
                245                 250                 255

Arg Asn Ser Asn Arg Tyr Pro Ala Val Ile Leu Phe Tyr Val Asn Ala
                260                 265                 270

Cys Phe Phe Val Gly Ser Ile Gly Trp Leu Ala Gln Phe Met Asp Gly
                275                 280                 285

Ala Arg Arg Glu Ile Val Cys Arg Ala Asp Gly Thr Met Arg Leu Gly
290                 295                 300

Glu Pro Thr Ser Asn Glu Thr Leu Ser Cys Val Ile Ile Phe Val Ile
305                 310                 315                 320

Val Tyr Tyr Ala Leu Met Ala Gly Val Val Trp Phe Val Val Leu Thr
                325                 330                 335

Tyr Ala Trp His Thr Ser Phe Lys Ala Leu Gly Thr Thr Tyr Gln Pro
                340                 345                 350

Leu Ser Gly Lys Thr Ser Tyr Phe His Leu Leu Thr Trp Ser Leu Pro
                355                 360                 365

Phe Val Leu Thr Val Ala Ile Leu Ala Val Ala Gln Val Asp Gly Asp
370                 375                 380

Ser Val Ser Gly Ile Cys Phe Val Gly Tyr Lys Asn Tyr Arg Tyr Arg
385                 390                 395                 400

Ala Gly Phe Val Leu Ala Pro Ile Gly Leu Val Leu Ile Val Gly Gly
                405                 410                 415

Tyr Phe Leu Ile Arg Gly Val Met Thr Leu Phe Ser Ile Lys Ser Asn
                420                 425                 430

His Pro Gly Leu Leu Ser Glu Lys Ala Ala Ser Lys Ile Asn Glu Thr
                435                 440                 445

Met Leu Arg Leu Gly Ile Phe Gly Phe Leu Ala Phe Gly Phe Val Leu
450                 455                 460

Ile Thr Phe Ser Cys His Phe Tyr Asp Phe Phe Asn Gln Ala Glu Trp
465                 470                 475                 480

Glu Arg Ser Phe Arg Asp Tyr Val Leu Cys Gln Ala Asn Val Thr Ile
                485                 490                 495

Gly Leu Pro Thr Lys Gln Pro Ile Pro Asp Cys Glu Ile Lys Asn Arg
                500                 505                 510

Pro Ser Leu Leu Val Glu Lys Ile Asn Leu Phe Ala Met Phe Gly Thr
                515                 520                 525

Gly Ile Ala Met Ser Thr Trp Val Trp Thr Lys Ala Thr Leu Leu Ile
530                 535                 540
```

```
Trp Arg Arg Thr Trp Cys Arg Leu Thr Gly Gln Ser Asp Asp Glu Pro
545                 550                 555                 560

Lys Arg Ile Lys Lys Ser Lys Met Ile Ala Lys Ala Phe Ser Lys Arg
                565                 570                 575

His Glu Leu Leu Gln Asn Pro Gly Gln Glu Leu Ser Phe Ser Met His
            580                 585                 590

Thr Val Ser His Asp Gly Pro Val Ala Gly Leu Ala Phe Asp Leu Asn
        595                 600                 605

Glu Pro Ser Ala Asp Val Ser Ser Ala Trp Ala Gln His Val Thr Lys
    610                 615                 620

Met Val Ala Arg Arg Gly Ala Ile Leu Pro Gln Asp Ile Ser Val Thr
625                 630                 635                 640

Pro Val Ala Thr Pro Val Pro Pro Glu Gln Ala Asn Leu Trp Leu
                645                 650                 655

Val Glu Ala Glu Ile Ser Pro Glu Leu Gln Lys Arg Leu Gly Arg Lys
                660                 665                 670

Lys Lys Arg Arg Lys Arg Lys Lys Glu Val Cys Pro Leu Ala Pro Pro
                675                 680                 685

Pro Glu Leu His Pro Pro Ala Pro Ala Pro Ser Thr Ile Pro Arg Leu
    690                 695                 700

Pro Gln Leu Pro Arg Gln Lys Cys Leu Val Ala Ala Gly Ala Trp Gly
705                 710                 715                 720

Ala Gly Asp Ser Cys Arg Gln Gly Ala Trp Thr Leu Val Ser Asn Pro
                725                 730                 735

Phe Cys Pro Glu Pro Ser Pro Gln Asp Pro Phe Leu Pro Ser Ala
                740                 745                 750

Pro Ala Pro Val Ala Trp Ala His Gly Arg Arg Gln Gly Leu Gly Pro
            755                 760                 765

Ile His Ser Arg Thr Asn Leu Met Asp Thr Glu Leu Met Asp Ala Asp
    770                 775                 780

Ser Asp Phe
785

<210> SEQ ID NO 13
<211> LENGTH: 1106
<212> TYPE: PRT
<213> ORGANISM: Homo sapiens

<400> SEQUENCE: 13

Met Phe Asn Ser Met Thr Pro Pro Ile Ser Ser Tyr Gly Glu Pro
1               5                   10                  15

Cys Cys Leu Arg Pro Leu Pro Ser Gln Gly Ala Pro Ser Val Gly Thr
                20                  25                  30

Glu Gly Leu Ser Gly Pro Pro Phe Cys His Gln Ala Asn Leu Met Ser
            35                  40                  45

Gly Pro His Ser Tyr Gly Pro Ala Arg Glu Thr Asn Ser Cys Thr Glu
        50                  55                  60

Gly Pro Leu Phe Ser Ser Pro Arg Ser Ala Val Lys Leu Thr Lys Lys
65                  70                  75                  80

Arg Ala Leu Ser Ile Ser Pro Leu Ser Asp Ala Ser Leu Asp Leu Gln
                85                  90                  95

Thr Val Ile Arg Thr Ser Pro Ser Ser Leu Val Ala Phe Ile Asn Ser
                100                 105                 110

Arg Cys Thr Ser Pro Gly Gly Ser Tyr Gly His Leu Ser Ile Gly Thr
            115                 120                 125
```

-continued

```
Met Ser Pro Ser Leu Gly Phe Pro Ala Gln Met Asn His Gln Lys Gly
    130                 135                 140
Pro Ser Pro Ser Phe Gly Val Gln Pro Cys Gly Pro His Asp Ser Ala
145                 150                 155                 160
Arg Gly Gly Met Ile Pro His Pro Gln Ser Arg Gly Pro Phe Pro Thr
                165                 170                 175
Cys Gln Leu Lys Ser Glu Leu Asp Met Leu Val Gly Lys Cys Arg Glu
            180                 185                 190
Glu Pro Leu Glu Gly Asp Met Ser Ser Pro Asn Ser Thr Gly Ile Gln
        195                 200                 205
Asp Pro Leu Leu Gly Met Leu Asp Gly Arg Glu Asp Leu Glu Arg Glu
210                 215                 220
Glu Lys Arg Glu Pro Glu Ser Val Tyr Glu Thr Asp Cys Arg Trp Asp
225                 230                 235                 240
Gly Cys Ser Gln Glu Phe Asp Ser Gln Glu Gln Leu Val His His Ile
                245                 250                 255
Asn Ser Glu His Ile His Gly Glu Arg Lys Glu Phe Val Cys His Trp
            260                 265                 270
Gly Gly Cys Ser Arg Glu Leu Arg Pro Phe Lys Ala Gln Tyr Met Leu
        275                 280                 285
Val Val His Met Arg Arg His Thr Gly Glu Lys Pro His Lys Cys Thr
290                 295                 300
Phe Glu Gly Cys Arg Lys Ser Tyr Ser Arg Leu Glu Asn Leu Lys Thr
305                 310                 315                 320
His Leu Arg Ser His Thr Gly Glu Lys Pro Tyr Met Cys Glu His Glu
                325                 330                 335
Gly Cys Ser Lys Ala Phe Ser Asn Ala Ser Asp Arg Ala Lys His Gln
            340                 345                 350
Asn Arg Thr His Ser Asn Glu Lys Pro Tyr Val Cys Lys Leu Pro Gly
        355                 360                 365
Cys Thr Lys Arg Tyr Thr Asp Pro Ser Ser Leu Arg Lys His Val Lys
370                 375                 380
Thr Val His Gly Pro Asp Ala His Val Thr Lys Arg His Arg Gly Asp
385                 390                 395                 400
Gly Pro Leu Pro Arg Ala Pro Ser Ile Ser Thr Val Glu Pro Lys Arg
                405                 410                 415
Glu Arg Glu Gly Gly Pro Ile Arg Glu Glu Ser Arg Leu Thr Val Pro
            420                 425                 430
Glu Gly Ala Met Lys Pro Gln Pro Ser Pro Gly Ala Gln Ser Ser Cys
        435                 440                 445
Ser Ser Asp His Ser Pro Ala Gly Ser Ala Ala Asn Thr Asp Ser Gly
450                 455                 460
Val Glu Met Thr Gly Asn Ala Gly Gly Ser Thr Glu Asp Leu Ser Ser
465                 470                 475                 480
Leu Asp Glu Gly Pro Cys Ile Ala Gly Thr Gly Leu Ser Thr Leu Arg
                485                 490                 495
Arg Leu Glu Asn Leu Arg Leu Asp Gln Leu His Gln Leu Arg Pro Ile
            500                 505                 510
Gly Thr Arg Gly Leu Lys Leu Pro Ser Leu Ser His Thr Gly Thr Thr
        515                 520                 525
Val Ser Arg Arg Val Gly Pro Pro Val Ser Leu Glu Arg Ser Ser
530                 535                 540
```

```
Ser Ser Ser Ile Ser Ser Ala Tyr Thr Val Ser Arg Arg Ser Ser
545                 550                 555                 560

Leu Ala Ser Pro Phe Pro Pro Gly Ser Pro Pro Glu Asn Gly Ala Ser
                565                 570                 575

Ser Leu Pro Gly Leu Met Pro Ala Gln His Tyr Leu Leu Arg Ala Arg
            580                 585                 590

Tyr Ala Ser Ala Arg Gly Gly Thr Ser Pro Thr Ala Ala Ser Ser
        595                 600                 605

Leu Asp Arg Ile Gly Gly Leu Pro Met Pro Pro Trp Arg Ser Arg Ala
610                 615                 620

Glu Tyr Pro Gly Tyr Asn Pro Asn Ala Gly Val Thr Arg Arg Ala Ser
625                 630                 635                 640

Asp Pro Ala Gln Ala Ala Asp Arg Pro Ala Pro Ala Arg Val Gln Arg
                645                 650                 655

Phe Lys Ser Leu Gly Cys Val His Thr Pro Thr Val Ala Gly Gly
                660                 665                 670

Gly Gln Asn Phe Asp Pro Tyr Leu Pro Thr Ser Val Tyr Ser Pro Gln
            675                 680                 685

Pro Pro Ser Ile Thr Glu Asn Ala Ala Met Asp Ala Arg Gly Leu Gln
        690                 695                 700

Glu Glu Pro Glu Val Gly Thr Ser Met Val Gly Ser Gly Leu Asn Pro
705                 710                 715                 720

Tyr Met Asp Phe Pro Pro Thr Asp Thr Leu Gly Tyr Gly Gly Pro Glu
                725                 730                 735

Gly Ala Ala Ala Glu Pro Tyr Gly Ala Arg Gly Pro Gly Ser Leu Pro
                740                 745                 750

Leu Gly Pro Gly Pro Pro Thr Asn Tyr Gly Pro Asn Pro Cys Pro Gln
            755                 760                 765

Gln Ala Ser Tyr Pro Asp Pro Thr Gln Glu Thr Trp Gly Glu Phe Pro
    770                 775                 780

Ser His Ser Gly Leu Tyr Pro Gly Pro Lys Ala Leu Gly Gly Thr Tyr
785                 790                 795                 800

Ser Gln Cys Pro Arg Leu Glu His Tyr Gly Gln Val Gln Val Lys Pro
                805                 810                 815

Glu Gln Gly Cys Pro Val Gly Ser Asp Ser Thr Gly Leu Ala Pro Cys
                820                 825                 830

Leu Asn Ala His Pro Ser Glu Gly Pro Pro His Pro Gln Pro Leu Phe
            835                 840                 845

Ser His Tyr Pro Gln Pro Ser Pro Pro Gln Tyr Leu Gln Ser Gly Pro
850                 855                 860

Tyr Thr Gln Pro Pro Pro Asp Tyr Leu Pro Ser Glu Pro Arg Pro Cys
865                 870                 875                 880

Leu Asp Phe Asp Ser Pro Thr His Ser Thr Gly Gln Leu Lys Ala Gln
                885                 890                 895

Leu Val Cys Asn Tyr Val Gln Ser Gln Gln Glu Leu Leu Trp Glu Gly
            900                 905                 910

Gly Gly Arg Glu Asp Ala Pro Ala Gln Glu Pro Ser Tyr Gln Ser Pro
        915                 920                 925

Lys Phe Leu Gly Asp Ser Gln Val Ser Pro Ser Arg Ala Lys Ala Pro
    930                 935                 940

Val Asn Thr Tyr Gly Pro Gly Phe Gly Pro Asn Leu Pro Asn His Lys
945                 950                 955                 960
```

```
Ser Gly Ser Tyr Pro Thr Pro Ser Pro Cys His Glu Asn Phe Val Val
            965                 970                 975

Gly Ala Asn Arg Ala Ser His Arg Ala Ala Pro Pro Arg Leu Leu
        980                 985                 990

Pro Pro Leu Pro Thr Cys Tyr Gly Pro Leu Lys Val Gly Gly Thr Asn
            995                1000                1005

Pro Ser Cys Gly His Pro Glu Val Gly Arg Leu Gly Gly Gly Pro Ala
        1010                1015                1020

Leu Tyr Pro Pro Pro Glu Gly Gln Val Cys Asn Pro Leu Asp Ser Leu
1025                1030                1035                1040

Asp Leu Asp Asn Thr Gln Leu Asp Phe Val Ala Ile Leu Asp Glu Pro
            1045                1050                1055

Gln Gly Leu Ser Pro Pro Ser His Asp Gln Arg Gly Ser Ser Gly
            1060                1065                1070

His Thr Pro Pro Pro Ser Gly Pro Asn Met Ala Val Gly Asn Met
            1075                1080                1085

Ser Val Leu Leu Arg Ser Leu Pro Gly Glu Thr Gln Phe Leu Asn Ser
        1090                1095                1100

Ser Ala
1105

<210> SEQ ID NO 14
<211> LENGTH: 1586
<212> TYPE: PRT
<213> ORGANISM: Homo sapiens

<400> SEQUENCE: 14

Met Glu Thr Ser Ala Ser Ala Thr Ala Ser Glu Lys Gln Glu Ala Lys
1               5                   10                  15

Ser Gly Ile Leu Glu Ala Ala Gly Phe Pro Asp Pro Gly Lys Lys Ala
            20                  25                  30

Ser Pro Leu Val Val Ala Ala Ala Ala Ala Val Ala Ala Gln
        35                  40                  45

Gly Val Pro Gln His Leu Leu Pro Pro Phe His Ala Pro Leu Pro Ile
    50                  55                  60

Asp Met Arg His Gln Glu Gly Arg Tyr His Tyr Glu Pro His Ser Val
65              70                  75                  80

His Gly Val His Gly Pro Pro Ala Leu Ser Gly Ser Pro Val Ile Ser
            85                  90                  95

Asp Ile Ser Leu Ile Arg Leu Ser Pro His Pro Ala Gly Pro Gly Glu
            100                 105                 110

Ser Pro Phe Asn Ala Pro His Pro Tyr Val Asn Pro His Met Glu His
        115                 120                 125

Tyr Leu Arg Ser Val His Ser Ser Pro Thr Leu Ser Met Ile Ser Ala
    130                 135                 140

Ala Arg Gly Leu Ser Pro Ala Asp Val Ala Gln Glu His Leu Lys Glu
145                 150                 155                 160

Arg Gly Leu Phe Gly Leu Pro Ala Pro Gly Thr Thr Pro Ser Asp Tyr
                165                 170                 175

Tyr His Gln Met Thr Leu Val Ala Gly His Pro Ala Pro Tyr Gly Asp
            180                 185                 190

Leu Leu Met Gln Ser Gly Gly Ala Ala Ser Ala Pro His Leu His Asp
        195                 200                 205

Tyr Leu Asn Pro Val Asp Val Ser Arg Phe Ser Ser Pro Arg Val Thr
    210                 215                 220
```

```
Pro Arg Leu Ser Arg Lys Arg Ala Leu Ser Ile Ser Pro Leu Ser Asp
225                 230                 235                 240

Ala Ser Leu Asp Leu Gln Arg Met Ile Arg Thr Ser Pro Asn Ser Leu
            245                 250                 255

Val Ala Tyr Ile Asn Asn Ser Arg Ser Ser Ala Ala Ser Gly Ser
        260                 265                 270

Tyr Gly His Leu Ser Ala Gly Ala Leu Ser Pro Ala Phe Thr Phe Pro
        275                 280                 285

His Pro Ile Asn Pro Val Ala Tyr Gln Gln Ile Leu Ser Gln Gln Arg
    290                 295                 300

Gly Leu Gly Ser Ala Phe Gly His Thr Pro Pro Leu Ile Gln Pro Ser
305                 310                 315                 320

Pro Thr Phe Leu Ala Gln Gln Pro Met Ala Leu Thr Ser Ile Asn Ala
            325                 330                 335

Thr Pro Thr Gln Leu Ser Ser Ser Asn Cys Leu Ser Asp Thr Asn
            340                 345                 350       Asn

Gln Asn Lys Gln Ser Ser Glu Ser Ala Val Ser Ser Thr Val Asn Pro
            355                 360                 365

Val Ala Ile His Lys Arg Ser Lys Val Lys Thr Glu Pro Glu Gly Leu
        370                 375                 380

Arg Pro Ala Ser Pro Leu Ala Leu Thr Gln Gly Gln Val Ser Gly His
385                 390                 395                 400

Gly Ser Cys Gly Cys Ala Leu Pro Leu Ser Gln Glu Gln Leu Ala Asp
                405                 410                 415

Leu Lys Glu Asp Leu Asp Arg Asp Asp Cys Lys Gln Glu Ala Glu Val
            420                 425                 430

Val Ile Tyr Glu Thr Asn Cys His Trp Glu Asp Cys Thr Lys Glu Tyr
        435                 440                 445

Asp Thr Gln Glu Gln Leu Val His His Ile Asn Asn Glu His Ile His
    450                 455                 460

Gly Glu Lys Lys Glu Phe Val Cys Arg Trp Gln Ala Cys Thr Arg Glu
465                 470                 475                 480

Gln Lys Pro Phe Lys Ala Gln Tyr Met Leu Val Val His Met Arg Arg
                485                 490                 495

His Thr Gly Glu Lys Pro His Lys Cys Thr Phe Glu Gly Cys Ser Lys
            500                 505                 510

Ala Tyr Ser Arg Leu Glu Asn Leu Lys Thr His Leu Arg Ser His Thr
        515                 520                 525

Gly Glu Lys Pro Tyr Val Cys Glu His Glu Gly Cys Asn Lys Ala Phe
530                 535                 540

Ser Asn Ala Ser Asp Arg Ala Lys His Gln Asn Arg Thr His Ser Asn
545                 550                 555                 560

Glu Lys Pro Tyr Ile Cys Lys Ile Pro Gly Cys Thr Lys Arg Tyr Thr
                565                 570                 575

Asp Pro Ser Ser Leu Arg Lys His Val Lys Thr Val His Gly Pro Asp
            580                 585                 590

Ala His Val Thr Lys Lys Gln Arg Asn Asp Val His Leu Arg Thr Pro
        595                 600                 605

Leu Leu Lys Glu Asn Gly Asp Ser Glu Ala Gly Thr Glu Pro Gly Gly
    610                 615                 620

Pro Glu Ser Thr Glu Ala Ser Ser Thr Ser Gln Ala Val Glu Asp Cys
625                 630                 635                 640
```

```
Leu His Val Arg Ala Ile Lys Thr Glu Ser Ser Gly Leu Cys Gln Ser
                645                 650                 655

Ser Pro Gly Ala Gln Ser Ser Cys Ser Ser Glu Pro Ser Pro Leu Gly
            660                 665                 670

Ser Ala Pro Asn Asn Asp Ser Gly Val Glu Met Pro Gly Thr Gly Pro
            675                 680                 685

Gly Ser Leu Gly Asp Leu Thr Ala Leu Asp Asp Thr Pro Pro Gly Ala
            690                 695                 700

Asp Thr Ser Ala Leu Ala Ala Pro Ser Ala Gly Leu Gln Leu Arg
705                 710                 715                 720

Lys His Met Thr Thr Met His Arg Phe Glu Gln Leu Lys Lys Glu Lys
                725                 730                 735

Leu Lys Ser Leu Lys Asp Ser Cys Ser Trp Ala Gly Pro Thr Pro His
            740                 745                 750

Thr Arg Asn Thr Lys Leu Pro Pro Leu Pro Gly Ser Gly Ser Ile Leu
            755                 760                 765

Glu Asn Phe Ser Gly Ser Gly Gly Gly Pro Ala Gly Leu Leu Pro
770                 775                 780

Asn Pro Arg Leu Ser Glu Leu Ser Ala Ser Glu Val Thr Met Leu Ser
785                 790                 795                 800

Gln Leu Gln Glu Arg Arg Asp Ser Ser Thr Ser Thr Val Ser Ser Ala
                805                 810                 815

Tyr Thr Val Ser Arg Arg Ser Ser Gly Ile Ser Pro Tyr Phe Ser Ser
                820                 825                 830

Arg Arg Ser Ser Glu Ala Ser Pro Leu Gly Ala Gly Arg Pro His Asn
                835                 840                 845

Ala Ser Ser Ala Asp Ser Tyr Asp Pro Ile Ser Thr Asp Ala Ser Arg
            850                 855                 860

Arg Ser Ser Glu Ala Ser Gln Cys Ser Gly Gly Ser Gly Leu Leu Asn
865                 870                 875                 880

Leu Thr Pro Ala Gln Gln Tyr Ser Leu Arg Ala Lys Tyr Ala Ala Ala
                885                 890                 895

Thr Gly Gly Pro Pro Pro Thr Pro Leu Pro Gly Leu Glu Arg Met Ser
            900                 905                 910

Leu Arg Thr Arg Leu Ala Leu Leu Asp Ala Pro Glu Arg Thr Leu Pro
            915                 920                 925

Ala Gly Cys Pro Arg Pro Leu Gly Pro Arg Arg Gly Ser Asp Gly Pro
            930                 935                 940

Thr Tyr Gly His Gly His Ala Gly Ala Ala Pro Ala Phe Pro His Glu
945                 950                 955                 960

Ala Pro Gly Gly Gly Ala Arg Arg Ala Ser Asp Pro Val Arg Arg Pro
                965                 970                 975

Asp Ala Leu Ser Leu Pro Arg Val Gln Arg Phe His Ser Thr His Asn
                980                 985                 990

Val Asn Pro Gly Pro Leu Pro Pro Cys Ala Asp Arg Arg Gly Leu Arg
995                 1000                1005

Leu Gln Ser His Pro Ser Thr Asp Gly Gly Leu Ala Arg Gly Ala Tyr
            1010                1015                1020

Ser Pro Arg Pro Pro Ser Ile Ser Glu Asn Val Ala Met Glu Ala Val
1025                1030                1035                1040

Ala Ala Gly Val Asp Gly Ala Gly Pro Glu Ala Asp Leu Gly Leu Pro
                1045                1050                1055
```

-continued

```
Glu Asp Asp Leu Val Leu Pro Asp Asp Val Val Gln Tyr Ile Lys Ala
            1060                1065                1070

His Ala Ser Gly Ala Leu Asp Glu Gly Thr Gly Gln Val Tyr Pro Thr
        1075                1080                1085

Glu Ser Thr Gly Phe Ser Asp Asn Pro Arg Leu Pro Ser Pro Gly Leu
    1090                1095                1100

His Gly Gln Arg Arg Met Val Ala Ala Asp Ser Asn Val Gly Pro Ser
1105                1110                1115                1120

Ala Pro Met Leu Gly Gly Cys Gln Leu Gly Phe Gly Ala Pro Ser Ser
                1125                1130                1135

Leu Asn Lys Asn Asn Met Pro Val Gln Trp Asn Glu Val Ser Ser Gly
            1140                1145                1150

Thr Val Asp Ala Leu Ala Ser Gln Val Lys Pro Pro Pro Phe Pro Gln
            1155                1160                1165

Gly Asn Leu Ala Val Val Gln Gln Lys Pro Ala Phe Gly Gln Tyr Pro
        1170                1175                1180

Gly Tyr Ser Pro Gln Gly Leu Gln Ala Ser Pro Gly Gly Leu Asp Ser
1185                1190                1195                1200

Thr Gln Pro His Leu Gln Pro Arg Ser Gly Ala Pro Ser Gln Gly Ile
            1205                1210                1215

Pro Arg Val Asn Tyr Met Gln Gln Leu Arg Gln Pro Val Ala Gly Ser
            1220                1225                1230

Gln Cys Pro Gly Met Thr Thr Thr Met Ser Pro His Ala Cys Tyr Gly
            1235                1240                1245

Gln Val His Pro Gln Leu Ser Pro Ser Thr Ile Ser Gly Ala Leu Asn
        1250                1255                1260

Gln Phe Pro Gln Ser Cys Ser Asn Met Pro Ala Lys Pro Gly His Leu
1265                1270                1275                1280

Gly His Pro Gln Gln Thr Glu Val Ala Pro Asp Pro Thr Thr Met Gly
            1285                1290                1295

Asn Arg His Arg Glu Leu Gly Val Pro Asp Ser Ala Leu Ala Gly Val
            1300                1305                1310

Pro Pro Pro His Pro Val Gln Ser Tyr Pro Gln Gln Ser His His Leu
            1315                1320                1325

Ala Ala Ser Met Ser Gln Glu Gly Tyr His Gln Val Pro Ser Leu Leu
            1330                1335                1340

Pro Ala Arg Gln Pro Gly Phe Met Glu Pro Gln Thr Gly Pro Met Gly
1345                1350                1355                1360

Val Ala Thr Ala Gly Phe Gly Leu Val Gln Pro Arg Pro Pro Leu Glu
            1365                1370                1375

Pro Ser Pro Thr Gly Arg His Arg Gly Val Arg Ala Val Gln Gln Gln
            1380                1385                1390

Leu Ala Tyr Ala Arg Ala Thr Gly His Ala Met Ala Met Pro Ser
            1395                1400                1405

Ser Gln Glu Thr Ala Glu Ala Val Pro Lys Gly Ala Met Gly Asn Met
    1410                1415                1420

Gly Ser Val Pro Pro Gln Pro Pro Gln Asp Ala Gly Gly Ala Pro
1425                1430                1435                1440

Asp His Ser Met Leu Tyr Tyr Tyr Gly Gln Ile His Met Tyr Glu Gln
                1445                1450                1455

Asp Gly Gly Leu Glu Asn Leu Gly Ser Cys Gln Val Met Arg Ser Gln
            1460                1465                1470
```

-continued

Pro Pro Gln Pro Gln Ala Cys Gln Asp Ser Ile Gln Pro Gln Pro Leu
            1475                1480                1485

Pro Ser Pro Gly Val Asn Gln Val Ser Ser Thr Val Asp Ser Gln Leu
        1490                1495                1500

Leu Glu Ala Pro Gln Ile Asp Phe Asp Ala Ile Met Asp Asp Gly Asp
1505                1510                1515                1520

His Ser Ser Leu Phe Ser Gly Ala Leu Ser Pro Ser Leu Leu His Ser
                1525                1530                1535

Leu Ser Gln Asn Ser Ser Arg Leu Thr Thr Pro Arg Asn Ser Leu Thr
            1540                1545                1550

Leu Pro Ser Ile Pro Ala Gly Ile Ser Asn Met Ala Val Gly Asp Met
        1555                1560                1565

Ser Ser Met Leu Thr Ser Leu Ala Glu Glu Ser Lys Phe Leu Asn Met
1570                1575                1580

Met Thr
1585

<210> SEQ ID NO 15
<211> LENGTH: 464
<212> TYPE: PRT
<213> ORGANISM: Homo sapiens

<400> SEQUENCE: 15

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

```
Glu Asp Thr Leu Ser Asp Ser Asp Glu Asp Glu Glu Asp
            260                 265                 270

Glu Glu Glu Ile Asp Val Val Thr Val Lys Arg Arg Ser Ser
    275                 280                 285

Ser Asn Thr Lys Ala Val Thr Thr Phe Thr Ile Thr Val Arg Pro Lys
290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
            355                 360                 365

Ser Leu Ser Pro Arg Asn Ser Asp Ser Glu Asp Ser Glu Arg Arg Arg
            370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
                420                 425                 430

Leu Gln Ala Glu Glu His Gln Leu Leu Leu Glu Lys Glu Lys Leu Gln
            435                 440                 445

Ala Arg Gln Gln Gln Leu Leu Lys Lys Ile Glu His Ala Arg Thr Cys
450                 455                 460

<210> SEQ ID NO 16
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 16
cttcgcaagt accgcttc                                                  18

<210> SEQ ID NO 17
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 17
atatcccccg agcttcaa                                                  18

<210> SEQ ID NO 18

<400> SEQUENCE: 18

000

<210> SEQ ID NO 19

<400> SEQUENCE: 19

000
```

```
<210> SEQ ID NO 20

<400> SEQUENCE: 20

000

<210> SEQ ID NO 21
<211> LENGTH: 44
<212> TYPE: DNA
<213> ORGANISM: Artificial Sequence
<220> FEATURE:
<223> OTHER INFORMATION: A synthetic oligonucleotide

<400> SEQUENCE: 21
taatacgact cactataggg caccatgccc agctgcaccg cgtc                    44

<210> SEQ ID NO 22
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 22
ttagcaagtc cgagcgtgtt cgat                                          24

<210> SEQ ID NO 23
<211> LENGTH: 44
<212> TYPE: DNA
<213> ORGANISM: Artificial Sequence
<220> FEATURE:
<223> OTHER INFORMATION: A synthetic oligonucleotide

<400> SEQUENCE: 23
aatacgactc actatagggc accatgagcg ggggcgagga gctg                    44

<210> SEQ ID NO 24
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 24
ttatctgagt ccggacctgt acag                                          24
```